United States Patent
Wei et al.

(10) Patent No.: US 8,592,469 B2
(45) Date of Patent: Nov. 26, 2013

(54) DIAZONAMIDE ANALOGS

(75) Inventors: Qi Wei, Dallas, TX (US); Ming Zhou, Dallas, TX (US); Xiaoming Xu, Dallas, TX (US); Charles Caldwell, Dallas, TX (US); Susan Harran, Dallas, TX (US); Lai Wang, Dallas, TX (US)

(73) Assignee: Joyant Pharmaceuticals, Inc., Dallas, TX (US)

( * ) Notice: Subject to any disclaimer, the term of this patent is extended or adjusted under 35 U.S.C. 154(b) by 75 days.

(21) Appl. No.: 13/447,259

(22) Filed: Apr. 15, 2012

(65) Prior Publication Data

US 2012/0270841 A1    Oct. 25, 2012

(51) Int. Cl.
*A01N 43/76* (2006.01)
*A61K 31/42* (2006.01)
*A61P 35/00* (2006.01)

(52) U.S. Cl.
USPC ............ 514/375; 540/457; 540/458; 540/459

(58) Field of Classification Search
USPC ............................ 540/457, 458, 459; 514/375
See application file for complete search history.

(56) References Cited

U.S. PATENT DOCUMENTS 7,517,895 B2 * 4/2009 Harran et al. ................. 514/366

FOREIGN PATENT DOCUMENTS

WO    WO2009-134938    5/2009
WO    WO 2009/143485 * 11/2009

OTHER PUBLICATIONS

Burgett et al. (Angewandte Chemie, International Edition (2003), 42(40), 4961-4966).*
Knowles et al. (Chemical Science (2011), 2(2), 308-311).*
International Search Report and Written Opinion in PCT/US2012/033715, (2012).

* cited by examiner

*Primary Examiner* — Bruck Kifle
(74) *Attorney, Agent, or Firm* — Richard Aron Osman

(57) ABSTRACT

Diazonamide analogs having anti-mitotic activity, useful for the treatment of cancer and other proliferative disorders, and related pharmaceutical compositions are provided.

20 Claims, 2 Drawing Sheets

DIAZONAMIDE ANALOGS

RELATED APPLICATION

This application claims priority to U.S. 61/478,059, filed Apr. 22, 2011, and having the same title and inventors.

INTRODUCTION

Diazonamide A is a mitotic spindle-disrupting agent first isolated from the marine organism *Diazona angulata*, having the structure:

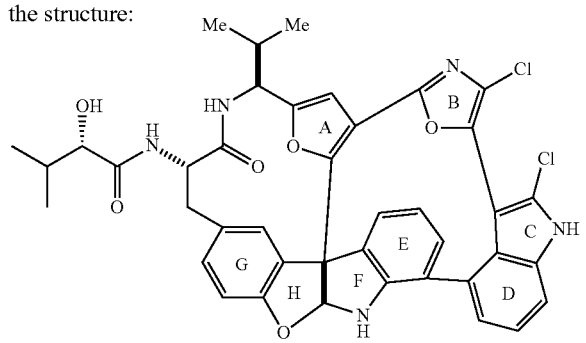

The preparation of diazonamide analogs via macrocyclic indoline intermediates bearing a carbobenzyloxy (Cbz) or o-nitrophenylsulfonyl protected amino group has been previously described. U.S. Pat. No. 7,022,720 and U.S. Pat. No. 7,517,895 correctly disclose the structure of diazonamide A and describe the synthesis of some of its analogs. U.S. Pat. No. 7,851,620 (continued with U.S. Ser No. 12/896,898) describes synthetic methods for the preparation of diazonamide analogs via indoline intermediates. U.S. Pat. No. 7,538,129 describes diazonamide A analogs. U.S. Ser No. 12/432,615 is a related pending application disclosing indoline, which lack the rigid macrocyclic structure bridging the A- and E-rings of the diazonamide skeleton. Disclosed here are compounds of formula (I) and additional novel diazonamide analogs which possess potent cytotoxic activity and are useful for the treatment of cell proliferative disorders.

SUMMARY OF THE INVENTION

The present invention is directed towards compounds of formula (I) and pharmaceutically acceptable salts and conjugates thereof, pharmaceutical compositions comprising a compound of formula (I) and/or a salt or conjugate thereof, modified forms of such compounds conjugated to stabilizing or targeting agents, and methods of making and using these compounds and formulations, wherein formula (I) is:

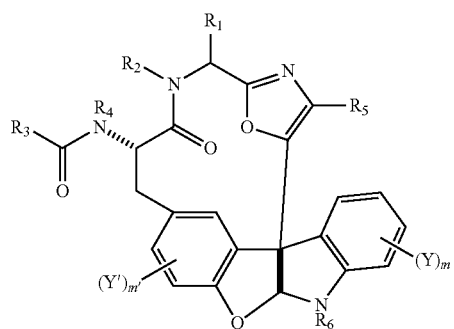

or a pharmaceutically acceptable salt or conjugate thereof;

wherein:
$R^1$ is optionally substituted C1-C4 alkyl;
$R^2$ is H, or optionally substituted C1-C4 alkyl;
$R^3$ is C1-C12 alkyl, C1-C12 heteroalkyl, C2-C12 alkenyl, C2-C12 heteroalkenyl, C3-C8 cycloalkyl, C3-C8 heterocyclyl, C4-C12 cycloalkylalkyl, C4-C12 heterocyclylalkyl, C6-C12 aryl, C5-C12 heteroaryl, C7-C14 arylalkyl, or C6-C14 heteroarylalkyl, each of which may be optionally substituted;
$R^4$ is H, or optionally substituted C1-C4 alkyl;
$R^5$ is optionally substituted C6-C12 aryl or optionally substituted C5-C12 heteroaryl;
$R^6$ is H, or optionally substituted C1-C4 alkyl;
each Y and Y' is independently halo, OH, C1-C4 alkoxy, or C1-C8 alkyl, C2-C8 alkenyl, C2-C8 alkynyl, C6-C12 aryl, or C7-C14 arylalkyl, or a heteroform of one of these, each of which may be optionally substituted;
m is 0-4; and
m' is 0-3.

The invention encompasses all combinations of various preferred embodiments/substitutions of formula (I) described herein.

In a further aspect, the invention provides a pharmaceutical composition comprising at least one compound of formula (I) or a disclosed embodiment thereof, and a pharmaceutically acceptable excipient.

In some embodiments, the compound of formula (I) or a disclosed embodiment thereof is a compound in one of the Tables provided herein, or a pharmaceutically acceptable salt or conjugate of one of these compounds.

In another aspect, the invention provides a method for treating or ameliorating a cell proliferative disorder, comprising administering to a subject in need thereof a therapeutically effective amount of at least one compound of formula (I) or a disclosed embodiment thereof or a salt, conjugate, or pharmaceutical composition thereof. In some embodiments, the amount administered is sufficient to inhibit cell proliferation. In other embodiments, the amount is sufficient to slow tumor growth or reduce tumor size. In some embodiments, the compound of formula (I) or a disclosed embodiment thereof is used in combination with another chemotherapeutic agent or approach.

Provided also are methods for inhibiting cell proliferation in a cell, comprising contacting the cell with a compound of one of the formula described herein, or a salt, or conjugate thereof, in an amount effective to inhibit cell proliferation. In some embodiments, the cells are in a cell line, such as a cancer cell line (e.g., a cell line derived from breast, prostate, pancreatic, lung, or hematopoietic cancers, etc.). In some embodiments, the cells are in a tissue, an in some such embodiments, the tissue can be in a subject. In other embodiments, the cells are in a tumor, and sometimes are in a tumor in a subject.

Provided also are methods for treating cancer in a subject in need of such treatment, comprising: administering to the subject a therapeutically effective amount of a compound of formula (I) or a disclosed embodiment thereof or a salt or conjugate thereof, as described herein, in an amount that is effective to treat or ameliorate said cancer.

The invention further provides methods for treating or ameliorating a condition related to aberrant cell proliferation. For example, provided are methods of treating or ameliorating a cell proliferative disorder in a subject, comprising administering a compound of formula (I) or a disclosed embodiment thereof or a salt or conjugate thereof, as described herein, to a subject in need thereof in an amount effective to treat or ameliorate the condition.

In the methods described herein, the subject may be a research animal (e.g., rodent, dog, cat, monkey), optionally containing a tumor such as a xenograft tumor (e.g., human tumor), for example, or may be a human.

DETAILED DESCRIPTION OF PARTICULAR EMBODIMENTS

Figure 1:
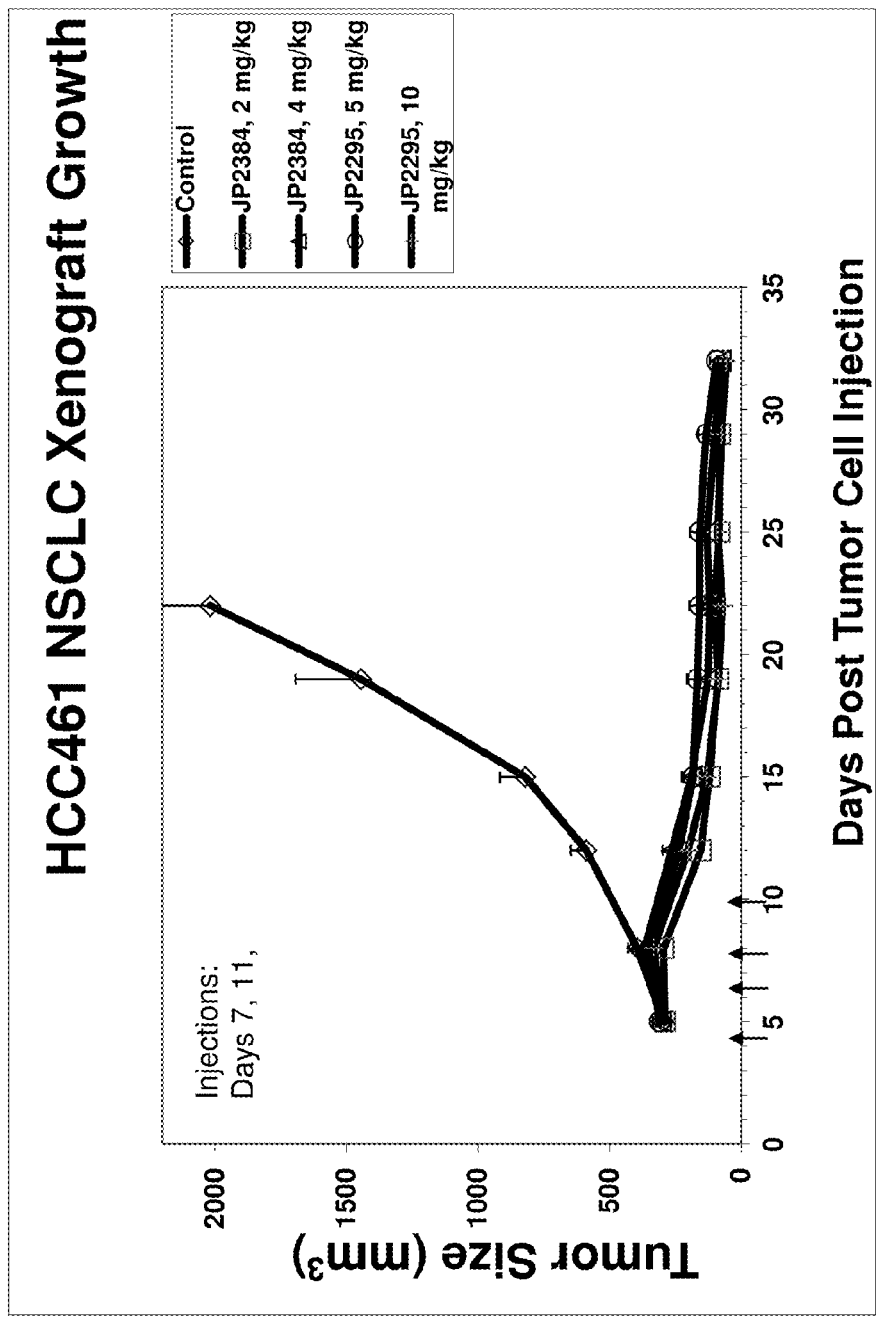
FIG. 1 shows data for subject compounds in an HCC461 human lung carcinoma xenograft model in mice.

The present invention may be understood more readily by reference to the following detailed description of the preferred embodiments of the invention and the Examples included herein. It is to be understood that the terminology used herein is for the purpose of describing specific embodiments only and is not intended to be limiting. It is further to be understood that unless specifically defined herein, the terminology used herein is to be given its traditional meaning as known in the relevant art.

As used herein, the singular forms "a", "an", and "the" include plural references unless indicated otherwise.

As used herein, the term "subject" refers to a human or animal subject. In preferred embodiments, the subject is human.

The terms "treat", "treating" or "treatment" in reference to a particular disease or disorder include prevention of the disease or disorder, and/or lessening, improving, ameliorating, alleviating or removing the symptoms and/or pathology of the disease or disorder.

The term "therapeutically effective amount" or "effective amount" is intended to mean that amount of a drug or pharmaceutical agent that will elicit a biological or medical response of a cell, tissue, system, animal or human that is being sought by a researcher, veterinarian, medical doctor or other clinician. The terms also can refer to reducing or stopping a cell proliferation rate (e.g., slowing or halting tumor growth) or reducing the number of proliferating cancer cells (e.g., removing part or all of a tumor). Sometimes, the rate or cell proliferation is reduced by 10%, 20%, 30%, 40%, 50%, 60%, or 70% or more. Sometimes, the number of proliferating cells is reduced by 10%, 20%, 30%, 40%, 50%, 60%, or 70% or more.

As used herein, the terms "alkyl," "alkenyl" and "alkynyl" include straight-chain, branched-chain and cyclic monovalent hydrocarbyl radicals, and combinations of these, which contain only C and H when they are unsubstituted. Examples include methyl, ethyl, isopropyl, isobutyl, tert-butyl, cyclohexyl, cyclopentylethyl, 2-propenyl, 3-butynyl, and the like. The total number of carbon atoms in each such group is sometimes described herein, e.g., when the group can contain up to twelve carbon atoms it may be described as 1-12C or as C1-C12 or as C1-12 or as $C_{1-12}$. When heteroatoms (typically N, O and S) are allowed to replace carbon atoms of an alkyl, alkenyl or alkynyl group, as in heteroalkyl groups, for example, the numbers describing the group, though still written as e.g. C1-C6, represent the sum of the number of carbon atoms in the group plus the number of such heteroatoms that are included as replacements for carbon atoms in the ring or chain being described.

Typically, the alkyl, alkenyl and alkynyl substituents of the invention contain 1-12C (alkyl) or 2-12C (alkenyl or alkynyl). Preferably they contain 1-8C (alkyl) or 2-8C (alkenyl or alkynyl). Sometimes they contain 1-4C (alkyl) or 2-4C (alkenyl or alkynyl). A single group can include more than one type of multiple bond, or more than one multiple bond; such groups are included within the definition of the term "alkenyl" when they contain at least one carbon-carbon double bond, and they are included within the term "alkynyl" when they contain at least one carbon-carbon triple bond.

"Heteroalkyl", "heteroalkenyl", and "heteroalkynyl" and the like are defined similarly to the corresponding hydrocarbyl (alkyl, alkenyl and alkynyl) groups, but the 'hetero' terms refer to groups that contain one or more heteroatoms selected from O, S and N and combinations thereof, within the backbone residue; thus at least one carbon atom of a corresponding alkyl, alkenyl, or alkynyl group is replaced by one of the specified heteroatoms to form a heteroalkyl, heteroalkenyl, or heteroalkynyl group. Preferably, each heteroalkyl, heteroalkenyl and heteroalkynyl group contains only 1-2 heteroatoms as part of the skeleton of backbone of the heteroalkyl group, i.e., not including substituents that may be present. Hence, heteroalkyls include alkoxyls such as O-alkyl, alkyl ethers, secondary and tertiary alkyl amines, alkyl sulfides, alkyl sulfonyls, and the like.

The typical and preferred sizes for heteroforms of alkyl, alkenyl and alkynyl groups are generally the same as for the corresponding hydrocarbyl groups, and the substituents that may be present on the heteroforms are the same as those described above for the hydrocarbyl groups. Where such groups contain N, the nitrogen atom may be present as NH or it may be substituted if the heteroalkyl or similar group is described as optionally substituted. Where such groups contain S, the sulfur atom may optionally be oxidized to SO or $SO_2$ unless otherwise indicated. For reasons of chemical stability, it is also understood that, unless otherwise specified, such groups do not include more than three contiguous heteroatoms as part of the heteroalkyl chain, although an oxo group may be present on N or S as in a nitro or sulfonyl group. Thus —C(O)NH$_2$ can be a C2 heteroalkyl group substituted with =O; and —SO$_2$NH— can be a C2 heteroalkylene, where S replaces one carbon, N replaces one carbon, and S is substituted with two =O groups.

While "alkyl" as used herein includes cycloalkyl and cycloalkylalkyl groups, the term "cycloalkyl" may be used herein to specifically describe a saturated or partially saturated, monocyclic or fused or spiro polycyclic, carbocycle that is connected via a ring carbon atom, and "cycloalkylalkyl" may be used to describe a carbocyclic non-aromatic group that is connected to the base molecule through an alkyl linker. Similarly, "heterocyclyl" may be used to describe a non-aromatic cyclic group that contains at least one heteroatom as a ring member and that is connected to the molecule via a ring atom of the cyclic group, which may be C or N; and "heterocyclylalkyl" may be used to describe such a group that is connected to another molecule through an alkyl linker. The sizes and substituents that are suitable for the cycloalkyl, cycloalkylalkyl, heterocyclyl, and heterocyclylalkyl groups are the same as those described above for alkyl groups. Frequently, cycloalkyl and heterocyclyl groups are C3-C8, and cycloalkylalkyl or heterocyclylalkyl groups are C4-C12. The size of a cycloalkylalkyl or heterocyclylalkyl group describes the total number of carbon atoms or of carbon atoms plus heteroatoms that replace carbon atoms of an alkyl, alkenyl, alkynyl, cycloalkyl, or cycloalkylalkyl portion. As used herein, these terms also include rings that contain a double bond or two, as long as the ring is not aromatic.

As used herein, "acyl" encompasses groups comprising an alkyl, alkenyl, alkynyl, aryl or arylalkyl radical attached at one of the two available valence positions of a carbonyl carbon atom (which may be depicted herein as —C(=O)R, —C(O)R, or COR) where R is an alkyl, alkenyl, alkynyl, aryl, or arylalkyl group, and heteroacyl refers to the corresponding groups wherein at least one carbon other than the carbonyl carbon has been replaced by a heteroatom chosen from N, O and S. Thus heteroacyl includes, for example, —C(=O)OR and —C(=O)NR$_2$ as well as —C(=O)-heteroaryl. Also included within the definition of heteroacyl groups are thioacyl substituents, e.g., —C(=S)R, and imine groups, e.g., —C(=NH)R.

Acyl and heteroacyl groups are bonded to any group or molecule to which they are attached through the open valence of the carbonyl carbon atom. Typically, they are C1-C8 acyl groups, which include formyl, acetyl, trifluoroacetyl, pivaloyl, and benzoyl, and C2-C8 heteroacyl groups, which include methoxyacetyl, ethoxycarbonyl, and 4-pyridinoyl. The hydrocarbyl groups, aryl groups, and heteroforms of such groups that comprise an acyl or heteroacyl group can be substituted with the substituents described herein as generally suitable substituents for each of the corresponding component of the acyl or heteroacyl group.

"Aromatic" moiety or "aryl" moiety refers to a monocyclic or fused bicyclic moiety having the well-known characteristics of aromaticity; examples include phenyl and naphthyl. Carbocyclic aryl rings and ring systems typically 6-12 carbon ring atoms, and may include a saturated or partially unsaturated carbocyclic ring fused to an aromatic ring, e.g., a tetrahydronaphthalene, indane or indene ring system. Similarly, "heteroaromatic" and "heteroaryl" refer to such monocyclic or fused bicyclic ring systems which contain as ring members one or more heteroatoms selected from O, S and N. The inclusion of a heteroatom permits aromaticity in 5-membered rings as well as 6-membered rings. Typical heteroaromatic systems include monocyclic C5-C6 aromatic groups such as pyridyl, pyrimidyl, pyrazinyl, pyridazinyl, triazinyl, thienyl, furanyl, pyrrolyl, pyrazolyl, thiazolyl, isothiazolyl, oxazolyl, isoxazolyl, imidazolyl, triazolyl, thiadiazolyl, oxadiazolyl, and tetrazolyl rings, and the fused bicyclic moieties formed by fusing one of these monocyclic groups with a phenyl ring or with any of the heteroaromatic monocyclic groups to form a C8-C10 bicyclic group such as indolyl, benzimidazolyl, indazolyl, benzotriazolyl, isoquinolinyl, quinolinyl, benzothiazolyl, benzofuranyl, benzothienyl, benzisoxazolyl, pyrazolopyridyl, quinazolinyl, quinoxalinyl, cinnolinyl, and the like. Any monocyclic or fused ring bicyclic system which has the characteristics of aromaticity in terms of electron distribution throughout the ring system is included in this definition. It also includes bicyclic groups where at least one ring has the characteristics of aromaticity, even though it may be fused to a nonaromatic ring. Typically, the ring systems contain 5-12 ring member atoms. Preferably the monocyclic aryl and heteroaryl groups contain 5-6 ring members, and the bicyclic aryl and heteroaryl groups contain 8-10 ring members.

Similarly, "arylalkyl" and "heteroarylalkyl" refer to aromatic and heteroaromatic ring systems which are bonded to their attachment point through a linking group such as an alkylene, including substituted or unsubstituted, saturated or unsaturated, cyclic or acyclic linkers. Typically the linker is C1-C8 alkyl or a heteroform thereof, preferably a C1-C4 alkyl. These linkers may also include a carbonyl group, thus making them able to provide substituents as an acyl or heteroacyl moieties.

"Arylalkyl" groups as used herein are hydrocarbyl groups if they are unsubstituted, and are described by the total number of carbon atoms in the ring and alkylene or similar linker. Thus a benzyl group is a C7-arylalkyl group, and phenylethyl is a C8-arylalkyl. Preferably, an arylalkyl group includes one or two optionally substituted phenyl rings and a C1-C4 alkylene that is unsubstituted or is substituted with one or two C1-C4 alkyl groups or C1-C4 heteroalkyl groups, where the alkyl or heteroalkyl groups can optionally cyclize to form a ring such as cyclopropane, dioxolane, or oxacyclopentane, and wherein the alkyl or heteroalkyl groups may be optionally fluorinated. Examples of arylalkyl groups include optionally substituted benzyl, phenylethyl, diphenylmethyl, and triphenylmethyl groups. Optional substituents when present on the aryl ring of an arylalkyl group are the same as those described herein for an aryl ring. Arylalkyl groups typically contain from 7-20 atoms, preferably 7-14 atoms.

"Heteroarylalkyl" as described above refers to a moiety comprising an aryl group that is attached through a linking group, and differs from "arylalkyl" in that at least one ring atom of the aryl moiety or one atom in the linking group is a heteroatom selected from N, O and S. The heteroarylalkyl groups are described herein according to the total number of atoms in the ring and linker combined, and they include aryl groups linked through a heteroalkyl linker; heteroaryl groups linked through a hydrocarbyl linker such as an alkylene; and heteroaryl groups linked through a heteroalkyl linker. For example, heteroaryl groups include pyridylmethyl, pyridylethyl, —O-benzyl, and the like. Heteroarylalkyl groups typically contain from 6-20 atoms, preferably 6-14 atoms.

"Alkylene" as used herein refers to a divalent hydrocarbyl group; because it is divalent, it can link two other groups together. Typically it refers to —(CH$_2$)$_n$— where n is 1-8 and preferably n is 1-4, though where specified, an alkylene can also be substituted by other groups, and can be of other lengths, and the open valences need not be at opposite ends of a chain. Thus —CH(Me)- and —C(Me)$_2$- may also be referred to as alkylenes, as can a cyclic group such as cyclopropan-1,1-diyl. However, for clarity, a three-atom linker that is an alkylene group, for example, refers to a divalent group in which the available valences for attachment to other groups are separated by three atoms such as —(CH$_2$)$_3$—, i.e., the specified length represents the number of atoms linking the attachment points rather than the total number of atoms in the hydrocarbyl group: —C(Me)$_2$- would thus be a one-atom linker, since the available valences are separated by only one atom. Where an alkylene group is substituted, the substituents include those typically present on alkyl groups as described herein, thus —C(=O)— is an example of a one-carbon substituted alkylene. Where it is described as unsaturated, the alkylene may contain one or more double or triple bonds.

"Heteroalkylene" as used herein is defined similarly to the corresponding alkylene groups, but the 'hetero' terms refer to groups that contain one or more heteroatoms selected from O, S and N and combinations thereof, within the backbone residue; thus at least one carbon atom of a corresponding alkylene group is replaced by one of the specified heteroatoms to form a heteroalkylene group. Thus, —C(=O)NH— is an example of a two-carbon substituted heteroalkylene, where N replaces one carbon, and C is substituted with a =O group.

"Heteroform" as used herein refers to a derivative of a group such as an alkyl, aryl, or acyl, wherein at least one carbon atom of the designated carbocyclic group has been replaced by a heteroatom selected from N, O and S. Thus the heteroforms of alkyl, alkenyl, cycloalkyl, alkynyl, acyl, aryl, and arylalkyl are heteroalkyl, heteroalkenyl, heterocyclyl, heteroalkynyl, heteroacyl, heteroaryl, and heteroarylalkyl, respectively. It will be understood that the heteroform of an aryl or arylalkyl moiety may contain one less "C" atom than the corresponding all carbon system, because the inclusion of a heteroatom permits aromaticity in 5-membered rings. For example, the heteroform of C6-C12 aryl is C5-C12 heteroaryl, and the heteroform of C7-C20 arylalkyl is C6-C20 heteroarylalkyl. It is understood that no more than two N, O or S atoms are ordinarily connected sequentially, except where an oxo group is attached to N or S to form a nitro or sulfonyl group, or in the case of certain heteroaromatic rings, such as triazine, triazole, tetrazole, oxadiazole, thiadiazole, and the like.

Unless otherwise indicated, the term "oxo" refers to =O.

"Halo", as used herein, includes fluoro, chloro, bromo and iodo. Fluoro, chloro, and bromo are often preferred.

"Amino" as used herein refers to $NH_2$, but where an amino is described as "substituted" or "optionally substituted", the term includes $NR_2$ wherein each R is independently H, or is an alkyl, alkenyl, alkynyl, acyl, aryl, or arylalkyl group or a heteroform of one of these groups, as further defined herein, each of which may be optionally substituted with the substituents described herein as suitable for the corresponding type of group. The term also includes forms wherein the two R groups on one nitrogen atom (i.e., $NR_2$) are linked together to form a 3-8 membered monocyclic azacyclic ring or an 8-12 membered bicyclic fused azacyclic ring system, each of which may be saturated, unsaturated or aromatic and which may contain 1-3 heteroatoms including the azacyclic ring nitrogen atom independently selected from N, O and S as ring members (i.e., 0-2 heteroatoms selected from N, O and S in addition to the nitrogen atom of the azacyclic ring), and which may be optionally substituted with the substituents described as suitable for alkyl groups or, if $NR_2$ comprises an aromatic group, it may be optionally substituted with the substituents described as typical for aryl or heteroaryl groups. Preferred such azacyclic rings include pyrrolidine, piperidine, homopiperidine, morpholine, thiomorpholine, piperazine, and homopiperazine.

Amino groups may optionally be in a protected or unprotected form. One of skill in the art would appreciate that appropriate amine protecting groups may vary depending on the functionality present in the particular molecule and the nature of the amino group. Suitably protected amines may include, for example, amines protected as carbamates (e.g., tert-butoxycarbonyl (Boc), benzyloxycarbonyl (Cbz), fluorenylmethyloxy-carbonyl (Fmoc), allyloxycarbonyl (Alloc) or (trialkylsilyl)ethoxycarbonyl), carboxamides (e.g., formyl, acyl or trifluoroacetyl, benzoyl), sulfonamides, phthalimides, succinimides, Schiff's base derivatives, and the like. Also included are alkyl or allyl amines, as well as trialkylsilyl protected amines.

Where an amine is present in protected form, it is sometimes desirable to remove the protecting group. Thus, the methods of the present invention also optionally include a step of removing any protecting groups on an amine or aminoalkyl group.

The terms "alkylsulfonyl" and "arylsulfonyl" as used herein refer to moieties of the form —$SO_2$alkyl or —$SO_2$aryl, where alkyl and aryl are defined as above. Optionally fluorinated $C_{1-4}$alkyl, and optionally substituted phenyl groups are preferred for sulfonyl moieties. The phenyl groups of an arylsulfonyl moiety may be optionally substituted with one or more substituents suitable for an aryl ring; for example, they may be substituted by halo, methyl, nitro, alkoxy, amino, or the like. Such sulfonyl moieties, when present on oxygen form sulfonates. Such sulfonyl moieties form sulfonamides when present on nitrogen, and sulfones when present on carbon. Representative sulfonates include, e.g., —$OSO_2$Me (mesylate), —$OSO_2CF_3$ (triflate), —$OSO_2$tolyl (tosylate), and the like.

The term "alkoxycarbonyl" as used herein refers to a moiety of the form —COOR', where R' is C1-C8 alkyl, C2-C8 alkenyl, C5-C6 aryl, or C7-C14 arylalkyl, trialkylsilyl, or the like, each of which may be optionally substituted. When present on nitrogen, such alkoxycarbonyl moieties form carbamates, which are frequently used as nitrogen protecting groups. In some such embodiments, R' may be optionally halogenated C1-C4 alkyl (e.g., tert-butyl, methyl, ethyl, 2,2,2-trichloroethyl, 1,1-dimethyl-2,2,2-trichloroethyl), allyl, optionally substituted benzyl, fluorenylmethyl, or trialkylsilyl (e.g., triisopropylsilyl, triethylsilyl, tert-butyldimethylsilyl). When present on carbon, such moieties may also be referred to as carboxylate esters, carboalkoxy groups, or the like. In some embodiments containing a carboxylate ester functional group, R' is preferably a $C_{1-4}$ alkyl group. In some such embodiments, R' is methyl, ethyl, n-propyl, isopropyl, n-butyl, isobutyl, s-butyl or t-butyl.

The term "substituted" means that the specified group or moiety bears one or more non-hydrogen substituents. The term "unsubstituted" means that the specified group bears no such substituents.

"Optionally substituted" as used herein indicates that the particular group or groups being described may have no non-hydrogen substituents, or the group or groups may have one or more non-hydrogen substituents (i.e., the group may be substituted or unsubstituted). If not otherwise specified, the total number of such substituents that may be present is equal to the number of H atoms present on the unsubstituted form of the group being described. Where an optional substituent is attached via a double bond, such as a carbonyl oxygen (=O), the group takes up two available valences, so the total number of substituents that may be included is reduced according to the number of available valences.

Alkyl, alkenyl and alkynyl groups are often substituted to the extent that such substitution makes sense chemically. Typical substituents include, but are not limited to, halo, OH, =O, =N—CN, =N—OR, =NR, OR, $NR_2$, SR, SOR, $SO_2R$, $SO_2NR_2$, $NRSO_2R$, $NRCONR_2$, NRCOOR, NRCOR, CN, COOR, $CONR_2$, OOCR, COR, and $NO_2$, wherein each R is independently H, optionally fluorinated C1-C8 alkyl, C2-C8 heteroalkyl, C1-C8 acyl, C2-C8 heteroacyl, C2-C8 alkenyl, C2-C8 heteroalkenyl, C2-C8 alkynyl, C2-C8 heteroalkynyl, C6-C12 aryl, C5-C12 heteroaryl, C5-C20 arylalkyl, or C5-C20 heteroarylalkyl, and each R is optionally substituted with one or more groups selected from halo, OH, =O, =N—CN, =N—OR', =NR', OR', $NR'_2$, SR', SOR', $SO_2R'$, $SO_2NR'_2$, $NR'SO_2R'$, $NR'CONR'_2$, $NR'COOR'$, $NR'COR'$, CN, COOR', $CONR'_2$, OOCR', COR', and $NO_2$, wherein each R' is independently H, optionally fluorinated C1-C8 alkyl, C2-C8 heteroalkyl, C1-C8 acyl, C2-C8 heteroacyl, C6-C12 aryl, C5-C12 heteroaryl, C5-C20 arylalkyl, or C5-C20 heteroarylalkyl. Alkyl, alkenyl and alkynyl groups can also be substituted by C1-C8 acyl, C2-C8 heteroacyl, C6-C12 aryl or C5-C12 heteroaryl, each of which can be substituted by the substituents that are appropriate for the particular group.

Preferred substituents when present on an alkyl, alkenyl or alkynyl group, or a heteroform of one of these, include halo, OH, =O, OR, SR, and $NR_2$, where R is defined as above; sometimes, R is H, optionally fluorinated C1-C4 alkyl, or optionally fluorinated C1-C4 acyl. Particularly preferred substituents when present on $R^3$ include OH, =O, C1-C4 alkoxy, OAc, NHAc, $NH_2$, and NHMe. Sometimes, optional substituents present on an alkyl, alkenyl or alkynyl group, or a heteroform of one of these, include $NRSO_2R$, $NRCONR_2$, COOR, or $CONR_2$, where R is defined as above; preferably, each R is independently H, optionally fluorinated C1-C4 alkyl, or is C6-C12 aryl, C5-C12 heteroaryl, C7-C20 arylalkyl, or C6-C20 heteroarylalkyl, each of which may be optionally substituted.

Aryl, heteroaryl and heterocyclyl moieties may be substituted with a variety of substituents including optionally fluorinated C1-C8 alkyl, C2-C8 alkenyl, C2-C8 alkynyl, C1-C8 acyl, and heteroforms of these, C6-C12 aryl, C5-C12 for heteroaryl, C6-20 arylalkyl (C5-20 for heteroarylalkyl), each of which can itself be further substituted; other substituents for aryl and heteroaryl moieties include halo, OH, OR, $CH_2OH$, $CH_2OR$, $CH_2NR_2$, $NR_2$, SR, SOR, $SO_2R$, $SO_2NR_2$, $NRSO_2R$, $NRCONR_2$, NRCOOR, NRCOR, CN, COOR, $CONR_2$, OOCR, C(O)R, and $NO_2$, wherein each R is independently H, optionally fluorinated C1-C8 alkyl, C2-C8 heteroalkyl, C2-C8 alkenyl, C2-C8 heteroalkenyl, C2-C8 alkynyl, C2-C8 heteroalkynyl, C6-C12 aryl, C5-C12 heteroaryl, C7-C20 arylalkyl, or C6-C20 heteroarylalkyl, and each R is optionally substituted as described above for alkyl groups. The substituent groups on an aryl or heteroaryl group may of course be further substituted with the groups described herein as suitable for each type of group that comprises the substituent. Preferred substituents when present on an aryl, heteroaryl and heterocyclyl moieties include halo, OH, OR, $CH_2OH$, $CH_2OR$, $CH_2NR_2$, SR, $NR_2$, CN, COOR, $CONR_2$, and $NO_2$, where R is defined as above, or optionally substituted C6-C12 aryl or C5-C12 heteroaryl ring.

Where an arylalkyl or heteroarylalkyl group is described as optionally substituted, the substituents may be on either the alkyl or heteroalkyl portion or on the aryl or heteroaryl portion of the group. The substituents optionally present on the alkyl or heteroalkyl portion are the same as those described above for alkyl groups generally; the substituents optionally present on the aryl or heteroaryl portion are the same as those described above for aryl groups generally.

The invention encompasses isomers of the subject compounds, particularly stereoisomers, such as wherein the carbon atom bearing the substituent $R^1$ in formula (I) or the corresponding atom in disclosed embodiments of formula (I), has the (S)-configuration.

The present invention provides novel indoline analogs of formula (I), which are useful for the treatment or amelioration of proliferative disorders, in particular, cancer.

The invention encompasses all combinations of preferred embodiments and preferred substituents described herein.

Preferably, $R^1$ is optionally substituted C2-C4 alkyl, preferably C2-C4 alkyl, preferably propyl or butyl, preferably isopropyl or t-butyl.

Preferably, $R^2$, $R^4$ and $R^6$ are independently H or methyl, preferably H. A substituent at $R^4$ may function as a protecting group, and methods described herein include an optional deprotection step to remove any protecting groups present on the molecule.

Preferably, $R^3$ is a substituted methyl of the general formula ($-CR^aR^bR^c$) wherein $R^a$ is OH, OR, $CH_2OR$, SR, and $NR_2$, where each R is independently H, optionally halogenated (preferably fluorinated or chlorinated) C1-C4 alkyl, or optionally halogenated C1-C4 acyl, and preferably OH; and each of $R^b$ and $R^c$ is independently H, C1-C6 alkyl, C2-C6 alkenyl, C2-C6 alkynyl, C3-C8 cycloalkyl, C3-C8 cycloalkylalkyl, C6-C12 aryl, C7-C14 arylalkyl, or a heteroform of one of these, each of which may be optionally substituted, and preferably H or C1-C4 lower alkyl, more preferably H and isopropyl or t-butyl, respectively; or $R^b$ and $R^c$ may be taken together with the carbon to which they are attached to form a C3-C8 cycloalkyl or a C3-C8 heterocyclyl ring, which may be optionally substituted. For example, $R^b$ and $R^c$ may be taken together to form an optionally substituted cyclopropyl, cyclobutyl, cyclopentyl, cyclopentenyl, cyclohexyl, cyclohexenyl, tetrahydrofuran, tetrahydropyran, tetrahydrothiofuran, tetrahydrothiopyran, pyrrolidine, or piperidine ring, and the like. In a preferred embodiment, each of $R^b$ and $R^c$ are taken together to form a cyclohexyl or a cyclopentyl ring. In some embodiments, the ring formed by $R^b$ and $R^c$ may be fused to a substituted or unsubstituted phenyl ring to provide, for example, and indenyl or tetrahydronaphthyl ring system.

In other preferred embodiments, $R^3$ is C1-C4 alkyl, C3-C6 cycloalkyl, C4-C8 cycloalkylalkyl, or C6-C8 arylalkyl, each of which may be optionally substituted. In preferred embodiments, the alkyl group comprising part of $R^3$ is substituted with at least one substituent selected from the group consisting of OH, OR, $CH_2OR$, SR, and $NR_2$, where each R is independently H, optionally fluorinated C1-C4 alkyl, or optionally fluorinated C1-C4 acyl. Preferably $R^3$ is substituted with at least one substituent selected from the group consisting of OH, OMe, OAc, $NH_2$, NHMe, $CH_2OH$ and NHAc. In more specific embodiments, $R^3$ is a C1-C8, preferably C1-C4, more preferably C2-C3, most preferably C2 straight chain, branched, or cycloalkyl group, each of which is substituted on the carbon atom adjacent to the carbonyl group that is part of $R^5$ with OH, OMe, OAc, $NH_2$, NHMe, $CH_2OH$ or NHAc, preferably OH.

Preferably $R^5$ is an optionally substituted phenyl, naphthyl, benzimidazole, benzoxazole, benzthiazole, pyridinyl, pyrimidinyl, pyrazinyl or pyridazinyl ring, and more preferably, $R^5$ is an optionally substituted oxazole, oxazoline, thiazole, thiazoline, pyrazole, pyrazoline, imidazole, imidazoline, pyrrole, pyrroline, isoxazole, isoxazoline, isothiazole, isothiazoline, oxadiazole, thiadiazole, triazole or tetrazole ring.

Preferred substituents include halo, nitro, cyano, or optionally fluorinated C1-C4 alkyl, optionally fluorinated C1-C4 alkoxy, $COOR^S$, $CONR^9_2$, C6-C12 aryl or C5-C12 heteroaryl, each of which may be optionally substituted; where $R^8$ is H, or C1-C8 alkyl, C2-C8 alkenyl, C6-C12 aryl, or C7-C14 arylalkyl, or a heteroform of one of these, each of which may be optionally substituted; and each $R^9$ is independently H, or C1-C12 alkyl, C1-C12 heteroalkyl, C2-C12 alkenyl, C2-C12 heteroalkenyl, C3-C8 cycloalkyl, C3-C8 heterocyclyl, C4-C12 cycloalkylalkyl, C4-C12 heterocyclylalkyl, C6-C12 aryl, C5-C12 heteroaryl, C7-C14 arylalkyl, or C6-C14 heteroarylalkyl, each of which may be optionally substituted; or two $R^9$ on the same N can cyclize to form an optionally substituted 3- to 8-membered azacyclic ring, optionally containing an additional heteroatom selected from N, O, and S as a ring member; preferred such azacyclic rings include pyrrolidine, piperidine, homopiperidine, morpholine, thiomorpholine, piperazine, and homopiperazine.

In certain preferred embodiments, $R^5$ is an optionally substituted oxazole or thiazole ring. In some such embodiments, $R^5$ is an oxazole ring substituted with an optionally substituted C6-C12 aryl or C5-C12 heteroaryl ring. In some embodiments, $R^5$ is an oxazole ring substituted with one or more alkyl, halo, carboxylic acid, ester or amide substituents.

In specific embodiments of formula (I), $R^5$ is an optionally substituted heterocyclic or heteroaromatic ring of the formula:

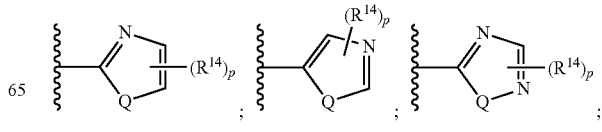

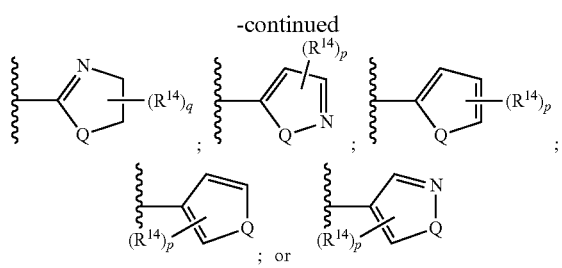

wherein Q is O, S or NR$^{13}$, where R$^{13}$ is H or C1-C4 alkyl; each R$^{14}$ is independently halo, nitro, cyano, or optionally fluorinated C1-C4 alkyl, optionally fluorinated C1-C4 alkoxy, COOR$^{8}$, CONR$^{9}_{2}$, C6-C12 aryl or C5-C12 heteroaryl, each of which may be optionally substituted; where R$^{8}$ is H, or C1-C8 alkyl, C2-C8 alkenyl, C6-C12 aryl, or C7-C14 arylalkyl, or a heteroform of one of these, each of which may be optionally substituted; and each R$^{9}$ is independently H, or C1-C12 alkyl, C1-C12 heteroalkyl, C2-C12 alkenyl, C2-C12 heteroalkenyl, C3-C8 cycloalkyl, C3-C8 heterocyclyl, C4-C12 cycloalkylalkyl, C4-C12 heterocyclylalkyl, C6-C12 aryl, C5-C12 heteroaryl, C7-C14 arylalkyl, or C6-C14 heteroarylalkyl, each of which may be optionally substituted; or two R$^{9}$ on the same N can cyclize to form an optionally substituted 3- to 8-membered azacyclic ring, optionally containing an additional heteroatom selected from N, O, and S as a ring member; p is 0-3; and q is 0 to 4. Such azacyclic rings may be saturated, unsaturated or aromatic; preferred such azacyclic rings include pyrrolidine, piperidine, homopiperidine, morpholine, thiomorpholine, piperazine, and homopiperazine.

In certain preferred embodiments of formula (I), R$^{5}$ is

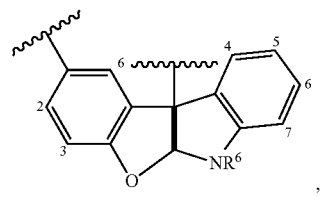

wherein each R$^{11}$ and R$^{12}$ is independently H, halo, nitro, cyano, or optionally fluorinated C1-C4 alkyl, optionally fluorinated C1-C4 alkoxy, COOR$^{8}$, CONR$^{9}_{2}$, C6-C12 aryl or C5-C12 heteroaryl, each of which may be optionally substituted; where R$^{8}$ is H, or C1-C8 alkyl, C2-C8 alkenyl, C6-C12 aryl, or C7-C14 arylalkyl, or a heteroform of one of these, each of which may be optionally substituted; and each R$^{9}$ is independently H, or C1-C12 alkyl, C1-C12 heteroalkyl, C2-C12 alkenyl, C2-C12 heteroalkenyl, C3-C8 cycloalkyl, C3-C8 heterocyclyl, C4-C12 cycloalkylalkyl, C4-C12 heterocyclylalkyl, C6-C12 aryl, C5-C12 heteroaryl, C7-C14 arylalkyl, or C6-C14 heteroarylalkyl, each of which may be optionally substituted; or two R$^{9}$ on the same N can cyclize to form an optionally substituted 3- to 8-membered azacyclic ring, optionally containing an additional heteroatom selected from N, O, and S as a ring member. Such azacyclic rings may be saturated, unsaturated or aromatic; preferred such azacyclic rings include pyrrolidine, piperidine, homopiperidine, morpholine, thiomorpholine, piperazine, and homopiperazine.

In some such embodiments, each R$^{11}$ and R$^{12}$ is independently H, halo, nitro, cyano, C1-C4 alkyl, C1-C4 alkoxy, COOR$^{8}$, or CONR$^{9}_{2}$, C6-C12 aryl or C5-C12 heteroaryl, each of which may be optionally substituted, and in particular embodiments R$^{11}$ is halo, nitro, cyano, C1-C4 alkyl, C1-C4 alkoxy, COOR$^{8}$, or CONR$^{9}_{2}$, C6-C12 aryl or C5-C12 heteroaryl, each of which may be optionally substituted, and R$^{12}$ is H.

Substituents on the indole and tyrosine components of the macrocylic ring of formula (I), Y and Y' respectively, are located by the corresponding ring positions as shown in formula II:

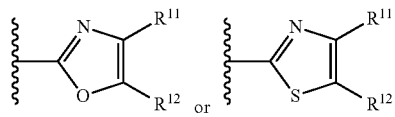

(II)

wherein R6 is as defined in formula (I); hence, Y may be at one or more of positions 4, 5, 6 and 7 of the indole moiety, and Y' may be at one or more of positions 2, 3 and 5 of the tyrosine moiety.

Preferably each Y and Y' is independently halo (F, Cl, Br, or I), OH, C1-C4 alkoxy, preferably halo, particulary Cl or F; preferably m is 3, 2, 1 or preferably, 0; and preferably m' is 2, 1 or preferably 0.

In preferred embodiments, Y is at one or more of positions 5, 6 and 7, one or more of positions 5 and 7, one of positions 5, 6 and 7, one of positions 5 and 7, position 5 only, or position 7 only. In preferred embodiments, Y' is at one or more of positions 2 and 3, one of positions 2 and 3, position 2 only, or position 3 only. In particular embodiments one or both rings are substituted.

The invention encompasses all combinations of preferred embodiments and preferred substituents as if each had been laboriously set forth, i.e. preferred substituents at R1 combined with each preferred substituent at one or more of R2-R6 and Y/Y'/m/m', etc. Particular examples of such combinations include:

Ia. Oxazole, 4 oxazoyl derviatives with esters other than methyl ester in position 4:
R$^{1}$ is C1-C4 alkyl, particulary isopropyl or t-butyl,
R$^{2}$, R$^{4}$ and R$^{6}$ are H,
R$^{3}$ is a substituted methyl of the formula (—CR$^{a}$R$^{b}$R$^{c}$) wherein R$^{a}$ is OH, R$^{b}$ is H, and R$^{c}$ is isopropyl or t-butyl,
R$^{5}$ is

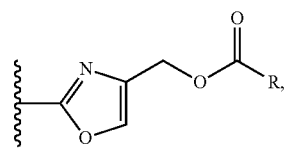

wherein R is H, C1-C4 alkyl or C1-C4 alkyloxy, particulary methyl, H, or methoxy, and
Y is F and/or Cl, preferably F, at postion 5 and/or 7, preferably 5,
m is 0, 1 or 2, preferably 0 or 1, and
m' is 0.

Ib. Oxazole, 4 oxazoyl derviatives with phosphate esters in position 4:
R$^{1}$ is C1-C4 alkyl, particulary isopropyl or t-butyl,
R$^{2}$, R$^{4}$ and R$^{6}$ are H, $R^3$ is a substituted methyl of the formula ($-CR^aR^bR^c$) wherein $R^a$ is OH, $R^b$ is H, and $R^c$ is isopropyl or t-butyl,
$R^5$ is

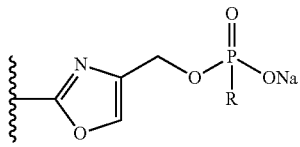

wherein R is H, C1-C4 alkyl, particulary methyl or H, and
Y is F and/or Cl, preferably F, at postion 5 and/or 7, preferably 5,
m is 0, 1 or 2, preferably 0 or 1, and
m' is 0.

II. Oxazole, 4 oxazoyl derviatives with alcohol or ketone in position 4:
$R^1$ is C1-C4 alkyl, particulary isopropyl or t-butyl,
$R^2$, $R^4$ and $R^6$ are H,
$R^3$ is a substituted methyl of the formula ($-CR^aR^bR^c$) wherein $R^a$ is OH, $R^b$ is H, and $R^c$ is isopropyl or t-butyl,
$R^5$ is

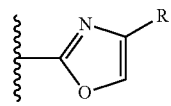

wherein R is hydroxyl or C1-C4 alcohol, or C1-C4 ketone, particularly hydroxyl, hydroxy methyl, 1-hydroxy ethyl or 1-hydroxy isopropyl, and
Y is F and/or Cl, preferably F, at postion 5 and/or 7, preferably 5,
m is 0, 1 or 2, preferably 0 or 1, and
m' is 0.

III. Oxazole, 4 oxazoyl derviatives with amide, amine, carbamate, or sulfonamide in position 4:
$R^1$ is C1-C4 alkyl, particulary isopropyl or t-butyl,
$R^2$, $R^4$ and $R^6$ are H,
$R^3$ is a substituted methyl of the formula ($-CR^aR^bR^c$) wherein $R^a$ is OH, $R^b$ is H, and $R^c$ is isopropyl or t-butyl,
$R^5$ is

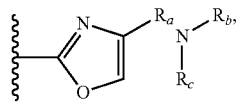

wherein Ra is optionally substituted C0-C4 alkyl, Rb and Rc are independently H, C1-C8 alkyl, C2-C8 alkenyl, C6-C12 aryl, or a heteroform of one of these, each of which may be optionally substituted, particularly wherein Ra is C0 or C1 alkyl, Rb is H, and Rc is H, methyl, methyl ester, methyl sulfonyl or phenyl sulfonyl, and
Y is F and/or Cl, preferably F, at 5 and/or 7, preferably 5,
m is 0, 1 or 2, preferably 0 or 1, and
m' is 0.

IV. Oxazole, 4 oxazoyl derviatives with cyano in position 4:
$R^1$ is C1-C4 alkyl, particulary isopropyl or t-butyl,
$R^2$, $R^4$ and $R^6$ are H,
$R^3$ is a substituted methyl of the formula ($-CR^aR^bR^c$) wherein $R^a$ is OH, $R^b$ is H, and $R^c$ is isopropyl or t-butyl,
$R^5$ is

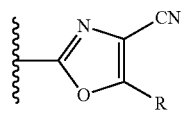

wherein R is H, C1-C8 alkyl, C2-C8 alkenyl, C6-C12 aryl, or a heteroform of one of these, each of which may be optionally substituted, particularly wherein R is H, methyl, or NHAc, and
Y is F and/or Cl, preferably F, at postion 5 and/or 7, preferably 5,
m is 0, 1 or 2, preferably 0 or 1, and
m' is 0.

V. Oxazole, 4 oxazoyl derviatives with a heterocycle in position 4:
$R^1$ is C1-C4 alkyl, particulary isopropyl or t-butyl,
$R^2$, $R^4$ and $R^6$ are H,
$R^3$ is a substituted methyl of the formula ($-CR^aR^bR^c$) wherein $R^a$ is OH, $R^b$ is H, and $R^c$ is isopropyl or t-butyl,
$R^5$ is

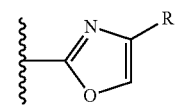

wherein R is a C3-C8 heterocyclyl, C4-C12 heterocyclylalkyl, C5-C12 heteroaryl, or C6-C14 heteroarylalkyl, each of which may be optionally substituted, particularly an optionally substituted oxazole, oxazoline, thiazole, thiazoline, pyrazole, pyrazoline, imidazole, imidazoline, pyrrole, pyrroline, isoxazole, isoxazoline, isothiazole, isothiazoline, oxadiazole, thiadiazole, triazole or tetrazole ring, wherein preferred substituents are halo, nitro, cyano, or optionally fluorinated C1-C4 alkyl, optionally fluorinated C1-C4 alkoxy, $COOR^S$, $CONR^9_2$, C6-C12 aryl or C5-C12 heteroaryl, each of which may be optionally substituted; where $R^8$ is H, or C1-C8 alkyl, C2-C8 alkenyl, C6-C12 aryl, or C7-C14 arylalkyl, or a heteroform of one of these, each of which may be optionally substituted; and each $R^9$ is independently H, or C1-C12 alkyl, C1-C12 heteroalkyl, C2-C12 alkenyl, C2-C12 heteroalkenyl, C3-C8 cycloalkyl, C3-C8 heterocyclyl, C4-C12 cycloalkylalkyl, C4-C12 heterocyclylalkyl, C6-C12 aryl, C5-C12 heteroaryl, C7-C14 arylalkyl, or C6-C14 heteroarylalkyl, each of which may be optionally substituted; optionally containing an additional heteroatom selected from N, O, and S as a ring member, and
Y is F and/or Cl, preferably F, at postion 5 and/or 7, preferably 5,
m is 0, 1 or 2, preferably 0 or 1, and
m' is 0.

Where chiral carbons are included in chemical structures, unless a particular orientation is depicted, both stereoisomeric forms are intended to be encompassed. Compounds of formula (I) and disclosed embodiments thereof may, for example, have two or more asymmetric centers and therefore exist in different enantiomeric and/or diastereomeric forms. All optical isomers and stereoisomers of the compounds described herein, and mixtures thereof, are considered to be within the scope of the invention, including the racemate, one or more enantiomeric forms, one or more diastereomeric forms, or mixtures thereof. In particular, racemic mixtures of single diastereomers such as the ones described, diastereomers having an diastereomeric excess (d.e.) of greater than 90% or greater than about 95%, and enantiomers having an enantiomeric excess (e.e.) of greater than 90% or greater than about 95%. Similarly, where double bonds are present, the compounds can exist in some cases as either cis or trans isomers; the invention includes each isomer individually as well as mixtures of isomers. Where the compounds described may also exist in tautomeric forms, this invention relates to the use of all such tautomers and mixtures thereof.

Compounds of formula (I) and disclosed embodiments thereof can be supplied in free base form, or can be supplied as a pharmaceutically acceptable salt, or as a mixture of the free base form and the corresponding salt. The compounds of the invention may be isolated as salts where an ionizable group such as a basic amine or a carboxylic acid is present. The invention includes the salts of these compounds that have pharmaceutically acceptable counterions. Such salts are well known in the art, and include, for example, salts of acidic groups formed by reaction with organic or inorganic bases, and salts of basic groups formed by reaction with organic or inorganic acids, as long as the counterions introduced by the reaction are acceptable for pharmaceutical uses. Examples of inorganic bases with alkali metal hydroxides (e.g., sodium hydroxide, potassium hydroxide, etc.), alkaline earth metal hydroxides (e.g., of calcium, magnesium, etc.), and hydroxides of aluminum, ammonium, etc. Examples of organic bases that could be used include trimethylamine, triethylamine, pyridine, picoline, ethanolamine, diethanolamine, triethanolamine, dicyclohexylamine, N,N'-dibenzylethylenediamine, etc.

Suitable salts include those of inorganic acids such as hydrochlorides, hydrobromides, sulfates, hydrosulfates, and the like, or organic acid addition salts. Examples of inorganic acids that could be used include hydrochloric acid, hydrobromic acid, nitric acid, sulfuric acid, phosphoric acid, etc. Examples of organic acids include formic acid, oxalic acid, acetic acid, tartaric acid, methanesulfonic acid, benzenesulfonic acid, malic acid, methanesulfonic acid, benzenesulfonic acid, p-toluenesulfonic acid, etc. Also included are salts with basic amino acids such as arginine, lysine, ornithine, etc., and salts with acidic amino acids such as aspartic acid, glutamic acid, etc.

In addition, compounds of formula (I) and disclosed embodiments thereof may be coupled or conjugated to moieties such as a targeting agent. Among such targeting agents are antibodies or immunologically active fragments thereof, including single-chain antibody forms directed against tumor antigens or against receptors or integrins associated with tumors, peptidomimetics directed against these moieties, and the like. In addition, compounds of formula (I) and disclosed embodiments thereof may be coupled or conjugated to an excipient, such as a polymer excipient, such as polyethylene glycol for altering pharmacokinetics, such as described in the Advanced Drug Delivery Reviews theme issue (Vol 61, November 2009) entitled, Polymer Therapeutics: Clinical Applications and Challenges for Development, including Pasut and Veronese, Adv Drug Delivery Rev 61 (13):1177-1188, 2009. The selected PEG may be of any convenient molecular weight, and may be linear or branched, and may be optionally conjugated through a linker. The average molecular weight of PEG will preferably range from about 2 kiloDalton (kDa) to about 100 kDa, more preferably from about 5 kDa to about 40 kDa.

Compounds of formula (I) and disclosed embodiment thereofs are useful in treating or ameliorating cell proliferative diseases. In particular, the compounds and methods described herein are useful for the treatment or amelioration of tumors and malignancies associated with breast, ovary, lung (SCLC and NSCLC), colon, rectum, prostate, testes, skin (e.g., melanoma, basal cell carcinoma, and squamous cell carcinoma), pancreas, liver, kidney, brain (e.g., glioma, meningioma, schwannomas, and medulloblastomas), and the blood and hematopoietic system, including, e.g., leukemia, non-Hodgkins lymphoma, and multiple myeloma.

In the methods described herein, for example, cell proliferation may be reduced, and/or cell death, such as apoptosis or apoptotic cell death, may be induced. The cell proliferative disorder may be a tumor or non-tumor cancer in a human or animal subject.

The compounds and methods provided herein for reducing cell proliferation and/or inducing cell death may be used alone, or in conjunction with or in combination with surgical, radiation, chemotherapeutic, immunotherapy, and bone marrow and/or stem cell transplantation methods, or with other palliative agents, such as compounds that aid in nutrition or general health, anti-emetic agents, and the like.

In some embodiments, the compounds of the present invention are administered in combination with a chemotherapeutic agent, and used to reduce cell proliferation, induce cell death, and/or treat or ameliorate a cell proliferative disorder.

The compounds described herein are also useful against certain drug resistant tumors and cancer cell lines, in particular against cancers that are resistant to TAXOL® and/or vinca alkaloid anti-cancer agents.

Where an additional chemotherapeutic drug is administered, it is typically one known to have cytostatic, cytotoxic or antineoplastic activity. These agents include, without limitation, antimetabolites (e.g., cytarabine, fludaragine, 5-fluoro-2'-deoxyuridine, gemcitabine, hydroxyurea, methotrexate); DNA active agents (e.g., bleomycin, chlorambucil, cisplatin, cyclophosphamide); intercalating agents (e.g., adriamycin and mitoxantrone); protein synthesis inhibitors (e.g., L-asparaginase, cycloheximide, puromycin); topoisomerase type I inhibitors (e.g., camptothecin, topotecan or irinotecan); topoisomerase type II inhibitors (e.g. etoposide, teniposide anthraquinones, anthracyclines and podophyllotoxin); microtubule inhibitors (e.g., taxanes, such as paclitaxel and docetaxel, colcemid, colchicines, or vinca alkaloids, such as vinblastine and vincristine); kinase inhibitors (e.g. flavopiridol, staurosporin and hydroxystaurosporine), drugs that affect Hsp90 (e.g. geldanomycin and geldanomycin derivatives, radicicol, purine derivatives and antibodies or antibody fragments that selectively bind to Hsp90), TRAIL, a TRAIL receptor antibody, TNF-α or TNF-β, and/or radiation therapy.

In some preferred embodiments, the additional cancer therapeutic agent is TRAIL, a TRAIL receptor antibody, TNF-α or TNF-β. In other preferred embodiments, the additional drugs for co-administration with the compounds of the invention affects Hsp90 (heat-shock protein 90).

Suitable Hsp90 inhibitors include ansamycin derivatives such as geldanomycin and geldanomycin derivatives including 17-(allylamino)-17-desmethoxygeldanamycin (17-AAG), its dihydro derivative, 17-AAGH$_2$, and 17-amino derivatives of geldanamycin such as 17-dimethylaminoethylamino-17-demethoxy-geldanamycin (17-DMAG), 11-oxogeldanamycin, and 5,6-dihydrogeldanamycin, which are disclosed in U.S. Pat. Nos. 4,261,989; 5,387,584; and 5,932,566, each of which is incorporated herein by reference. Other suitable Hsp90 inhibitors include radicicol and oximes and other analogs thereof, disclosed in Soga, et al., *Curr. Cancer Drug Targets*, 3, 359-69 (2003), and in Yamamoto, et al., *Angew. Chem.*, 42, 1280-84 (2003); and in Moulin, et al., *J.*

*Amer. Chem. Soc., vol* 127, 6999-7004 (2005); purine derivatives such as PU3, PU24FCI and PUH64 (see Chiosis et al., *ACS Chem. Biol. Vol.* 1(5), 279-284 (2006) and those disclosed in PCT Application No. WO 2002/0236075; related heterocyclic derivatives disclosed in PCT Application No. WO 2005/028434; and 3,4-diarylpyrazole compounds disclosed in Cheung, et al., *Bioorg. Med. Chem. Lett., vol.* 15, 3338-43 (2005). Antibodies or antibody fragments that selectively bind to Hsp90 may also be administered as drugs to cause inhibition of Hsp90, and can be used in combination with the compounds of the invention.

Where a compound described herein is utilized in conjunction with or in combination with another therapeutic, the two agents may be co-administered, or they may be administered separately where their administration is timed so the two agents act concurrently or sequentially.

Accordingly, the compositions used in the methods described herein include at least one compound of the invention, and can optionally include one or more additional cytotoxic or cytostatic therapeutic such as, but not limited to, those disclosed above. Similarly, the methods of the invention include methods wherein a subject diagnosed as in need of treatment for cancer is treated with at least one compound or composition of the invention, and is simultaneously or concurrently treated with one or more of the additional therapeutic agents described above.

Formulation and Administration

The formulations useful in the invention include standard formulations such as those set forth in *Remington's Pharmaceutical Sciences*, latest edition, Mack Publishing Co., Easton, Pa., incorporated herein by reference. Such formulations include those designed for oral delivery, slow release, topical administration, parenteral administration, or any other suitable route as determined by an attending physician or veterinarian. Thus administration may be systemic or local. Suitable vehicles or excipients include liposomes, micelles, nanoparticles, polymeric matrices, buffers, and the full range of formulations known to practitioners.

Systemic formulations include those designed for injection (e.g., intramuscular, intravenous or subcutaneous injection) and those prepared for transdermal, transmucosal, or oral administration. The formulation will generally include a diluent as well as, in some cases, adjuvants, buffers, preservatives and the like. The compounds can be administered also in liposomal compositions or as microemulsions.

Injection methods are sometimes appropriate routes for administration of the compounds for systemic treatments and sometimes also for localized treatments. These include methods for intravenous, intramuscular, subcutaneous, and other methods for internal delivery that bypass the mucosal and dermal barriers to deliver the composition directly into the subject's living tissues.

For injection, formulations can be prepared in conventional forms as liquid solutions or suspensions or as solid forms suitable for solution or suspension in liquid prior to injection or as emulsions. Suitable excipients include, for example, water, saline, dextrose, glycerol and the like. Such compositions may also contain amounts of nontoxic auxiliary substances such as wetting or emulsifying agents, pH buffering agents and the like, such as, for example, sodium acetate, sorbitan monolaurate, and so forth.

Various sustained release systems for drugs have also been devised and can be utilized with the compounds of the invention. See, for example, U.S. Pat. No. 5,624,677. The present compositions can be utilized in such controlled-release delivery systems where appropriate.

Systemic administration may also include relatively non-invasive methods such as the use of suppositories, transdermal patches, transmucosal delivery and intranasal administration. Oral administration is also suitable for compounds of the invention. Suitable forms include syrups, capsules, tablets, and the like as in understood in the art.

Selection of a particular route of administration for a given subject and indication is well within the ordinary level of skill in the art. For example, rectal delivery as a suppository is often appropriate where the subject experiences nausea and vomiting that precludes effective oral delivery. Transdermal patches are commonly capable of delivering a controlled-release dosage over several days or to a specific locus, and are thus suitable for subjects where these effects are desired.

Transmucosal delivery is also appropriate for some of the compositions and methods of the invention. Thus the compositions of the invention may be administered transmucosally using technology and formulation methods that are known in the art.

Regardless of the route of administration selected, the compounds described herein, which may be used in a suitable hydrated form, and/or the pharmaceutical compositions of the present invention, are formulated into pharmaceutically-acceptable dosage forms by conventional methods known to those of skill in the art.

Actual dosage levels of the active ingredients in the pharmaceutical compositions of the present invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion or metabolism of the particular compound being employed, the rate and extent of absorption, the duration of the treatment, other drugs, compounds and/or materials used in combination with the particular compound employed, the age, sex, weight, condition, general health and prior medical history of the patient being treated, and like factors well known in the medical arts.

For administration to animal or human subjects, the dosage of a compound of the invention is typically 10-2400 mg per administration. However, dosage levels are highly dependent on the nature of the condition, the condition of the patient, the judgment of the practitioner, and the frequency and mode of administration. Selection of a dosage of such compounds is within the skill of an ordinary artisan, and may be accomplished by starting at a relatively low dosage and increasing the dosage until an acceptable effect is achieved.

Frequency of administration of the compounds of the invention can also be readily determined by one skilled in the art using well known techniques. For example, the patient may be administered a low dosage of a compound or composition of the invention at a low frequency such as once per day or less often; and the dosage and/or frequency of administration may be systematically increased until a desired effect is achieved in the patient.

Synthetic Processes

The subject compounds have been prepared through an efficient multi-step process, as shown in Scheme 1. A key step in the process involves the electrochemical oxidative cyclization of a phenolic intermediate to provide an indoline compound of formula (I), which may be further functionalized as exemplified by the compounds described herein. The oxidative cyclization was described in U.S. application Ser. No. 12/134,984, filed 6 Jun. 2008, and published as US 2009/0005572.

As shown in Scheme 1, dipeptide starting materials were prepared under standard conditions known in the art, for example, by coupling an N-hydroxysuccinimide ester or another activated ester of a protected amino acid with serine. It will be understood by one of skill in the art that a wide variety of suitable conditions may be utilized to form the dipeptide starting materials, including the extensive body of literature describing synthesis of peptides and peptide mimetics.

The dipeptide was reacted with an optionally substituted indole and an activating reagent, optionally in the presence of a protic acid, to provide an indole-containing dipeptide. Suitable activating reagents include, for example, carboxylic acid anhydrides, mixed anhydrides, or acyl halides (e.g., acetic anhydride, trifluoroacetic anhydride, acetyl chloride, oxalyl chloride), sulfonic acid anhydrides or halides (e.g., methanesulfonic anhydride, trifluoromethanesulfonic anhydride, methanesulfonyl chloride), mineral acid halides (e.g., thionyl chloride, or phosphoryl chloride), and the like.

In a preferred embodiment, the activating agent was acetic anhydride, and the reaction was conducted in acetic acid as a protic solvent. In a particularly preferred embodiment, the dipeptide and an optionally substituted indole were reacted with acetic anhydride in acetic acid at about 80° C., to provide the desired compound.

The preparation of N-acetyl tryptophan derivatives by reaction of serine or N-acetyl serine and an optionally substituted indole in acetic anhydride and acetic acid has been previously reported. Y. Yokoyama, et al., *Tetrahedron Letters* (1999), 40: 7803; Y. Yokoyama, et al., *Eur. J. Org. Chem.* (2004), 1244; Y. Konda-Yamada, et al., *Tetrahedron* (2002), 58: 7851; M. W. Orme, et al., U.S. Pat. No. 6,872,721. However, the preparation of other acylated tryptophan derivatives under these conditions, such as the dipeptide analogs of the present invention, has not been previously described to our knowledge.

Esterification of the free carboxylic acid, followed by oxidative cyclization of the dipeptide intermediate with an oxidizing agent, for example, DDQ, provided an oxazole intermediate. It will be understood by those in the art that other oxidative conditions could be utilized, such as, for example, the use of 7,7,8,8-tetracyanoquinodimethane (TCNQ), ceric ammonium nitrate, hypervalent iodide reagents, and the like.

Deprotection of the protected amino group, if present, and amide bond formation provided a phenolic intermediate. Electrochemical oxidative cyclization of the phenolic intermediate provided a macrocyclic indoline compound. Such compounds were further elucidated to compounds of formula (I) through a series of straightforward chemical transformation. For example, removal of the Cbz group and acylation or amide bond formation was used to provide compounds of formula (I), wherein $R^5$ is an acyl substituent, for example —C(O)$R^3$. One of skill in the art will understand that the order of these steps could be reversed, depending on the nature of the functional groups to be installed, and the protecting groups utilized.

Scheme 1 provides a general synthetic route useful for the preparation of macrocyclic indoline compounds of formula (I). Those skilled in the art will appreciate that certain reaction conditions can be varied without altering the essence of the present invention. For example, coupling reactions can be accomplished with a variety of activated esters, such as by way of example only N-hydroxybenzotriazole ester, perfluorophenyl ester, N-hydroxyphthalimide esters, activated esters generated by the reaction of the carboxylic acid with a carbodiimide, and other activated esters conventionally used for acylation of an amine to form amide bonds. In addition, while amino groups are conveniently protected as carbobenzyloxy (Cbz) group, one of skill in the art will recognize that other suitable protecting groups could be utilized. Suitable protecting groups and methods to attach and remove them are well known in the art, and are described, for example, in T. H. Greene, Protective Groups in Organic Synthesis, $2^{nd}$ ed.

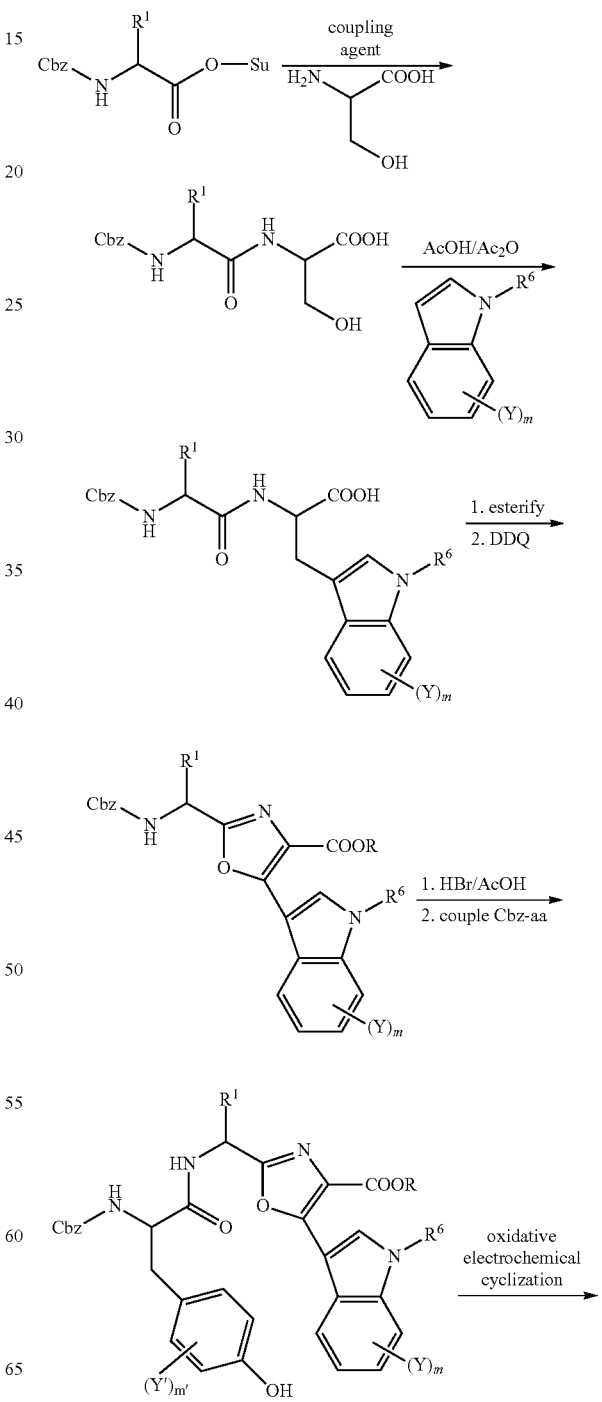

Scheme 1.

EXAMPLES

Synthesis of Compound 57

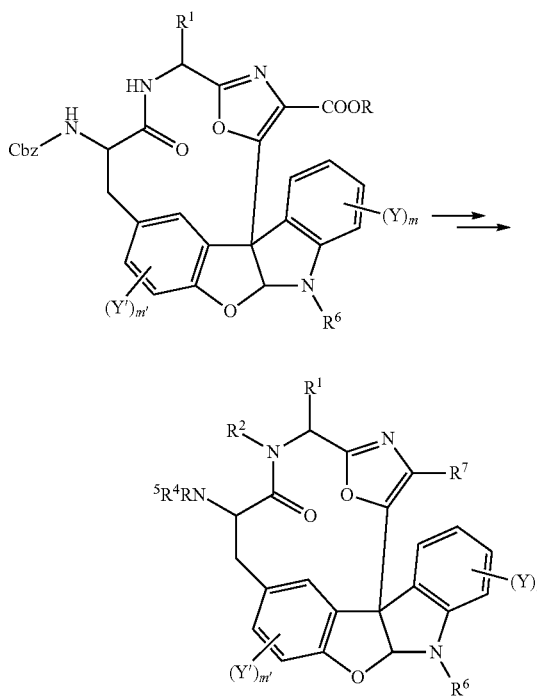

57

Step 1

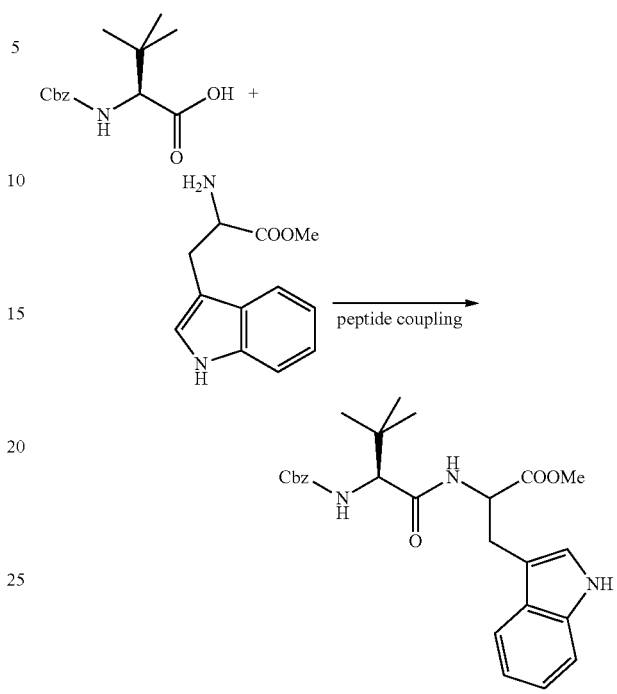

To a dry 100-ml flask with magnetic stir bar was added Cbz-L-α-t-butylglycine DCHA salt (5.0 g, 11.2 mmol), L-tryptophane methyl ester hydrochloride (3.14 g, 12.3 mmol, 1.1 eq.), HOBt (1.76 g, 13.4 mmol, 1.2 eq.), anhydrous DMF (30 ml) and N,N-diisopropylethylamine (2.93 ml, 16.8 mmol, 1.5 eq.). The reaction mixture was cooled to 0° C. followed by addition of EDC HCl (2.58 g, 13.4 mmol, 1.2 eq.). The resulting reaction mixture was stirred at RT for 16 h. The reaction was monitored by LCMS. The reaction mixture was diluted with EtOAc (300 ml)/water (100 ml). The organic phase was separated and the aqueous phase was extracted by EtOAc (2×50 ml). The combined organic layers were washed by water (100 ml), 10% aqueous NaHSO₄ (100 ml), water (100 ml), saturated NaHCO₃ (100 ml), and brine (2×100 ml), and then dried over Na₂SO₄. After concentration, the crude was used directly in the next step.

Step 2

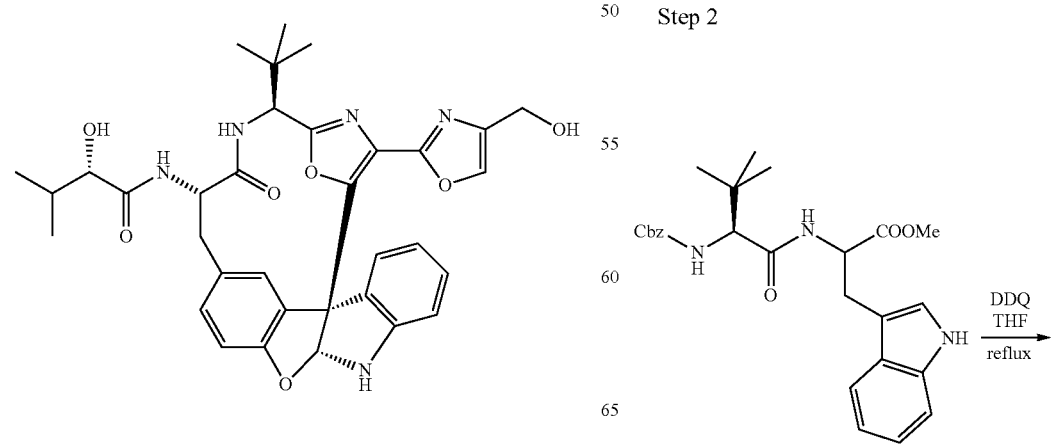

The process described in Scheme 1 is useful for the preparation of indolines of formula (I) in high yield and purity. In particular, the compounds of the present invention are available in good yield and with high diastereomeric purity, preferably in greater than 95% diastereomeric excess, sometimes 98% diastereomeric excess.

The following examples are offered to illustrate but not to limit the invention.

-continued

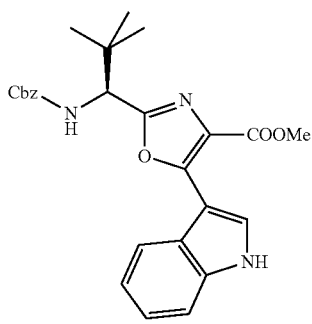

A solution of DDQ (6.2 g, 27.3 mmol, 2.4 eq.) in THF (100 ml) was added to the refluxing solution of the compound synthesized in Step 1 above (11.2 mmol) in THF (200 ml) and the dark solution was heated in reflux in an oil bath at 85° C. for 1 h. After cooling, the solvent was removed on a rotary evaporator. The residue was dissolved in ethyl acetate (500 ml), which was washed by water (200 ml), aqueous saturated NaHCO$_3$ (2×200 ml), water (2×200 ml), brine (100 ml) and dried over Na$_2$SO$_4$. After concentration, the mixture was purified by flash column chromatography (20% EtOAc in CH$_2$Cl$_2$). This yielded 3.24 g (64% yield) of product.

Step 3

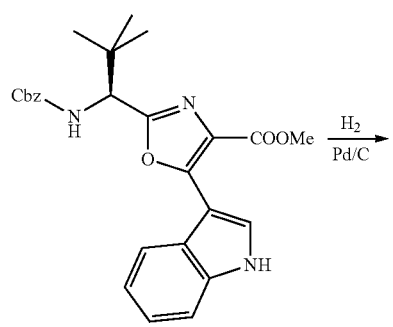

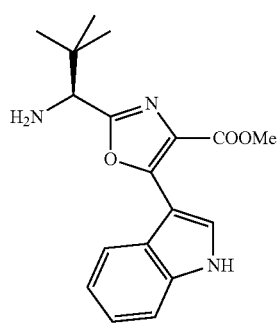

To a 100-ml flask containing material synthesized in Step 2 above (3.24 g, 7.02 mmol) was added methanol (30 ml) and Pd/C (10%) (650 mg, 0.61 mmol, 0.09 eq.) under N$_2$. H$_2$ balloon was added and the flask was purged with H$_2$ for 4 times. Then H$_2$ balloon was opened to the reaction system. After 3 h stirring almost no starting material remained. The reaction was stopped. The reaction mixture was filtered through a pad of Celite and the black cake was washed with methanol (3×10 ml). The filtrate was concentrated and the residue was used in next step directly without further purification.

Step 4

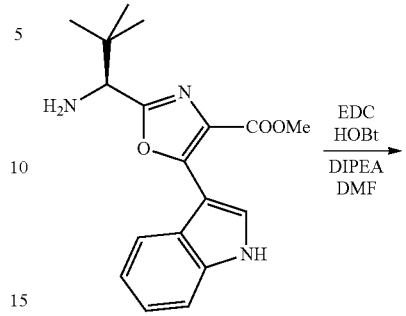

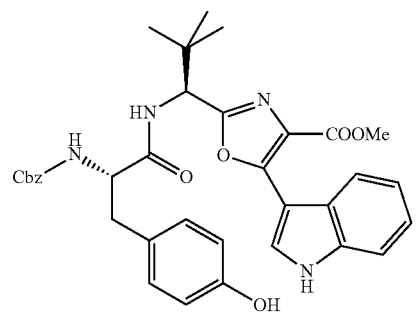

To a dry 100-ml flask with magnetic stir bar was added the amine synthesized in step 3 (2.06 g, 6.29 mmol), Cbz-L-tyrosine (1.98 g, 6.91 mmol, 1.1 eq.), HOBt (0.94 g, 6.91 mmol, 1.1 eq.), anhydrous DMF (30 ml) and N,N-diisopropylethylamine (1.31 ml, 7.54 mmol, 1.2 eq.). The reaction mixture was cooled to 0° C. followed by addition of EDC HCl (1.33 g, 6.91 mmol, 1.1 eq.). The resulting reaction mixture was stirred at RT for 16 h. The reaction was monitored by LCMS. The reaction mixture was diluted with EtOAc (300 ml)/water (100 ml). The organic phase was separated and the aqueous phase was extracted by EtOAc (2×50 ml). The combined organic layers were washed by water (100 ml), 10% aqueous NaHSO$_4$ (100 ml), water (100 ml), saturated NaHCO$_3$ (100 ml), and brine (2×100 ml), and then dried over Na$_2$SO$_4$. After concentration, the crude was used directly in the next step.

Step 5

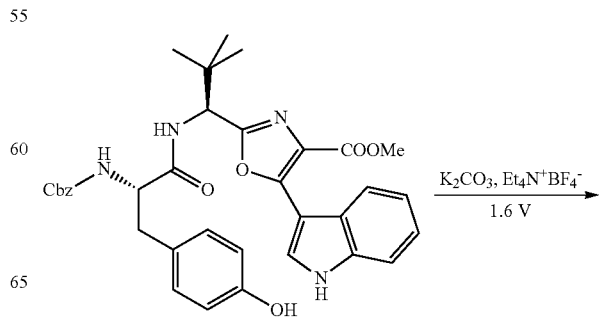

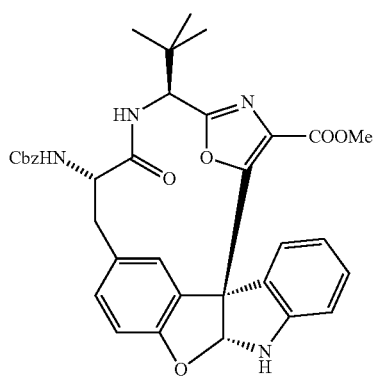

An electrochemical cell was assembled using a glass cylinder (6 cm diameter×11 cm height) and a custom rack (polypropylene and nylon) which supported 9 vertical graphite rods (6.15 mm diameter×12 cm length). The rods were arranged in a pattern of a ring with 6 anodes and 3 cathodes. Electrodes were immersed to a depth of 6.5 cm. The phenolic material synthesized in Step 4 above (5.00 g, 8.0 mmol), Et$_4$NBF$_4$ (4.00 g, 18.4 mmol, 2.9 eq.) and (NH$_4$)$_2$CO$_3$ (1.0 g, 10.4 mmol, 1.3 eq.) and ID water (4 ml) were added in DMF (200 ml). The solution was stirred vigorously in a stir plate (approx. 600 rpm). The electrochemical reaction was carried out at a potential of 1.5-1.6 volts. After 3 days, most of the original SM was consumed as determined by HPLC integration at 220 nM. The reaction mixture was concentrated on a rotary evaporator (bath temp. ≤35° C.) and dried further on a vacuum manifold. The residue was partitioned between EtOAc (200 ml) and 0.5 N aqueous HCl (60 ml). The organic layer was washed with saturated aqueous NaHCO$_3$ (50 ml) and then saturated aqueous NaCl (50 ml). The aqueous layers were extracted in succession with EtOAc (2×50 ml). The combined organic layers were dried (Na$_2$SO$_4$), decanted and evaporated. This material was purified by flash column chromatography with 20% EtOAc in CH$_2$Cl$_2$. This yielded 1.24 g (24.8% yield) of product as a mixture of stereoisomers (71:29 as measured by HPLC integration at 254 nM).

Step 6

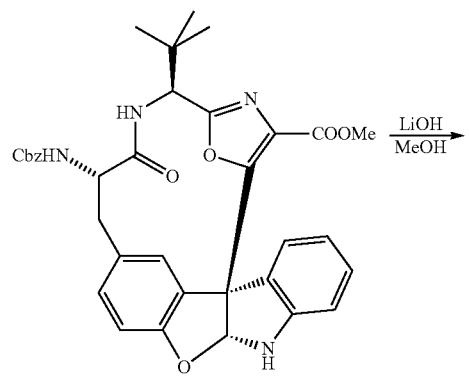

The compound synthesized in Step 6 (725 mg, 2.33 mmol) was dissolved in methanol (22 ml) and the solution was cooled in an ice bath. A solution of LiOH (558 mg, 23.3 mmol, 10 eq.) in water (7.0 ml) was added over 5 min. The ice bath was removed and the mixture was stirred for 18 h. The mixture was cooled in an ice bath and water (30 ml) was added followed by 1 N aqueous HCl (24 ml), keeping the reaction temperature below 10° C. The mixture was partitioned between water (15 ml) and EtOAc (100 ml), and the organic layer was washed with saturated aqueous NaCl. The aqueous layers were extracted in succession with EtOAc (30 ml). The combined organic layers were dried (Na$_2$SO$_4$), decanted, and evaporated to give the acid product as fine white crystals.

Step 7

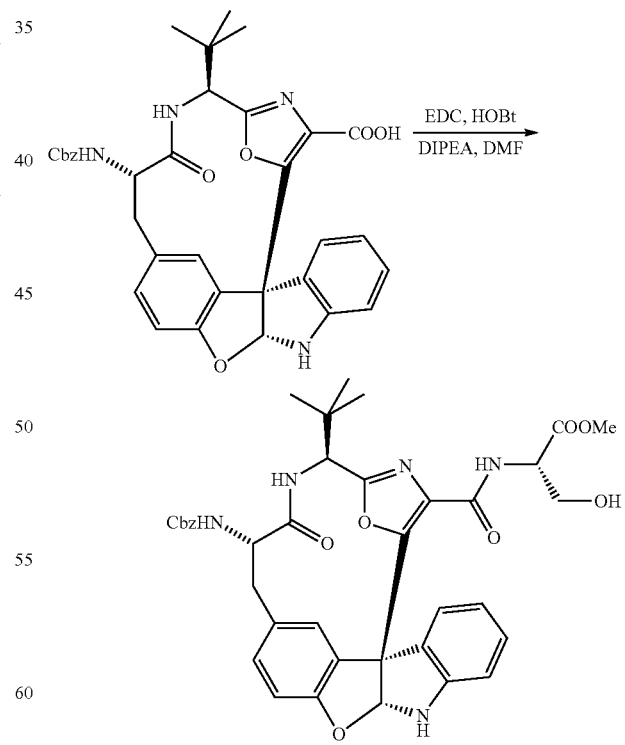

To a dry 100-ml flask with magnetic stir bar was added the carboxylic acid synthesized in step 6 above (2.33 mmol), L-serine methyl ester hydrochloride (435 mg, 2.8 mmol, 1.2 eq.), HOBt (378 mg, 2.8 mmol, 1.2 eq.), anhydrous DMF (25 ml) and N,N-diisopropylethylamine (1.01 ml, 5.83 mmol, 2.5 eq.). The reaction mixture was cooled to 0° C. followed by addition of EDC HCl (537 mg, 2.8 mmol, 1.2 eq.). The resulting reaction mixture was stirred at RT for 16 h. The reaction was monitored by LCMS. Most of solvents were evaporated under reduced pressure. The residue was diluted with EtOAc (100 ml)/water (30 ml). The organic phase was separated and the aqueous phase was extracted by EtOAc (2×20 ml). The combined organic layers were washed by water (40 ml), 10% aqueous NaHSO₄ (40 ml), water (40 ml), saturated NaHCO₃ (40 ml), and brine (2×40 ml), and then dried over Na₂SO₄. After concentration, the crude was used directly in the next step.

Step 8

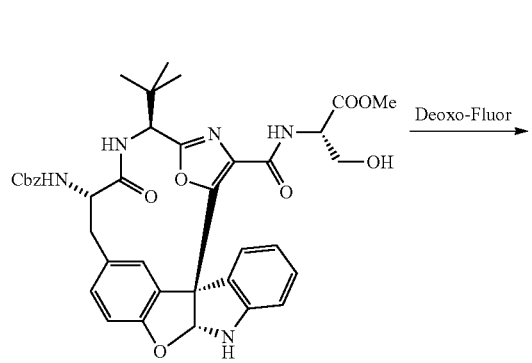

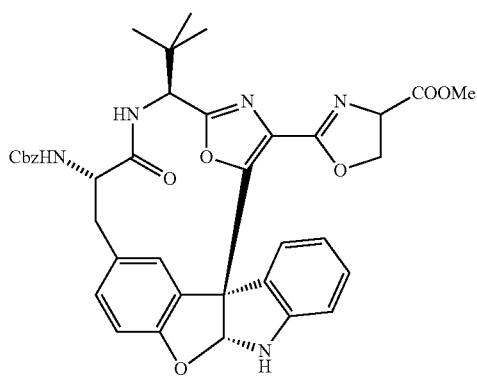

To a dry flask were added the crude product from Step 8 above (2.33 mmol) and anhydrous CH₂Cl₂ (40 ml). The reaction solution became cloudy as it was cooled to −20° C. in a dry ice/acetone/water bath. A freshly made stock solution of Bis(2-methoxyethyl)aminosulfur trifluoride (0.644 ml, 0.022 mmol, 2.8 eq.) in CH₂Cl₂ (4 ml) was added dropwise. The resulting reaction mixture was stirred at −20° C. for 1 h, and warmed to room temperature. The reaction mixture was quenched by addition of saturated aqueous NaHCO₃ (20 ml), diluted with EtOAc (100 ml), washed with water (2×30 ml) as well as brine (30 ml), and dried over Na₂SO₄. After concentration the residue was used in next step.

Step 9

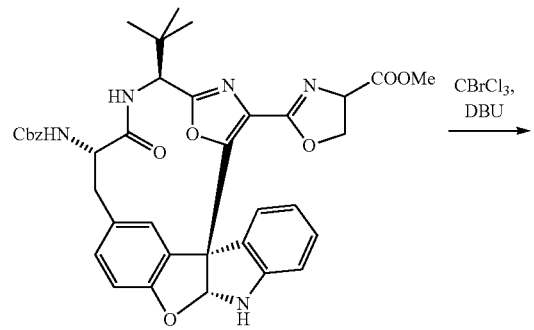

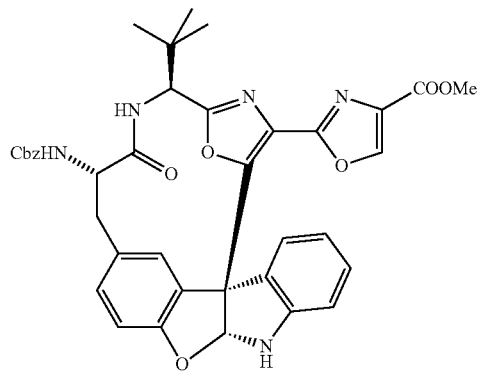

To a dry flask containing the crude product from step 8 above (2.33 mmol) were added anhydrous CH₂Cl₂ (40 ml). The mixture was cooled to 0° C. Then CBrCl₃ (0.345 ml, 3.5 mmol, 1.5 eq.) and DBU (0.523 ml, 3.5 mmol, 1.5 eq.) were added respectively. The resulting mixture was allowed to warm to room temperature and was stirred for 1 h. The reaction was monitored by LCMS. The reaction mixture was diluted with EtOAc (100 ml), washed by 10% NaHSO₄ (30 ml), water (2×30 ml), saturated aqueous NaHCO₃ (30 ml), water (30 ml) and brine (30 ml), dried over Na₂SO₄. After concentration the residue was used in next step.

Step 10

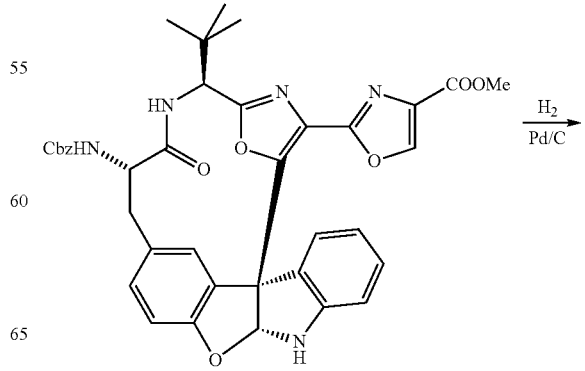

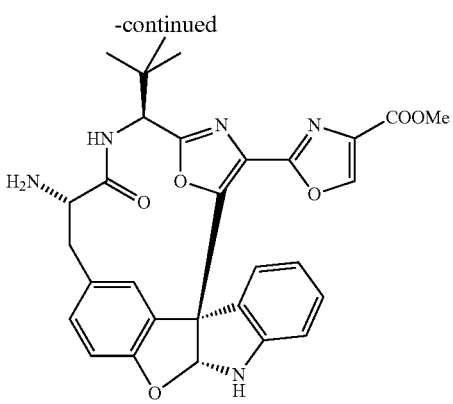

To a 50-ml flask containing material synthesized in Step 9 above (400 mg, 0.58 mmol) were added methanol (15 ml), t-butylamine (0.086 ml, 0.87 mmol, 1.5 eq.) and Pd/C (10%) (62 mg, 0.058 mmol, 0.1 eq.) under $N_2$. $H_2$ balloon was added and the flask was purged with $H_2$ for 4 times. Then $H_2$ balloon was opened to the reaction system. After 4 h stirring almost no starting material remained. The reaction was stopped. The reaction mixture was filtered through a pad of Celite and the black cake was washed with methanol (3×10 ml). The filtrate was concentrated and the residue was used in next step directly without further purification.

Step 11

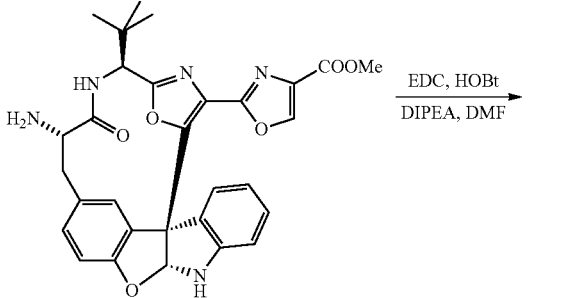

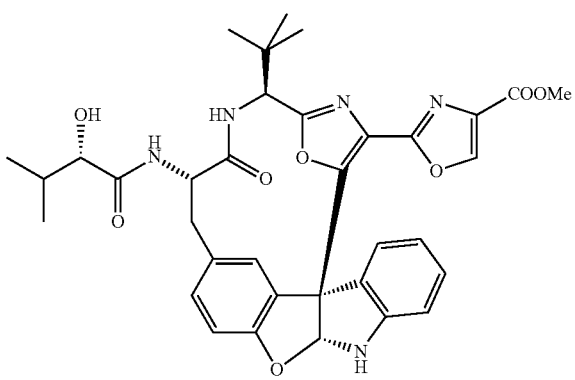

To a dry 25-ml flask containing the amine synthesized in Step 10 above (0.58 mmol) were added (S)-(+)-2-Hydroxy-3-methylbutanoic acid (82 mg, 0.696 mmol, 1.2 eq.), HOBt (94 mg, 0.696 mmol, 1.2 eq.), anhydrous DMF (8 ml) and N,N-diisopropylethylamine (0.152 ml, 0.87 mmol, 1.5 eq.). The reaction mixture was cooled to 0° C. followed by addition of EDC HCl (133 mg, 0.696 mmol, 1.2 eq.). The resulting reaction mixture was stirred at room temperature for 16 h. The reaction was monitored by LCMS. The reaction mixture was diluted with EtOAc (80 ml)/water (30 ml). The organic phase was separated and the aqueous phase was extracted by EtOAc (2×20 ml). The combined organic layers were washed by water (30 mL), 10% aqueous $NaHSO_4$ (30 ml), water (30 ml), saturated $NaHCO_3$ (30 ml), and brine (2×30 ml), and then dried over $Na_2SO_4$. After concentration, the crude was used directly in the next step.

Step 12

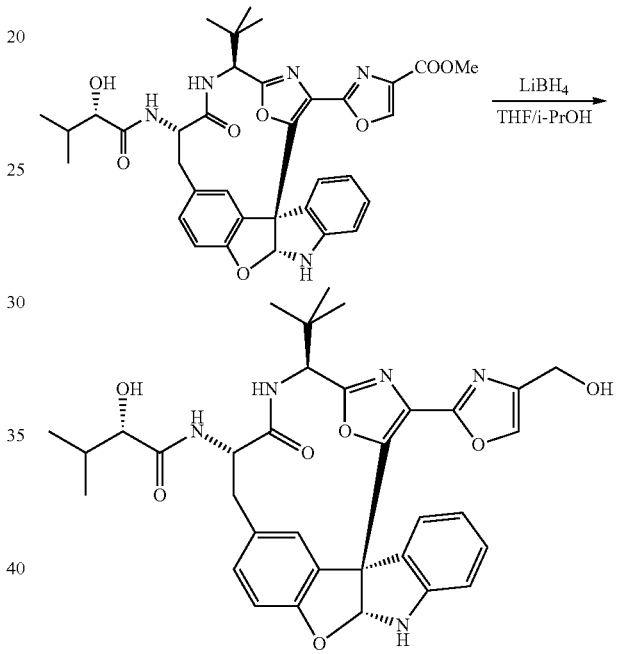

To a dry flask were added crude material synthesized in Step 11 (0.58 mmol), THF (4 ml) and 2-propanol (12 ml). This solution was cooled to 0° C. followed by addition of solid lithium borohydride (152 mg, 6.96 mmol, 12 eq.). The resulting mixture was allowed to warm to room temperature and stirred for 22 h. The reaction was monitored with LCMS. Almost no starting material remained. The reaction mixture was cooled to 0° C. 2-Propanol (24 ml) and water (40 ml) were added followed by addition of $NH_4Cl$ (3.1 g, 58 mmol, 100 eq.). The reaction mixture was stirred for 1 h and diluted with EtOAc (250 ml)/water (50 ml). The organic phase was separated and the aqueous phase was extracted by EtOAc (2×50 ml). The combined organic layers were washed by water (3×50 ml), 10% $NaHSO_4$ (2×50 ml), water (2×50 ml), saturated $NaHCO_3$ (50 ml), and brine (2×50 ml), and then dried over $Na_2SO_4$. After concentration the residue was purified by flash column chromatography (EtOAc to 10% EtOAc/MeOH) to afford desired product as an off-white solid (188 mg, 0.108 mmol, 52% for three steps). MS: m/z=627.9 (M+1).

Synthesis of Compound 81

Step 1

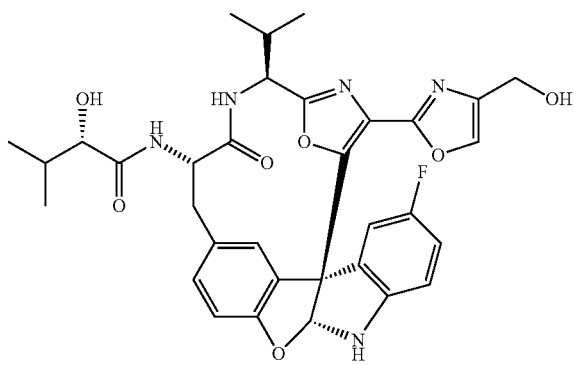

81

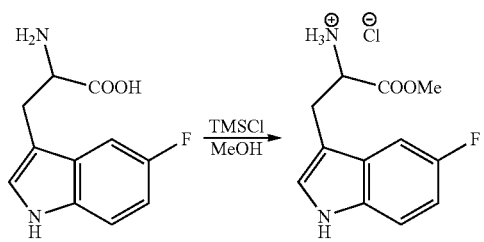 [SMILES: "TMSCl" ; "MeOH" ; NC(Cc1c[nH]c2ccc(F)cc12)C(=O)O ; COC(=O)C([NH3+])Cc1c[nH]c2ccc(F)cc12 ; [Cl-]]

Step 2

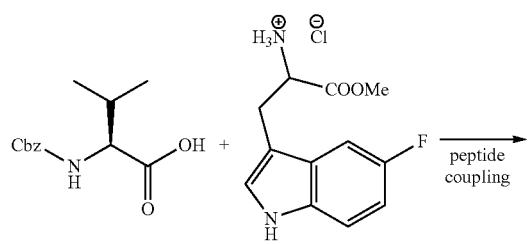

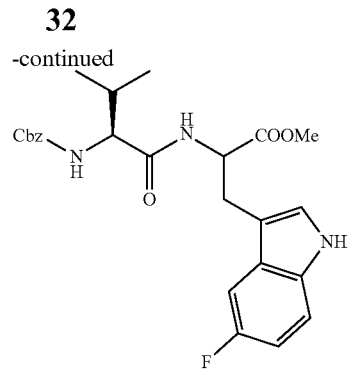

To a dry 250-ml flask with magnetic stir bar was added the amine salt synthesized in step 1 above (22.5 mmol.), Cbz-L-valine (6.22 g, 24.75 mmol, 1.1 eq.), HOB t (3.34 g, 24.75 mmol, 1.1 eq.), anhydrous DMF (80 ml) and N,N-diisopropylethylamine (11.8 ml, 67.5 mmol, 3.0 eq.). The reaction mixture was cooled to 0° C. followed by addition of EDC HCl (4.74 g, 24.75 mmol, 1.1 eq.). The resulting reaction mixture was stirred at RT for 16 h. The reaction was monitored by LCMS. Most of solvents were evaporated under reduced pressure. Then the residue was diluted with EtOAc (600 ml)/water (200 ml). The organic phase was separated and the aqueous phase was extracted by EtOAc (2×50 ml). The combined organic layers were washed by water (100 ml), 10% aqueous $NaHSO_4$ (100 ml), water (100 ml), saturated $NaHCO_3$ (100 ml), and brine (2×100 ml), and then dried over $Na_2SO_4$. After concentration, the crude was used directly in the next step.

Step 3

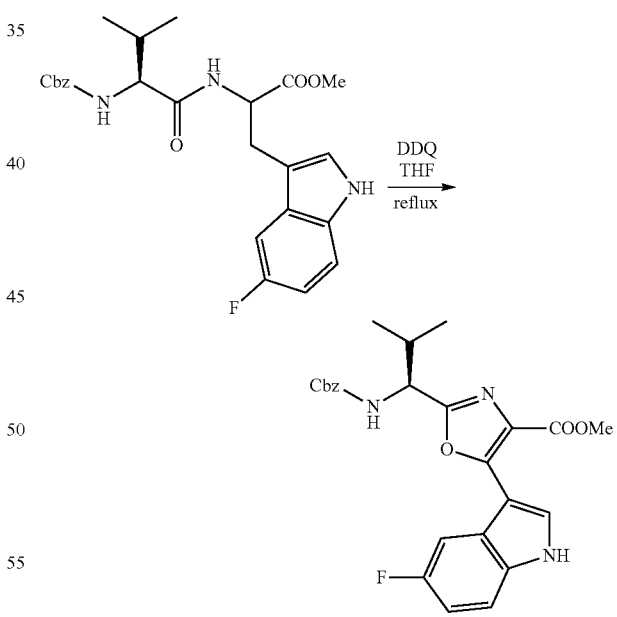

A solution of DDQ (12.8 g, 56.25 mmol, 2.5 eq.) in THF (500 ml) was added to the refluxing solution of the compound synthesized in Step 2 above (22.5 mmol) in THF (250 ml) and the dark solution was kept in reflux in an oil bath at 85° C. for 1 h. After cooling, the solvent was removed on a rotary evaporator. The residue was dissolved in ethyl acetate (600 ml), and $NaHCO_3$ (13 g) was added. The mixture was stirred for 1 h followed by filtration through a fritted funnel. The filtrate was washed by water (200 ml), aqueous saturated $NaHCO_3$ To a dry 250-ml flask were added 5-fluoro-DL-tryptophane (5.0 g, 22.5 mmol), and anhydrous methanol (120 ml). The suspension was cooled to 0° C. followed by addition of chlorotrimethyl silane (12.8 ml, 101.3 mmol, 4.5 eq.) in such a rate to keep the reaction temperature below 6° C. The resulting reaction mixture was stirred at room temperature for 20 h. The reaction was monitored by TLC. Most volatile substances were evaporated under reduced pressure. The crude was used in next step.

(2×200 ml), water (2×200 ml), brine (100 ml) and dried over Na$_2$SO$_4$. After concentration, the mixture was purified by flash column chromatography (5% EtOAc in CH$_2$Cl$_2$). This yielded 4.63 g (44.2% yield) of product.

Step 4

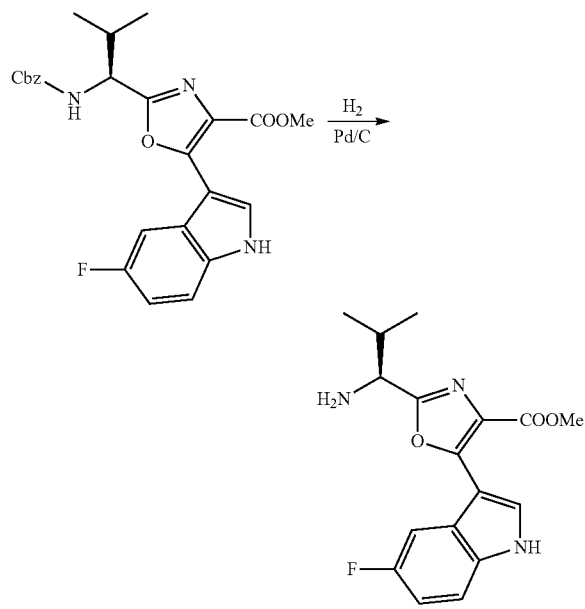

To a 250-ml flask containing material synthesized in Step 3 above (4.63 g, 9.94 mmol) was added methanol (50 ml) and Pd/C (10%) (530 mg, 0.497 mmol, 0.05 eq.) under N$_2$. H$_2$ balloon was added and the flask was purged with H$_2$ for 4 times. Then H$_2$ balloon was opened to the reaction system. After 1 h stirring almost no starting material remained. The reaction was stopped. The reaction mixture was filtered through a pad of Celite and the black cake was washed with methanol (3×15 ml). The filtrate was concentrated and the residue was used in next step directly without further purification.

Step 5

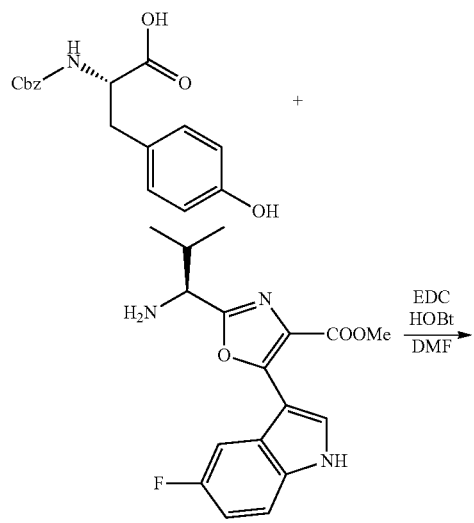

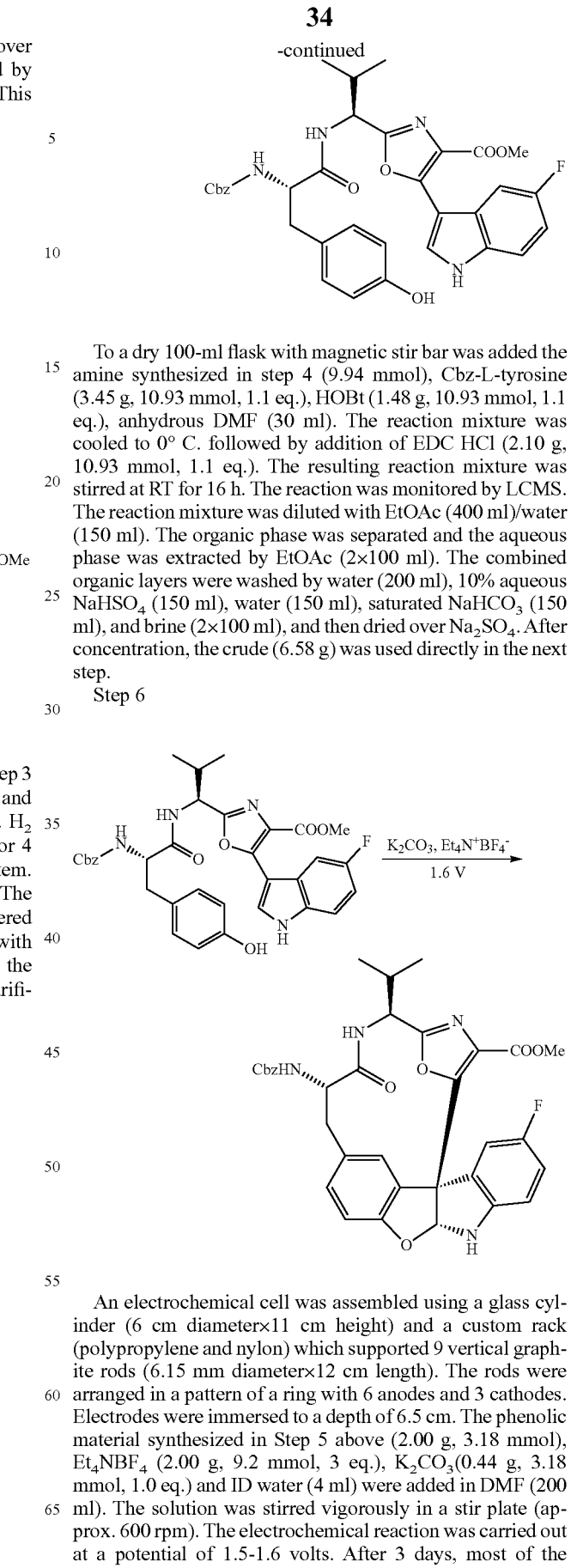

To a dry 100-ml flask with magnetic stir bar was added the amine synthesized in step 4 (9.94 mmol), Cbz-L-tyrosine (3.45 g, 10.93 mmol, 1.1 eq.), HOBt (1.48 g, 10.93 mmol, 1.1 eq.), anhydrous DMF (30 ml). The reaction mixture was cooled to 0° C. followed by addition of EDC HCl (2.10 g, 10.93 mmol, 1.1 eq.). The resulting reaction mixture was stirred at RT for 16 h. The reaction was monitored by LCMS. The reaction mixture was diluted with EtOAc (400 ml)/water (150 ml). The organic phase was separated and the aqueous phase was extracted by EtOAc (2×100 ml). The combined organic layers were washed by water (200 ml), 10% aqueous NaHSO$_4$ (150 ml), water (150 ml), saturated NaHCO$_3$ (150 ml), and brine (2×100 ml), and then dried over Na$_2$SO$_4$. After concentration, the crude (6.58 g) was used directly in the next step.

Step 6

An electrochemical cell was assembled using a glass cylinder (6 cm diameter×11 cm height) and a custom rack (polypropylene and nylon) which supported 9 vertical graphite rods (6.15 mm diameter×12 cm length). The rods were arranged in a pattern of a ring with 6 anodes and 3 cathodes. Electrodes were immersed to a depth of 6.5 cm. The phenolic material synthesized in Step 5 above (2.00 g, 3.18 mmol), Et$_4$NBF$_4$ (2.00 g, 9.2 mmol, 3 eq.), K$_2$CO$_3$ (0.44 g, 3.18 mmol, 1.0 eq.) and ID water (4 ml) were added in DMF (200 ml). The solution was stirred vigorously in a stir plate (approx. 600 rpm). The electrochemical reaction was carried out at a potential of 1.5-1.6 volts. After 3 days, most of the original SM was consumed as determined by HPLC integration at 220 nM. The electrochemistry reaction was repeated for 4 times to consume all phenolic material synthesized in step 5. The combined reaction mixtures were concentrated on a rotary evaporator (bath temp. ≤35° C.) and dried further on a vacuum manifold. The residue was diluted with EtOAc (500 ml) followed by filtration through a fritted funnel. The filtrate was washed by water (2×200 ml), brine (200 ml). The aqueous layers were extracted in succession with EtOAc (2×50 ml). The combined organic layers were dried ($Na_2SO_4$) and concentrated. This material was purified by flash column chromatography with 15% MeCN in $CH_2Cl_2$. This yielded 900 mg of desired product with 14% yield in three steps.

Step 7

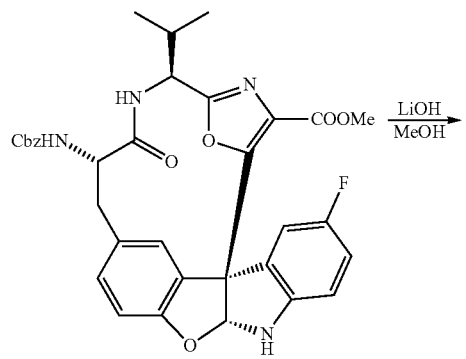

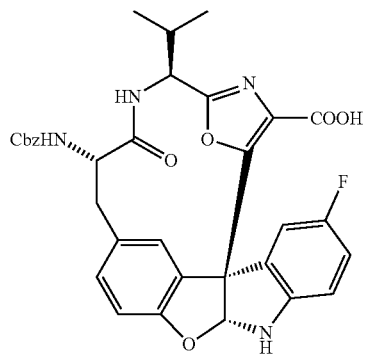

The compound synthesized in Step 6 (900 mg, 1.43 mmol) was dissolved in methanol (28 ml) and the solution was cooled in an ice bath. A solution of LiOH (344 mg, 14.3 mmol, 10 eq.) in water (4.5 ml) was added over 5 min. The ice bath was removed and the mixture was stirred at RT for 18 h. The mixture was cooled in an ice bath and water (40 ml) was added followed by 1 N aqueous HCl (14.5 ml), keeping the reaction temperature below 10° C. The mixture was partitioned between water (25 ml) and EtOAc (200 ml), and the organic layer was washed with saturated aqueous NaCl. The aqueous layers were extracted in succession with EtOAc (50 ml). The combined organic layers were dried ($Na_2SO_4$), decanted, and evaporated to give the acid product as fine white crystals.

Step 8

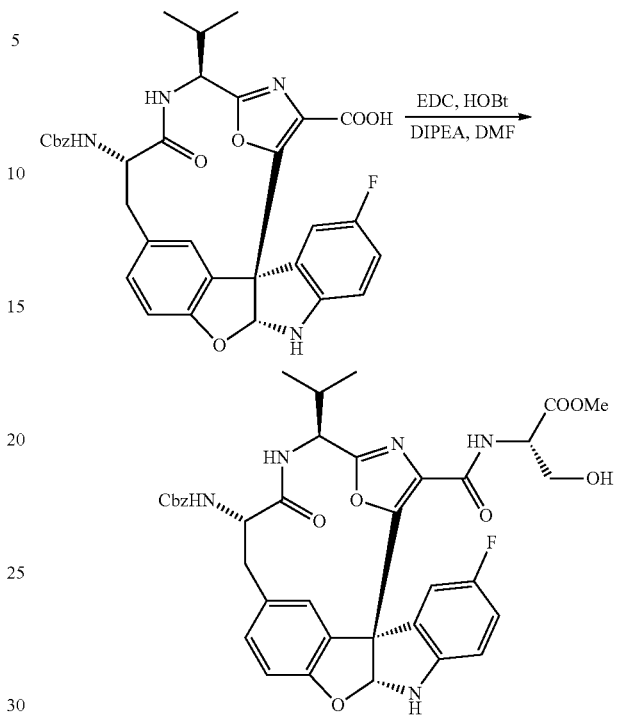

To a dry 50-ml flask with magnetic stir bar was added the carboxylic acid synthesized in step 7 above (1.43 mmol), L-serine methyl ester hydrochloride (268 mg, 1.72 mmol, 1.2 eq.), HOBt (232 mg, 1.72 mmol, 1.2 eq.), anhydrous DMF (15 ml) and N,N-diisopropylethylamine (0.624 ml, 3.58 mmol, 2.5 eq.). The reaction mixture was cooled to 0° C. followed by addition of EDC HCl (330 mg, 1.72 mmol, 1.2 eq.). The resulting reaction mixture was stirred at RT for 16 h. The reaction was monitored by LCMS. Most of solvents were evaporated under reduced pressure. The residue was diluted with EtOAc (150 ml)/water (50 ml). The organic phase was separated and the aqueous phase was extracted by EtOAc (2×30 ml). The combined organic layers were washed by water (60 ml), 10% aqueous $NaHSO_4$ (60 ml), water (60 ml), saturated $NaHCO_3$ (60 ml), and brine (2×60 ml), and then dried over $Na_2SO_4$. After concentration, the crude was used directly in the next step.

Step 9

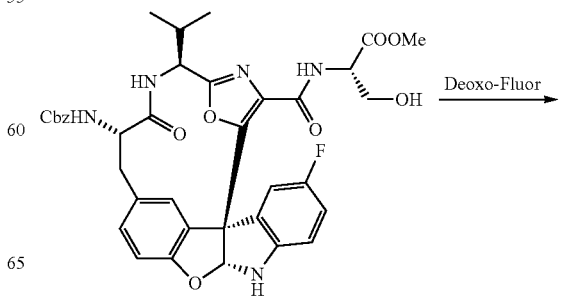

-continued

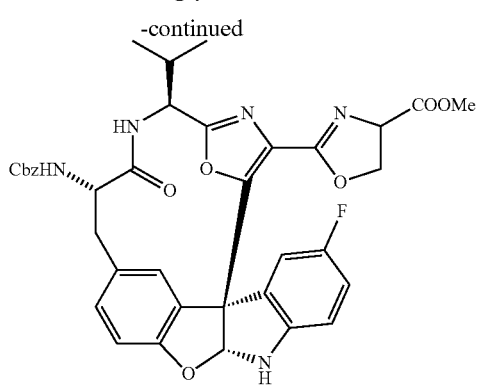

To a dry flask were added the crude product from Step 8 above (1.43 mmol) and anhydrous CH$_2$Cl$_2$ (25 ml). The reaction solution became cloudy as it was cooled to −20° C. in a dry ice/acetone/water bath. A freshly made stock solution of Bis(2-methoxyethyl)aminosulfur trifluoride (0.395 ml, 2.15 mmol, 1.5 eq.) in CH$_2$Cl$_2$ (4 ml) was added dropwise. The resulting reaction mixture was stirred at −20° C. for 1 h, and warmed to room temperature. The reaction mixture was quenched by addition of saturated aqueous NaHCO$_3$ (15 ml), diluted with EtOAc (100 ml), washed with water (2×20 ml) as well as brine (30 ml), and dried over Na$_2$SO$_4$. After concentration the residue was used in next step.

Step 10

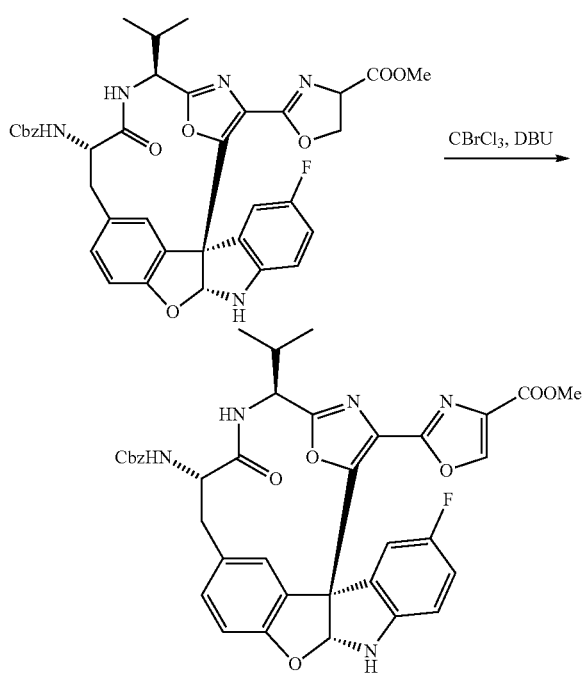

To a dry flask containing the crude product from step 9 above (1.43 mmol) were added anhydrous CH$_2$Cl$_2$ (25 ml). The mixture was cooled to 0° C. Then CBrCl$_3$ (0.211 ml, 2.15 mmol, 1.5 eq.) and DBU (0.321 ml, 2.15 mmol, 1.5 eq.) were added respectively. The resulting mixture was allowed to warm to room temperature and was stirred for 1 h. The reaction was monitored by LCMS. The reaction mixture was diluted with EtOAc (100 ml), washed by 10% NaHSO$_4$ (30 ml), water (2×30 ml), saturated aqueous NaHCO$_3$ (15 ml), water (30 ml) and brine (30 ml), dried over Na$_2$SO$_4$. After concentration the residue was used in next step.

Step 11

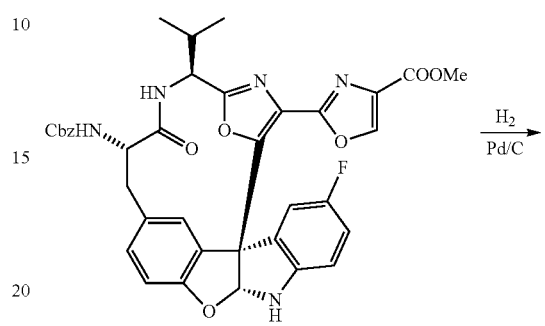

To a 100-ml flask containing material synthesized in Step 10 above (1.43 mmol) were added methanol (20 ml), t-butylamine (0.226 ml, 2.15 mmol, 1.5 eq.) and Pd/C (10%) (152 mg, 0.143 mmol, 0.1 eq.) under N$_2$. H$_2$ balloon was added and the flask was purged with H$_2$ for 4 times. Then H$_2$ balloon was opened to the reaction system. After 4 h stirring almost no starting material remained. The reaction was stopped. The reaction mixture was filtered through a pad of Celite and the black cake was washed with methanol (3×15 ml). The filtrate was concentrated and the residue was used in next step directly without further purification.

Step 12

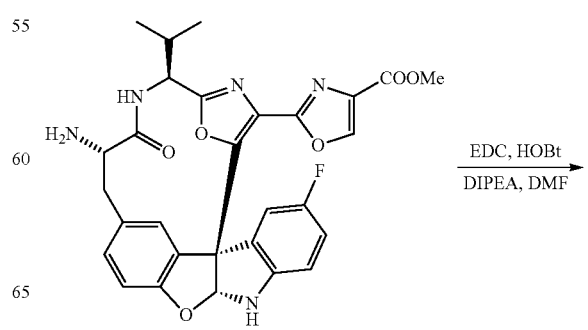

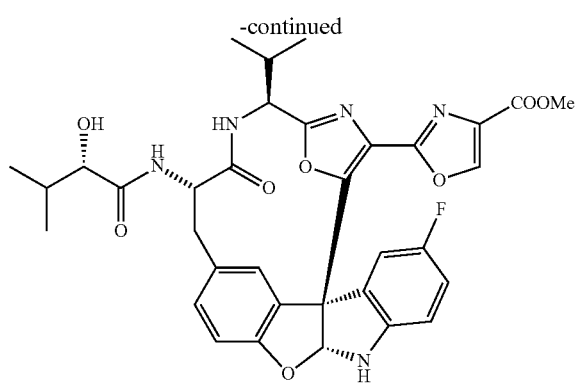

To a dry 25-ml flask containing the amine synthesized in Step 11 above (1.43 mmol) were added (S)-(+)-2-hydroxy-3-methylbutanoic acid (203 mg, 1.72 mmol, 1.2 eq.), HOBt (232 mg, 1.72 mmol, 1.2 eq.), anhydrous DMF (15 ml) and N,N-diisopropylethylamine (0.374 ml, 2.15 mmol, 1.5 eq.). The reaction mixture was cooled to 0° C. followed by addition of EDC HCl (330 mg, 1.72 mmol, 1.2 eq.). The resulting reaction mixture was stirred at room temperature for 16 h. The reaction was monitored by LCMS. The reaction mixture was diluted with EtOAc (150 ml)/water (50 ml). The organic phase was separated and the aqueous phase was extracted by EtOAc (2×30 ml). The combined organic layers were washed by water (50 ml), 10% aqueous NaHSO$_4$ (50 ml), water (30 ml), saturated NaHCO$_3$ (50 ml), and brine (2×50 ml), and then dried over Na$_2$SO$_4$. After concentration, the crude was used directly in the next step.

Step 13

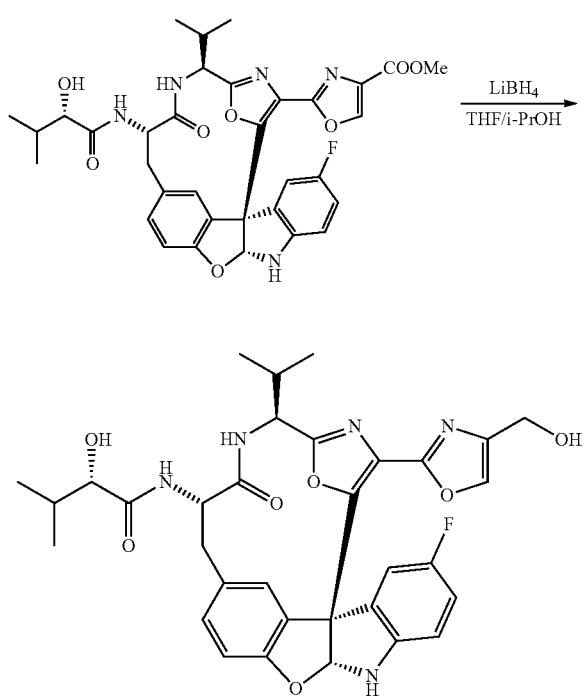

To a dry flask were added crude material synthesized in Step 12 (1.43 mmol), THF (13 ml) and 2-propanol (40 ml). This solution was cooled to 0° C. followed by addition of solid lithium borohydride (467 mg, 21.45 mmol, 15 eq.). The resulting mixture was allowed to warm to room temperature and stirred for 18 h. The reaction was monitored with LCMS. Almost no starting material remained. The reaction mixture was cooled to 0° C. 2-Propanol (40 ml) and water (80 ml) were added followed by addition of NH$_4$Cl (7.6 g, 143 mmol, 100 eq.). The reaction mixture was stirred for 1 h and diluted with EtOAc (400 ml)/water (100 ml). The organic phase was separated and the aqueous phase was extracted by EtOAc (2×100 ml). The combined organic layers were washed by water (3×100 ml), 10% NaHSO$_4$ (2×100 ml), water (2×100 ml), saturated NaHCO$_3$ (100 ml), and brine (2×100 ml), and then dried over Na$_2$SO$_4$. After concentration the residue was purified by flash column chromatography (Pure EtOAc to 7% MeCN/EtOAc) to afford desired product as an off-white solid (215 mg, 0.340 mmol, 24% for seven steps).

Synthesis of Compound 85

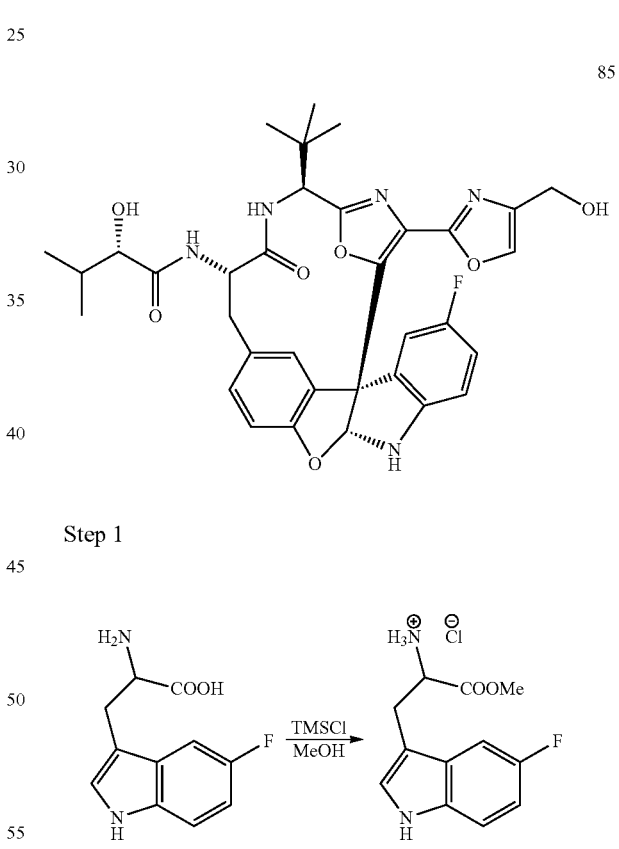

Step 1

To a dry 250-ml flask were added 5-fluoro-DL-tryptophane (6.0 g, 27.0 mmol), and anhydrous methanol (120 ml). The suspension was cooled to 0° C. followed by addition of chlorotrimethyl silane (15.4 ml, 121.5 mmol, 4.5 eq.) in such a rate to keep the reaction temperature below 6° C. The resulting reaction mixture was stirred at room temperature for 20 h. The reaction was monitored by TLC. Most volatile substances were evaporated under reduced pressure. The crude was used in next step.

Step 2

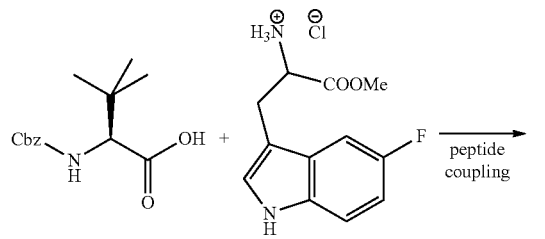

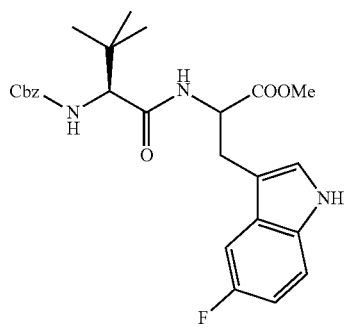

To a dry 250-ml flask with magnetic stir bar was added the amine salt synthesized in step 1 above (27 mmol.), Cbz-L-α-t-butylglycine DCHA salt (13.26 g, 29.7 mmol, 1.1 eq.), HOBt (4.01 g, 29.7 mmol, 1.1 eq.), anhydrous DMF (100 ml) and N,N-diisopropylethylamine (14.1 ml, 81 mmol, 3.0 eq.). The reaction mixture was cooled to 0° C. followed by addition of EDC HCl (5.69 g, 29.7 mmol, 1.1 eq.). The resulting reaction mixture was stirred at RT for 16 h. The reaction was monitored by LCMS. Most of solvents were evaporated under reduced pressure. Then the residue was diluted with EtOAc (700 ml)/water (200 ml). The organic phase was separated and the aqueous phase was extracted by EtOAc (2×50 ml). The combined organic layers were washed by water (100 ml), 10% aqueous NaHSO₄ (100 ml), water (100 ml), saturated NaHCO₃ (100 ml), and brine (2×100 ml), and then dried over Na₂SO₄. After concentration, the crude was used directly in the next step.

Step 3

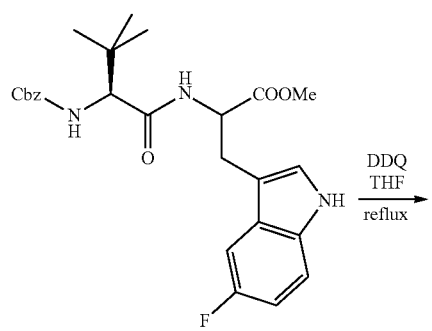

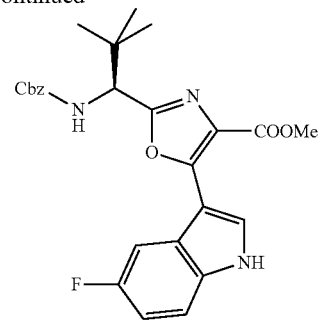

A solution of DDQ (15.32 g, 67.5 mmol, 2.5 eq.) in THF (100 ml) was added to the refluxing solution of the compound synthesized in Step 2 above (27 mmol) in THF (300 ml) and the dark solution was kept in reflux in an oil bath at 85° C. for 1 h. After cooling, the solvent was removed on a rotary evaporator. The residue was dissolved in ethyl acetate (700 ml), and NaHCO₃ (15 g) was added. The mixture was stirred for 1 h followed by filtration through a fritted funnel. The filtrate was washed by water (200 ml), aqueous saturated NaHCO₃ (2×200 ml), water (2×200 ml), brine (100 ml) and dried over Na₂SO₄. After concentration, the mixture was purified by flash column chromatography (5% EtOAc in CH₂Cl₂). This yielded 6.42 g (50% yield) of product.

Step 4

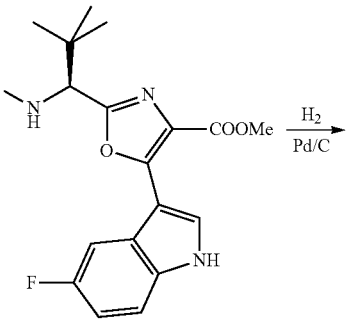

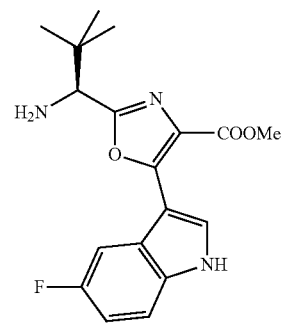

To a 250-ml flask containing material synthesized in Step 3 above (6.42 g, 13.4 mmol) was added methanol (60 ml) and Pd/C (10%) (1.43 g, 1.34 mmol, 0.1 eq.) under N₂. H₂ balloon was added and the flask was purged with H₂ for 4 times. Then H₂ balloon was opened to the reaction system. After 1 h stirring almost no starting material remained. The reaction was stopped. The reaction mixture was filtered through a pad of Celite and the black cake was washed with methanol (3×15 ml). The filtrate was concentrated and the residue was used in next step directly without further purification.

Step 5

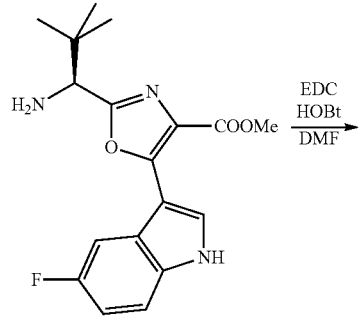

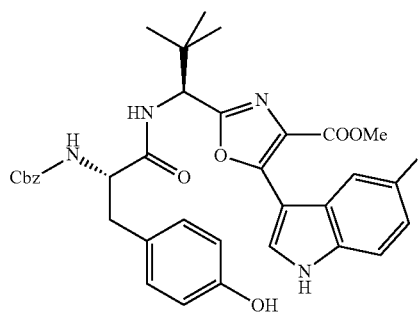

To a dry 100-ml flask with magnetic stir bar was added the amine synthesized in step 4 (13.4 mmol), Cbz-L-tyrosine (4.65 g, 14.74 mmol, 1.1 eq.), HOBt (2.0 g, 14.74 mmol, 1.1 eq.), anhydrous DMF (40 ml). The reaction mixture was cooled to 0° C. followed by addition of EDC HCl (2.83 g, 14.74 mmol, 1.1 eq.). The resulting reaction mixture was stirred at RT for 16 h. The reaction was monitored by LCMS. The reaction mixture was diluted with EtOAc (500 ml)/water (150 ml). The organic phase was separated and the aqueous phase was extracted by EtOAc (2×100 ml). The combined organic layers were washed by water (200 ml), 10% aqueous NaHSO$_3$ (150 ml), water (150 ml), saturated NaHCO$_3$ (150 ml), and brine (2×100 ml), and then dried over Na$_2$SO$_4$. After concentration, the crude was used directly in the next step.

Step 6

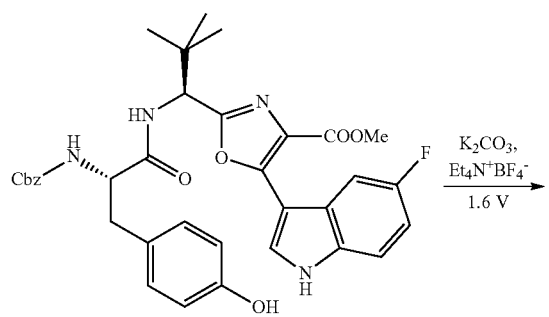

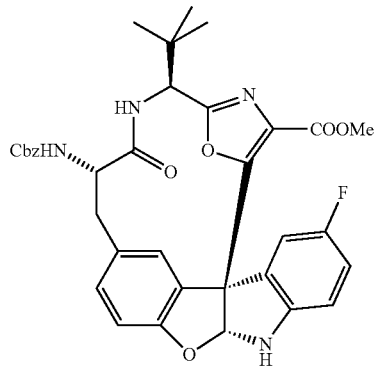

An electrochemical cell was assembled using a glass cylinder (6 cm diameter×11 cm height) and a custom rack (polypropylene and nylon) which supported 9 vertical graphite rods (6.15 mm diameter×12 cm length). The rods were arranged in a pattern of a ring with 6 anodes and 3 cathodes. Electrodes were immersed to a depth of 6.5 cm. The phenolic material synthesized in Step 5 above (2.00 g, 3.11 mmol), Et$_4$NBF$_4$ (2.00 g, 9.2 mmol, 3 eq.), K$_2$CO$_3$ (0.409 g, 2.96 mmol, 0.95 eq.) and ID water (4 ml) were added in DMF (200 ml). The solution was stirred vigorously in a stir plate (approx. 600 rpm). The electrochemical reaction was carried out at a potential of 1.5-1.6 volts. After 3 days, most of the original SM was consumed as determined by HPLC integration at 220 nM. The electrochemistry reaction was repeated for 4 times to consume all phenolic material synthesized in step 5. The combined reaction mixtures were concentrated on a rotary evaporator (bath temp. ≤35° C.) and dried further on a vacuum manifold. The residue was diluted with EtOAc (500 ml) followed by filtration through a fritted funnel. The filtrate was washed by water (2×200 ml) brine (200 ml). The aqueous layers were extracted in succession with EtOAc (2×50 ml). The combined organic layers were dried (Na$_2$SO$_4$) and concentrated. This material was purified by flash column chromatography with 15% MeCN in CH$_2$Cl$_2$. This yielded 553 mg of desired product with 6.4% yield in three steps.

Step 7

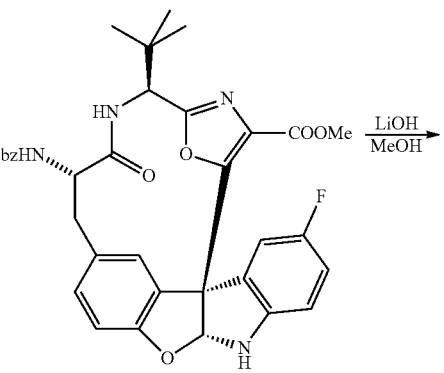

-continued

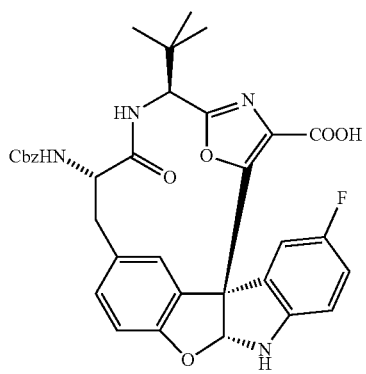

The compound synthesized in Step 6 (553 mg, 0.863 mmol) was dissolved in methanol (17 ml) and the solution was cooled in an ice bath. A solution of LiOH (207 mg, 8.63 mmol, 10 eq.) in water (2.7 ml) was added over 5 min. The ice bath was removed and the mixture was stirred at RT for 18 h. The mixture was cooled in an ice bath and water (20 ml) was added followed by 1 N aqueous HCl (8.8 ml), keeping the reaction temperature below 10° C. The mixture was partitioned between water (15 ml) and EtOAc (100 ml), and the organic layer was washed with saturated aqueous NaCl. The aqueous layers were extracted in succession with EtOAc (30 ml). The combined organic layers were dried (Na$_2$SO$_4$), decanted, and evaporated to give the acid product as fine white crystals.

Step 8

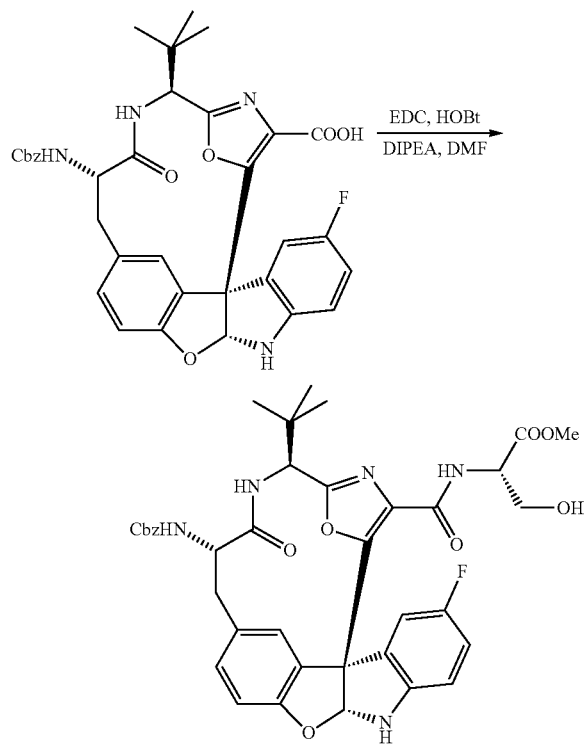

To a dry 50-ml flask with magnetic stir bar was added the carboxylic acid synthesized in step 7 above (0.863 mmol), L-serine methyl ester hydrochloride (161 mg, 1.036 mmol, 1.2 eq.), HOBt (140 mg, 1.036 mmol, 1.2 eq.), anhydrous DMF (15 ml) and N,N-diisopropylethylamine (0.346 ml, 1.99 mmol, 2.3 eq.). The reaction mixture was cooled to 0° C. followed by addition of EDC HCl (199 mg, 1.036 mmol, 1.3 eq.). The resulting reaction mixture was stirred at RT for 16 h. The reaction was monitored by LCMS. Most of solvents were evaporated under reduced pressure. The residue was diluted with EtOAc (100 ml)/water (30 ml). The organic phase was separated and the aqueous phase was extracted by EtOAc (2×20 ml). The combined organic layers were washed by water (40 ml), 10% aqueous NaHSO$_4$ (40 ml), water (40 ml), saturated NaHCO$_3$ (40 ml), and brine (2×40 ml), and then dried over Na$_2$SO$_4$. After concentration, the crude was used directly in the next step.

Step 9

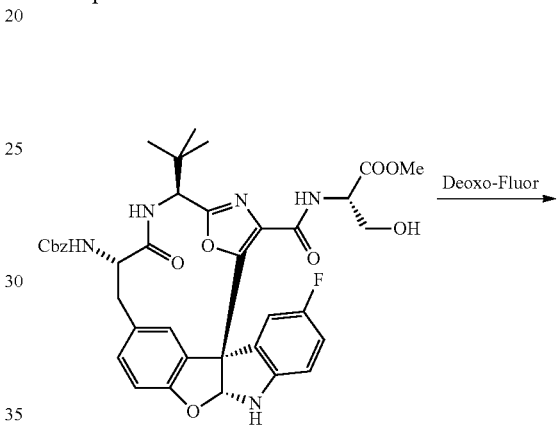

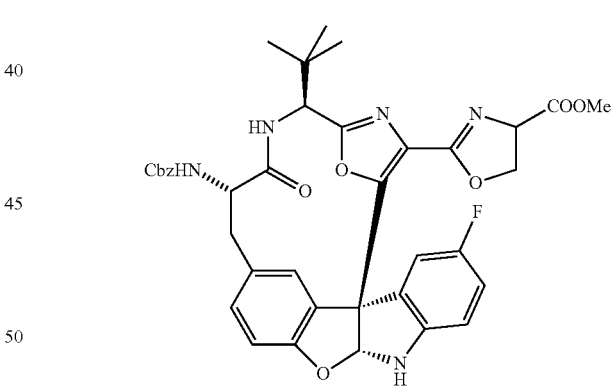

To a dry flask were added the crude product from Step 8 above (0.863 mmol) and anhydrous CH$_2$Cl$_2$ (15 ml). The reaction solution became cloudy as it was cooled to −20° C. in a dry ice/acetone/water bath. A freshly made stock solution of Bis(2-methoxyethyl)aminosulfur trifluoride (0.239 ml, 1.29 mmol, 1.5 eq.) in CH$_2$Cl$_2$ (2 ml) was added dropwise. The resulting reaction mixture was stirred at −20° C. for 1 h, and warmed to room temperature. The reaction mixture was quenched by addition of saturated aqueous NaHCO$_3$ (10 ml), diluted with EtOAc (50 ml), washed with water (2×15 ml) as well as brine (20 ml), and dried over Na$_2$SO$_4$. After concentration the residue was used in next step.

Step 10

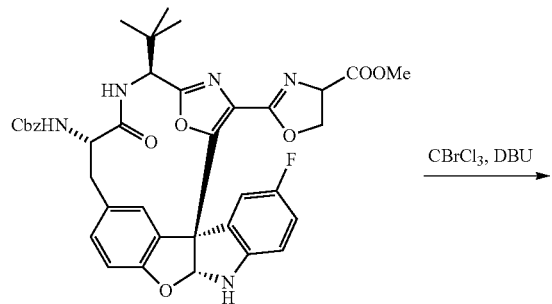

CBrCl₃, DBU

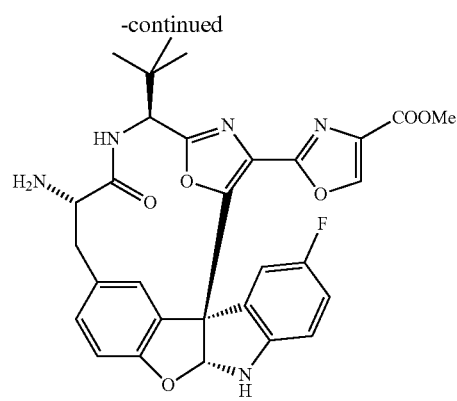

-continued

To a 50-ml flask containing material synthesized in Step 10 above (0.863 mmol) were added methanol (12 ml), t-butylamine (0.137 ml, 1.3 mmol, 1.5 eq.) and Pd/C (10%) (91 mg, 0.0863 mmol, 0.1 eq.) under N₂. H₂ balloon was added and the flask was purged with H₂ for 4 times. Then H₂ balloon was opened to the reaction system. After 4 h stirring almost no starting material remained. The reaction was stopped. The reaction mixture was filtered through a pad of Celite and the black cake was washed with methanol (3×10 ml). The filtrate was concentrated and the residue was used in next step directly without further purification.

Step 12

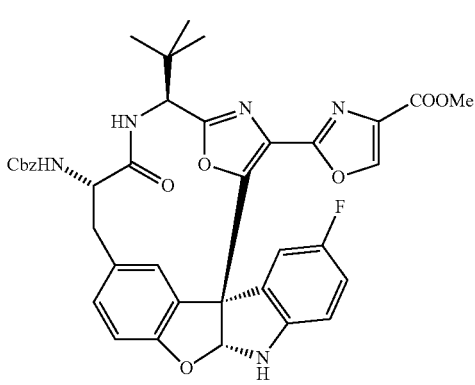

To a dry flask containing the crude product from step 9 above (0.866 mmol) were added anhydrous CH₂Cl₂ (15 ml). The mixture was cooled to 0° C. Then CBrCl₃ (0.128 ml, 1.29 mmol, 1.5 eq.) and DBU (0.193 ml, 1.29 mmol, 1.5 eq.) were added respectively. The resulting mixture was allowed to warm to room temperature and was stirred for 1 h. The reaction was monitored by LCMS. The reaction mixture was diluted with EtOAc (50 ml), washed by 10% NaHSO₄ (15 ml), water (2×15 ml), saturated aqueous NaHCO₃ (15 ml), water (15 ml) and brine (15 ml), dried over Na₂SO₄. After concentration the residue was used in next step.

Step 11

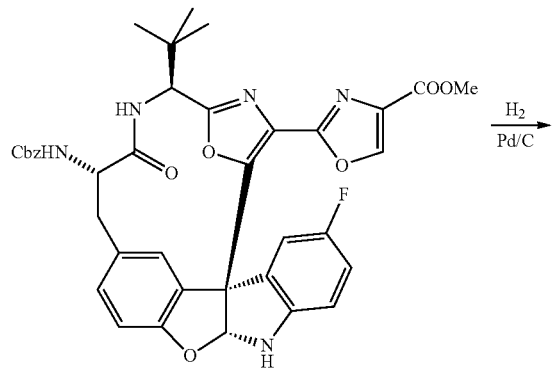

H₂
Pd/C

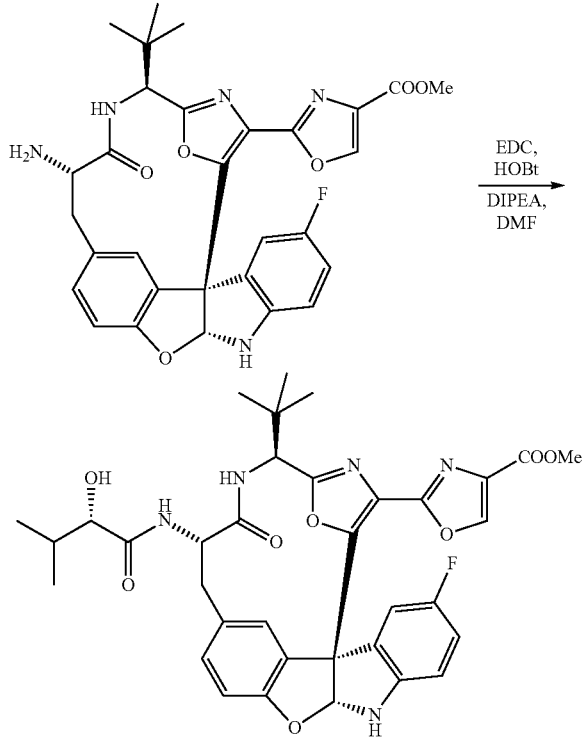

EDC, HOBt
DIPEA, DMF

To a dry 25-ml flask containing the amine synthesized in Step 11 above (0.863 mmol) were added (S)-(+)-2-hydroxy-3-methylbutanoic acid (122 mg, 1.036 mmol, 1.2 eq.), HOBt (140 mg, 1.036 mmol, 1.2 eq.), anhydrous DMF (10 ml) and N,N-diisopropylethylamine (0.225 ml, 1.29 mmol, 1.5 eq.). The reaction mixture was cooled to 0° C. followed by addition of EDC HCl (199 mg, 1.036 mmol, 1.2 eq.). The resulting reaction mixture was stirred at room temperature for 16 h. The reaction was monitored by LCMS. The reaction mixture was diluted with EtOAc (100 ml)/water (30 ml). The organic phase was separated and the aqueous phase was extracted by EtOAc (2×20 ml). The combined organic layers were washed by water (30 ml), 10% aqueous $NaHSO_4$ (30 ml), water (30 ml), saturated $NaHCO_3$ (30 ml), and brine (2×30 ml), and then dried over $Na_2SO_4$. After concentration, the crude was used directly in the next step.

Step 13

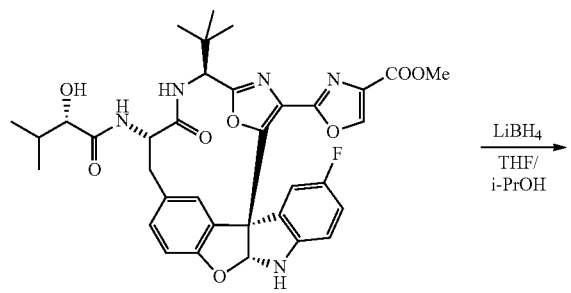

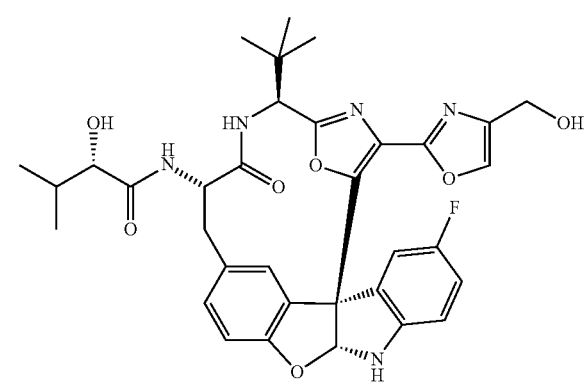

To a dry flask were added crude material synthesized in Step 12 (0.863 mmol), THF (10 ml) and 2-propanol (30 ml). This solution was cooled to 0° C. followed by addition of solid lithium borohydride (282 mg, 12.95 mmol, 15 eq.). The resulting mixture was allowed to warm to room temperature and stirred for 22 h. The reaction was monitored with LCMS. Almost no starting material remained. The reaction mixture was cooled to 0° C. 2-Propanol (24 ml) and water (40 ml) were added followed by addition of $NH_4Cl$ (4.6 g, 86.3 mmol, 100 eq.). The reaction mixture was stirred for 1 h and diluted with EtOAc (250 ml)/water (50 ml). The organic phase was separated and the aqueous phase was extracted by EtOAc (2×50 ml). The combined organic layers were washed by water (3×100 ml), 10% $NaHSO_4$ (2×100 ml), water (2×100 ml), saturated $NaHCO_3$ (100 ml), and brine (2×100 ml), and then dried over $Na_2SO_4$. After concentration the residue was purified by flash column chromatography (70% EtOAc/DCM) to afford desired product as an off-white solid (124 mg, 0.192 mmol, 22% for seven steps).

Synthesis of Compound 86

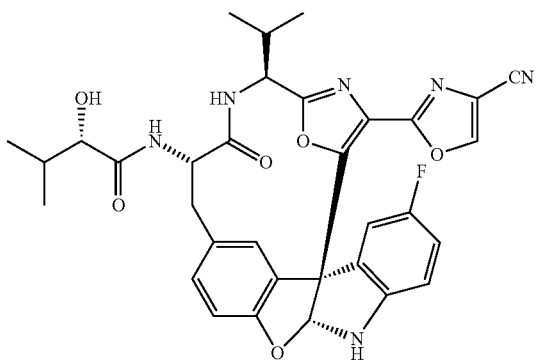

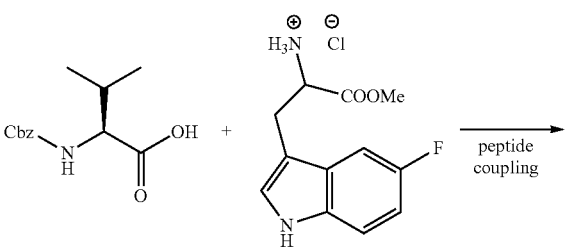

To a dry 250-ml flask were added 5-fluoro-DL-tryptophane (5.0 g, 22.5 mmol), and anhydrous methanol (120 ml). The suspension was cooled to 0° C. followed by addition of chlorotrimethyl silane (12.8 ml, 101.3 mmol, 4.5 eq.) in such a rate to keep the reaction temperature below 6° C. The resulting reaction mixture was stirred at room temperature for 20 h. The reaction was monitored by TLC. Most volatile substances were evaporated under reduced pressure. The crude was used in next step.

Step 2

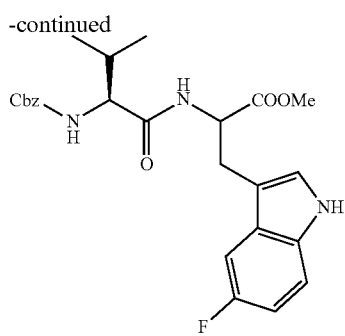

To a dry 250-ml flask with magnetic stir bar was added the amine salt synthesized in step 1 above (22.5 mmol.), Cbz-L-valine (6.22 g, 24.75 mmol, 1.1 eq.), HOBt (3.34 g, 24.75 mmol, 1.1 eq.), anhydrous DMF (80 ml) and N,N-diisopropylethylamine (11.8 ml, 67.5 mmol, 3.0 eq.). The reaction mixture was cooled to 0° C. followed by addition of EDC HCl (4.74 g, 24.75 mmol, 1.1 eq.). The resulting reaction mixture was stirred at RT for 16 h. The reaction was monitored by LCMS. Most of solvents were evaporated under reduced pressure. Then the residue was diluted with EtOAc (600 ml)/water (200 ml). The organic phase was separated and the aqueous phase was extracted by EtOAc (2×50 ml). The combined organic layers were washed by water (100 ml), 10% aqueous NaHSO$_4$ (100 ml), water (100 ml), saturated NaHCO$_3$ (100 ml), and brine (2×100 ml), and then dried over Na$_2$SO$_4$. After concentration, the crude was used directly in the next step.

Step 3

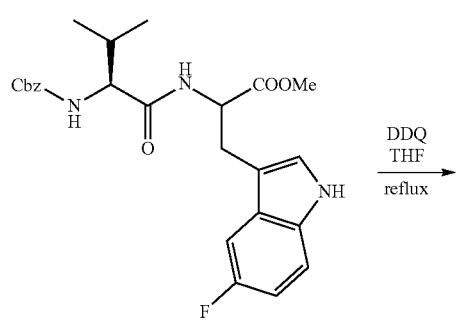

A solution of DDQ (12.8 g, 56.25 mmol, 2.5 eq.) in THF (500 ml) was added to the refluxing solution of the compound synthesized in Step 2 above (22.5 mmol) in THF (250 ml) and the dark solution was kept in reflux in an oil bath at 85° C. for 1 h. After cooling, the solvent was removed on a rotary evaporator. The residue was dissolved in ethyl acetate (600 ml), and NaHCO$_3$ (13 g) was added. The mixture was stirred for 1 h followed by filtration through a fritted funnel. The filtrate was washed by water (200 ml), aqueous saturated NaHCO$_3$ (2×200 ml), water (2×200 ml), brine (100 ml) and dried over Na$_2$SO$_4$. After concentration, the mixture was purified by flash column chromatography (5% EtOAc in CH$_2$Cl$_2$). This yielded 4.63 g (44.2% yield) of product.

Step 4

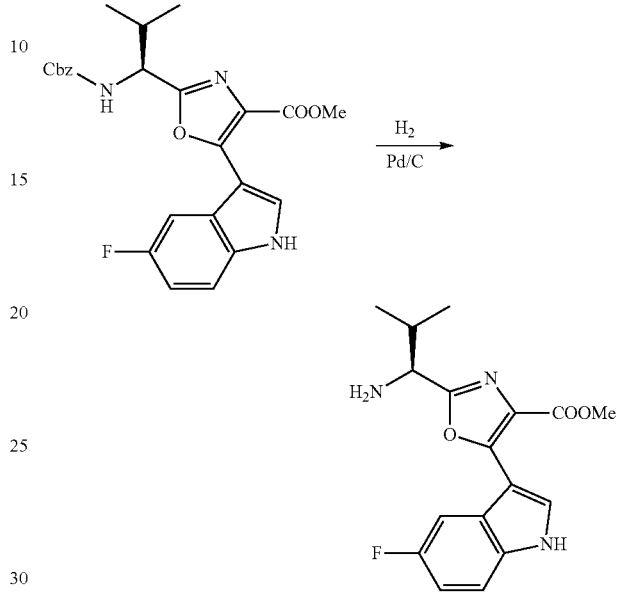

To a 250-ml flask containing material synthesized in Step 3 above (4.63 g, 9.94 mmol) was added methanol (50 ml) and Pd/C (10%) (530 mg, 0.497 mmol, 0.05 eq.) under N$_2$. H$_2$ balloon was added and the flask was purged with H$_2$ for 4 times. Then H$_2$ balloon was opened to the reaction system. After 1 h stirring almost no starting material remained. The reaction was stopped. The reaction mixture was filtered through a pad of Celite and the black cake was washed with methanol (3×15 ml). The filtrate was concentrated and the residue was used in next step directly without further purification.

Step 5

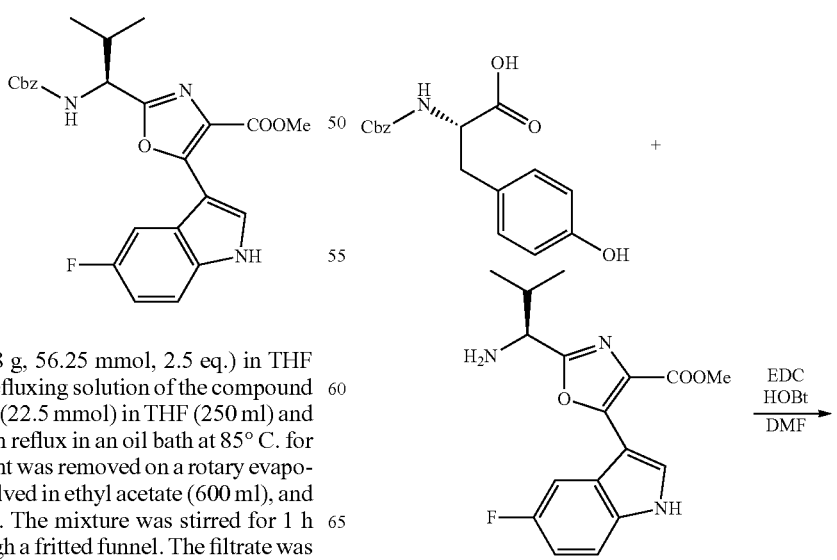

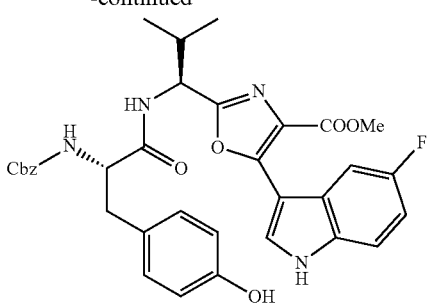

To a dry 100-ml flask with magnetic stir bar was added the amine synthesized in step 4 (9.94 mmol), Cbz-L-tyrosine (3.45 g, 10.93 mmol, 1.1 eq.), HOBt (1.48 g, 10.93 mmol, 1.1 eq.), anhydrous DMF (30 ml). The reaction mixture was cooled to 0° C. followed by addition of EDC HCl (2.10 g, 10.93 mmol, 1.1 eq.). The resulting reaction mixture was stirred at RT for 16 h. The reaction was monitored by LCMS. The reaction mixture was diluted with EtOAc (400 ml)/water (150 ml). The organic phase was separated and the aqueous phase was extracted by EtOAc (2×100 ml). The combined organic layers were washed by water (200 ml), 10% aqueous NaHSO$_4$ (150 ml), water (150 ml), saturated NaHCO$_3$ (150 ml), and brine (2×100 ml), and then dried over Na$_2$SO$_4$. After concentration, the crude (6.58 g) was used directly in the next step.

Step 6

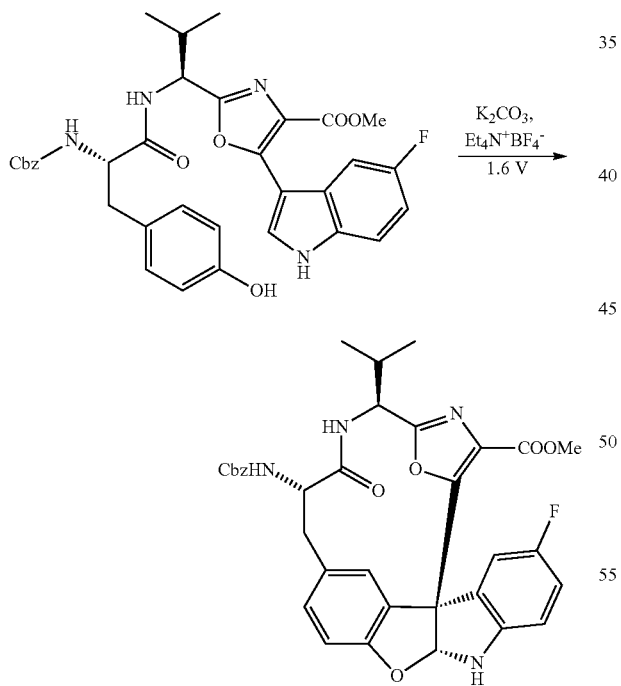

An electrochemical cell was assembled using a glass cylinder (6 cm diameter×11 cm height) and a custom rack (polypropylene and nylon) which supported 9 vertical graphite rods (6.15 mm diameter×12 cm length). The rods were arranged in a pattern of a ring with 6 anodes and 3 cathodes. Electrodes were immersed to a depth of 6.5 cm. The phenolic material synthesized in Step 5 above (2.00 g, 3.18 mmol), Et$_4$NBF$_4$ (2.00 g, 9.2 mmol, 3 eq.), K$_2$CO$_3$ (0.44 g, 3.18 mmol, 1.0 eq.) and ID water (4 ml) were added in DMF (200 ml). The solution was stirred vigorously in a stir plate (approx. 600 rpm). The electrochemical reaction was carried out at a potential of 1.5-1.6 volts. After 3 days, most of the original SM was consumed as determined by HPLC integration at 220 nM. The electrochemistry reaction was repeated for 4 times to consume all phenolic material synthesized in step 5. The combined reaction mixtures were concentrated on a rotary evaporator (bath temp. ≤35° C.) and dried further on a vacuum manifold. The residue was diluted with EtOAc (500 ml) followed by filtration through a fritted funnel. The filtrate was washed by water (2×200 ml), brine (200 ml). The aqueous layers were extracted in succession with EtOAc (2×50 ml). The combined organic layers were dried (Na$_2$SO$_4$) and concentrated. This material was purified by flash column chromatography with 15% MeCN in CH$_2$Cl$_2$. This yielded 900 mg of desired product with 14% yield in three steps.

Step 7

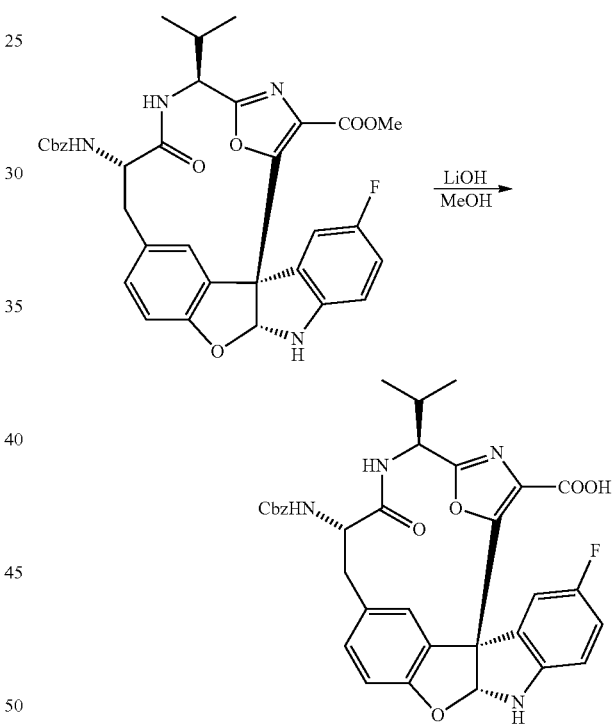

The compound synthesized in Step 6 (900 mg, 1.43 mmol) was dissolved in methanol (28 ml) and the solution was cooled in an ice bath. A solution of LiOH (344 mg, 14.3 mmol, 10 eq.) in water (4.5 ml) was added over 5 min. The ice bath was removed and the mixture was stirred at RT for 18 h. The mixture was cooled in an ice bath and water (40 ml) was added followed by 1 N aqueous HCl (14.5 ml), keeping the reaction temperature below 10° C. The mixture was partitioned between water (25 ml) and EtOAc (200 ml), and the organic layer was washed with saturated aqueous NaCl. The aqueous layers were extracted in succession with EtOAc (50 ml). The combined organic layers were dried (Na$_2$SO$_4$), decanted, and evaporated to give the acid product as fine white crystals.

Step 8

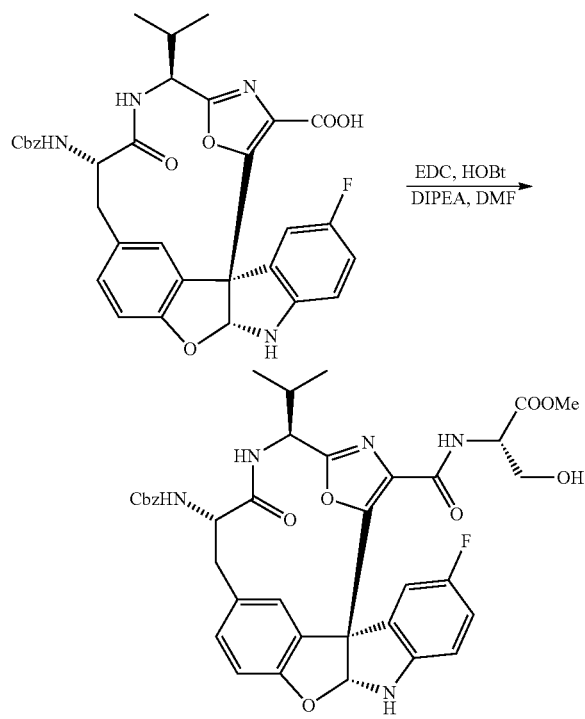

To a dry 50-ml flask with magnetic stir bar was added the carboxylic acid synthesized in step 7 above (1.43 mmol), L-serine methyl ester hydrochloride (268 mg, 1.72 mmol, 1.2 eq.), HOBt (232 mg, 1.72 mmol, 1.2 eq.), anhydrous DMF (15 ml) and N,N-diisopropylethylamine (0.624 ml, 3.58 mmol, 2.5 eq.). The reaction mixture was cooled to 0° C. followed by addition of EDC HCl (330 mg, 1.72 mmol, 1.2 eq.). The resulting reaction mixture was stirred at RT for 16 h. The reaction was monitored by LCMS. Most of solvents were evaporated under reduced pressure. The residue was diluted with EtOAc (150 ml)/water (50 ml). The organic phase was separated and the aqueous phase was extracted by EtOAc (2×30 ml). The combined organic layers were washed by water (60 ml), 10% aqueous NaHSO$_4$ (60 ml), water (60 ml), saturated NaHCO$_3$ (60 ml), and brine (2×60 ml), and then dried over Na$_2$SO$_4$. After concentration, the crude was used directly in the next step.

Step 9

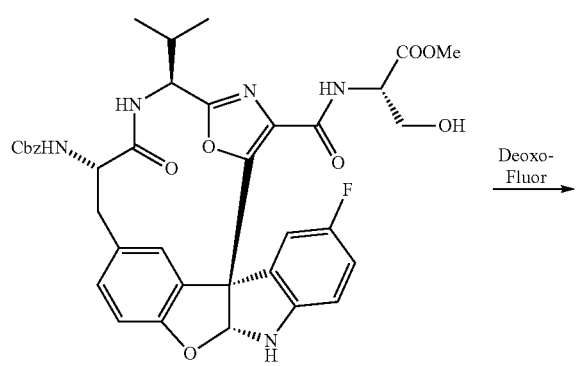

-continued

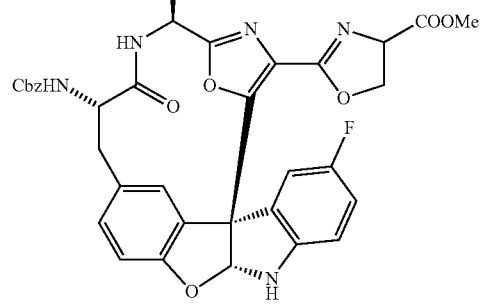

To a dry flask were added the crude product from Step 8 above (1.43 mmol) and anhydrous CH$_2$Cl$_2$ (25 ml). The reaction solution became cloudy as it was cooled to −20° C. in a dry ice/acetone/water bath. A freshly made stock solution of Bis(2-methoxyethyl)aminosulfur trifluoride (0.395 ml, 2.15 mmol, 1.5 eq.) in CH$_2$Cl$_2$ (4 ml) was added dropwise. The resulting reaction mixture was stirred at −20° C. for 1 h, and warmed to room temperature. The reaction mixture was quenched by addition of saturated aqueous NaHCO$_3$ (15 ml), diluted with EtOAc (100 ml), washed with water (2×20 ml) as well as brine (30 ml), and dried over Na$_2$SO$_4$. After concentration the residue was used in next step.

Step 10

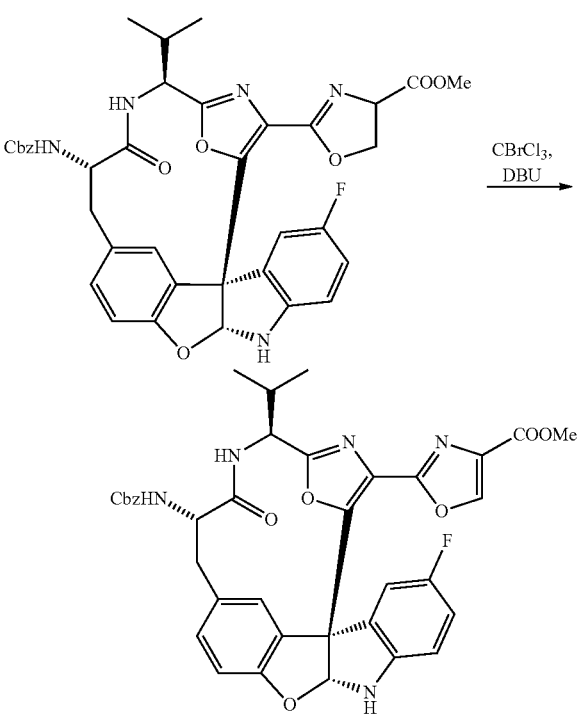

To a dry flask containing the crude product from step 9 above (1.43 mmol) were added anhydrous CH$_2$Cl$_2$ (25 ml). The mixture was cooled to 0° C. Then CBrCl$_3$ (0.211 ml, 2.15 mmol, 1.5 eq.) and DBU (0.321 ml, 2.15 mmol, 1.5 eq.) were added respectively. The resulting mixture was allowed to warm to room temperature and was stirred for 1 h. The reaction was monitored by LCMS. The reaction mixture was diluted with EtOAc (100 ml), washed by 10% NaHSO$_4$ (30 ml), water (2×30 ml), saturated aqueous NaHCO₃ (15 ml), water (30 ml) and brine (30 ml), dried over Na₂SO₄. After concentration the residue was used in next step.

Step 11

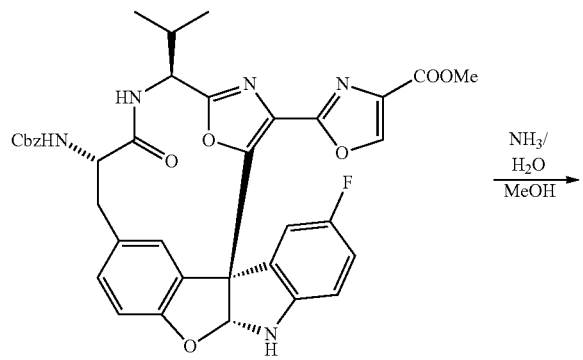

To a flask were added the product from step 10 (0.735 mmol), methanol (30 ml), aqueous ammonia solution (28%, 15 ml). The resulting reaction mixture was stirred at room temperature for 24 hrs. The reaction was monitored by TLC. Most of methanol was evaporated under reduced pressure. The residue was extracted by ethyl acetate (3×30 ml), washed with 2% NaHSO₄ (30 ml), water (30 ml), 5% NaHCO₃ (30 ml), brine (30 ml). The organic phase was dried over Na₂SO₄. After concentration, the crude was used in next step.

Step 12

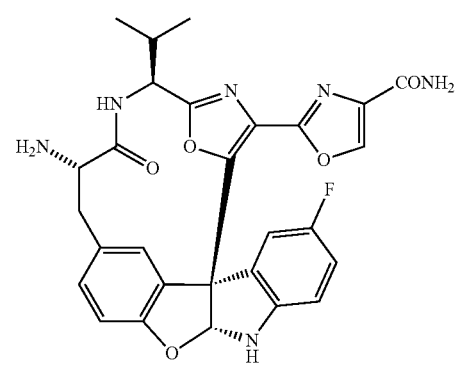

-continued

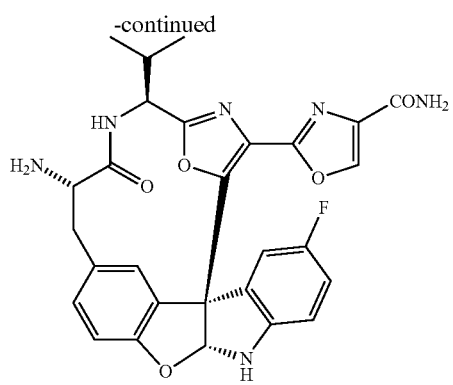

To a 100-ml flask containing material synthesized in Step 11 above (0.735 mmol) were added methanol (20 ml), t-butylamine (0.116 ml, 1.1 mmol, 1.5 eq.) and Pd/C (10%) (78 mg, 0.052 mmol, 0.1 eq.) under N₂. H₂ balloon was added and the flask was purged with H₂ for 4 times. Then H₂ balloon was opened to the reaction system. After 4 h stirring almost no starting material remained. The reaction was stopped. The reaction mixture was filtered through a pad of Celite and the black cake was washed with methanol (3×15 ml). The filtrate was concentrated and the residue was used in next step directly without further purification.

Step 13

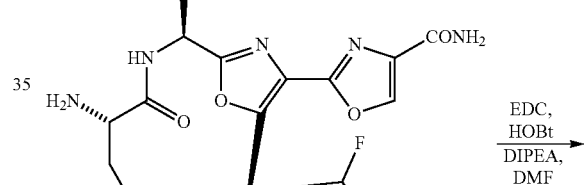

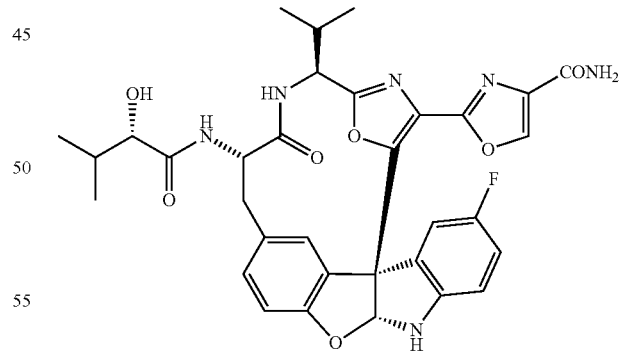

To a dry 25-ml flask containing the amine synthesized in Step 12 above (0.735 mmol) were added (S)-(+)-2-hydroxy-3-methylbutanoic acid (104 mg, 0.882 mmol, 1.2 eq.), HOBt (119 mg, 0.882 mmol, 1.2 eq.), anhydrous DMF (10 ml) and N,N-diisopropylethylamine (0.192 ml, 1.1 mmol, 1.5 eq.). The reaction mixture was cooled to 0° C. followed by addition of EDC HCl (169 mg, 0.882 mmol, 1.2 eq.). The resulting reaction mixture was stirred at room temperature for 16 h. The reaction was monitored by LCMS. The reaction mixture was

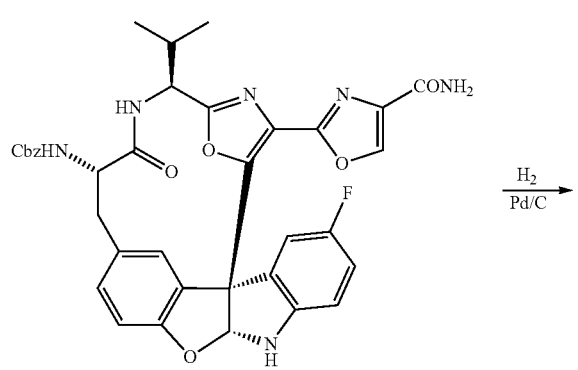

diluted with EtOAc (100 ml)/water (30 ml). The organic phase was separated and the aqueous phase was extracted by EtOAc (2×30 ml). The combined organic layers were washed by water (50 ml), 10% aqueous NaHSO₄ (50 ml), water (30 ml), saturated NaHCO₃ (50 ml), and brine (2×50 ml), and then dried over Na₂SO₄. After concentration, the crude was used directly in the next step.

Step 14

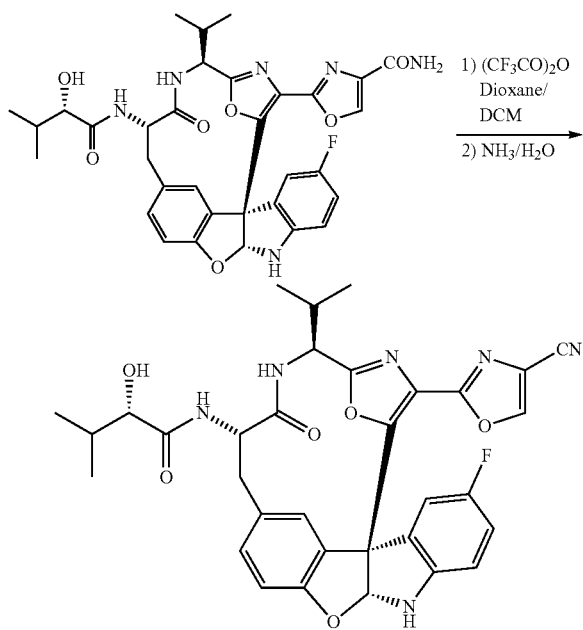

To a dry flask were added crude material synthesized in Step 13 (0.735 mmol), dioxane (10 ml) and CH₂Cl₂ (10 ml) and pyridine (1.2 ml, 14.7 mmol). This solution was cooled to −17° C. followed by addition of trifluoroacetic anhydride (1.5 ml, 11 mmol) at −10 to −17° C. After addition, the resulting mixture was stirred at −15° C. for 1 h. Then aqueous NH₃ solution (28% 10 ml) was added dropwise at −15° C. followed by warming to room temperature and stirred for 1 h. The reaction was monitored with LCMS. Most of solvent was moved under reduced pressure. The residue was extracted by ethyl acetate (3×20 ml), washed with water (2×20 ml), 5% NaHSO₄ (20 ml), water (20 ml), sat. NaHCO₃ (20 ml), water (20 ml) and brine (20 ml). The organic phase was dried over Na2SO4. After concentration the residue was purified by flash column chromatography (30% MeCN/DCM to 40% MeCN/DCM) to afford desired product as an off-white solid (115 mg, 0.184 mmol, 25% for eight steps).

Synthesis of Compound 87

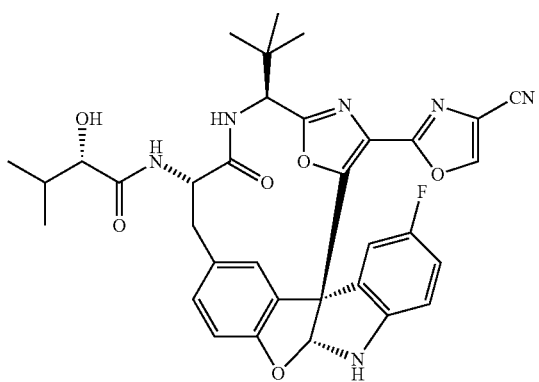

Step 1

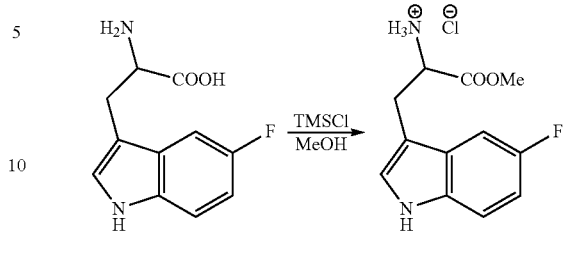

To a dry 250-ml flask were added 5-fluoro-DL-tryptophane (6.0 g, 27.0 mmol), and anhydrous methanol (120 ml). The suspension was cooled to 0° C. followed by addition of chlorotrimethyl silane (15.4 ml, 121.5 mmol, 4.5 eq.) in such a rate to keep the reaction temperature below 6° C. The resulting reaction mixture was stirred at room temperature for 20 h. The reaction was monitored by TLC. Most volatile substances were evaporated under reduced pressure. The crude was used in next step.

Step 2

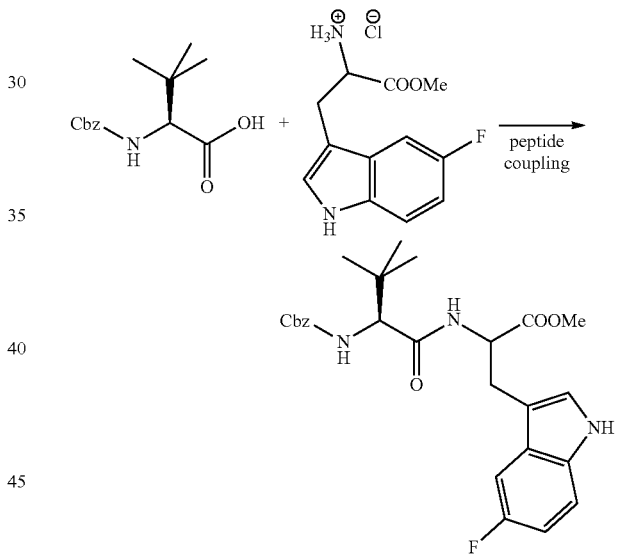

To a dry 250-ml flask with magnetic stir bar was added the amine salt synthesized in step 1 above (27 mmol.), Cbz-L-α-t-butylglycine DCHA salt (13.26 g, 29.7 mmol, 1.1 eq.), HOBt (4.01 g, 29.7 mmol, 1.1 eq.), anhydrous DMF (100 ml) and N,N-diisopropylethylamine (14.1 ml, 81 mmol, 3.0 eq.). The reaction mixture was cooled to 0° C. followed by addition of EDC HCl (5.69 g, 29.7 mmol, 1.1 eq.). The resulting reaction mixture was stirred at RT for 16 h. The reaction was monitored by LCMS. Most of solvents were evaporated under reduced pressure. Then the residue was diluted with EtOAc (700 ml)/water (200 ml). The organic phase was separated and the aqueous phase was extracted by EtOAc (2×50 ml). The combined organic layers were washed by water (100 ml), 10% aqueous NaHSO₄ (100 ml), water (100 ml), saturated NaHCO₃ (100 ml), and brine (2×100 ml), and then dried over Na₂SO₄. After concentration, the crude was used directly in the next step.

Step 3

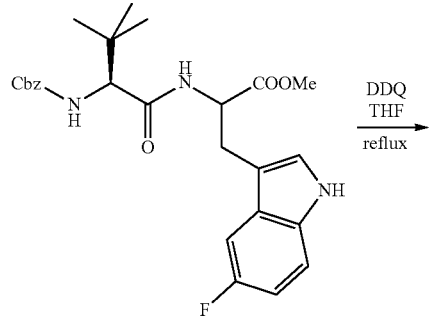

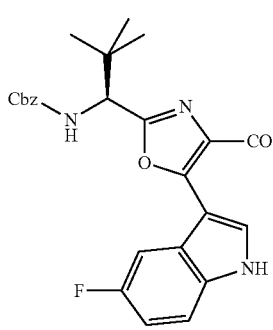

A solution of DDQ (15.32 g, 67.5 mmol, 2.5 eq.) in THF (100 ml) was added to the refluxing solution of the compound synthesized in Step 2 above (27 mmol) in THF (300 ml) and the dark solution was kept in reflux in an oil bath at 85° C. for 1 h. After cooling, the solvent was removed on a rotary evaporator. The residue was dissolved in ethyl acetate (700 ml), and NaHCO$_3$ (15 g) was added. The mixture was stirred for 1 h followed by filtration through a fritted funnel. The filtrate was washed by water (200 ml), aqueous saturated NaHCO$_3$ (2×200 ml), water (2×200 ml), brine (100 ml) and dried over Na$_2$SO$_4$. After concentration, the mixture was purified by flash column chromatography (5% EtOAc in CH$_2$Cl$_2$). This yielded 6.42 g (50% yield) of product.

Step 4

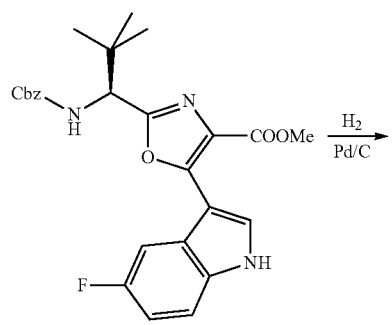

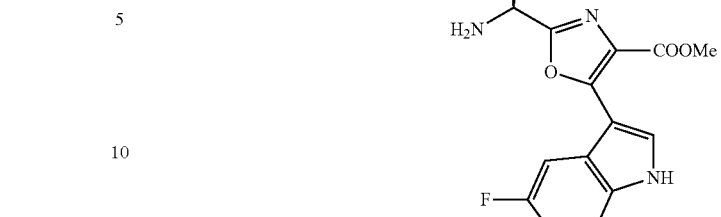

To a 250-ml flask containing material synthesized in Step 3 above (6.42 g, 13.4 mmol) was added methanol (60 ml) and Pd/C (10%) (1.43 g, 1.34 mmol, 0.1 eq.) under N$_2$. H$_2$ balloon was added and the flask was purged with H$_2$ for 4 times. Then H$_2$ balloon was opened to the reaction system. After 1 h stirring almost no starting material remained. The reaction was stopped. The reaction mixture was filtered through a pad of Celite and the black cake was washed with methanol (3×15 ml). The filtrate was concentrated and the residue was used in next step directly without further purification.

Step 5

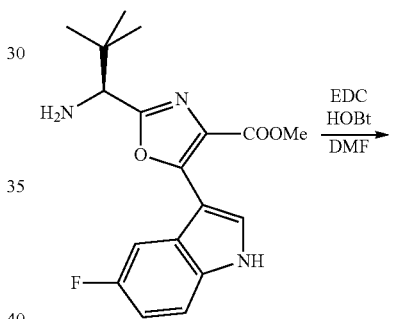

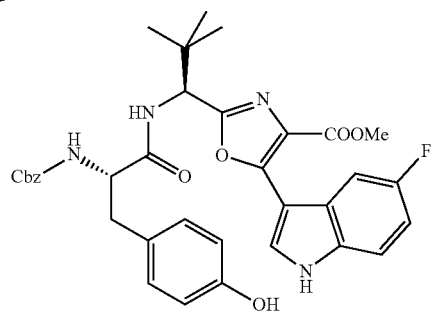

To a dry 100-ml flask with magnetic stir bar was added the amine synthesized in step 4 (13.4 mmol), Cbz-L-tyrosine (4.65 g, 14.74 mmol, 1.1 eq.), HOBt (2.0 g, 14.74 mmol, 1.1 eq.), anhydrous DMF (40 ml). The reaction mixture was cooled to 0° C. followed by addition of EDC HCl (2.83 g, 14.74 mmol, 1.1 eq.). The resulting reaction mixture was stirred at RT for 16 h. The reaction was monitored by LCMS. The reaction mixture was diluted with EtOAc (500 ml)/water (150 ml). The organic phase was separated and the aqueous phase was extracted by EtOAc (2×100 ml). The combined organic layers were washed by water (200 ml), 10% aqueous NaHSO$_4$ (150 ml), water (150 ml), saturated NaHCO$_3$ (150 ml), and brine (2×100 ml), and then dried over Na$_2$SO$_4$. After concentration, the crude was used directly in the next step.

Step 6

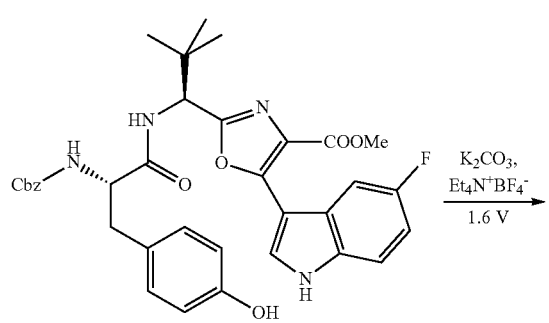

Step 7

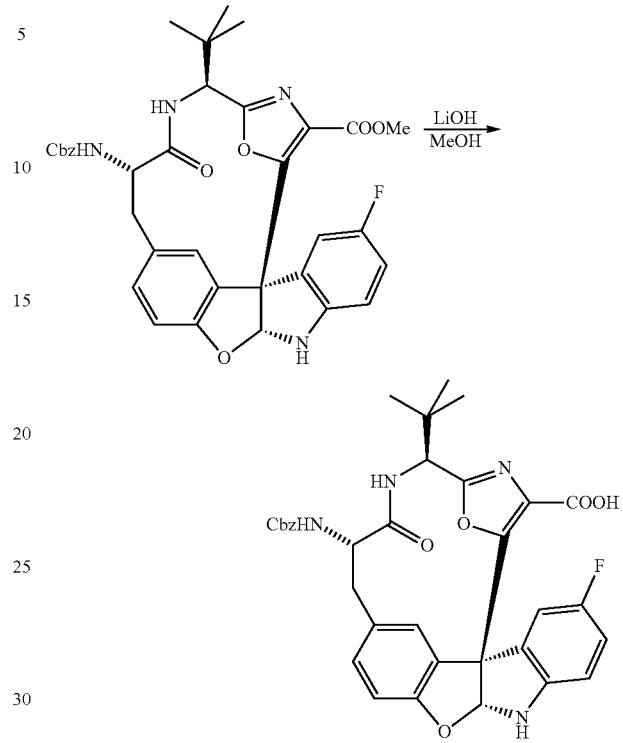

An electrochemical cell was assembled using a glass cylinder (6 cm diameter×11 cm height) and a custom rack (polypropylene and nylon) which supported 9 vertical graphite rods (6.15 mm diameter×12 cm length). The rods were arranged in a pattern of a ring with 6 anodes and 3 cathodes. Electrodes were immersed to a depth of 6.5 cm. The phenolic material synthesized in Step 5 above (2.00 g, 3.11 mmol), Et$_4$NBF$_4$ (2.00 g, 9.2 mmol, 3 eq.), K$_2$CO$_3$(0.409 g, 2.96 mmol, 0.95 eq.) and ID water (4 ml) were added in DMF (200 ml). The solution was stirred vigorously in a stir plate (approx. 600 rpm). The electrochemical reaction was carried out at a potential of 1.5-1.6 volts. After 3 days, most of the original SM was consumed as determined by HPLC integration at 220 nM. The electrochemistry reaction was repeated for 4 times to consume all phenolic material synthesized in step 5. The combined reaction mixtures were concentrated on a rotary evaporator (bath temp. ≤35° C.) and dried further on a vacuum manifold. The residue was diluted with EtOAc (500 ml) followed by filtration through a fritted funnel. The filtrate was washed by water (2×200 ml) brine (200 ml). The aqueous layers were extracted in succession with EtOAc (2×50 ml). The combined organic layers were dried (Na$_2$SO$_4$) and concentrated. This material was purified by flash column chromatography with 15% MeCN in CH$_2$Cl$_2$. This yielded 553 mg of desired product with 6.4% yield in three steps.

The compound synthesized in Step 6 (553 mg, 0.863 mmol) was dissolved in methanol (17 ml) and the solution was cooled in an ice bath. A solution of LiOH (207 mg, 8.63 mmol, 10 eq.) in water (2.7 ml) was added over 5 min. The ice bath was removed and the mixture was stirred at RT for 18 h. The mixture was cooled in an ice bath and water (20 ml) was added followed by 1 N aqueous HCl (8.8 ml), keeping the reaction temperature below 10° C. The mixture was partitioned between water (15 ml) and EtOAc (100 ml), and the organic layer was washed with saturated aqueous NaCl. The aqueous layers were extracted in succession with EtOAc (30 ml). The combined organic layers were dried (Na$_2$SO$_4$), decanted, and evaporated to give the acid product as fine white crystals.

Step 8

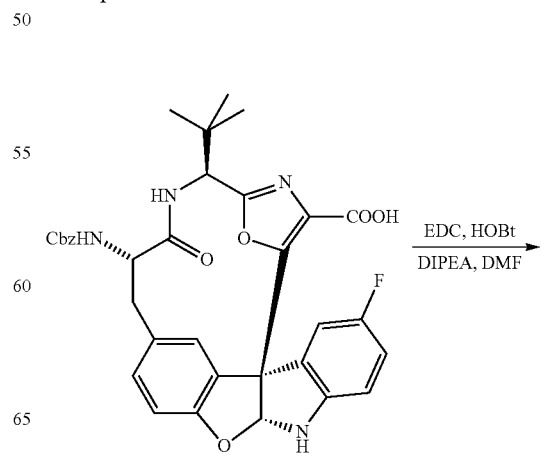

-continued

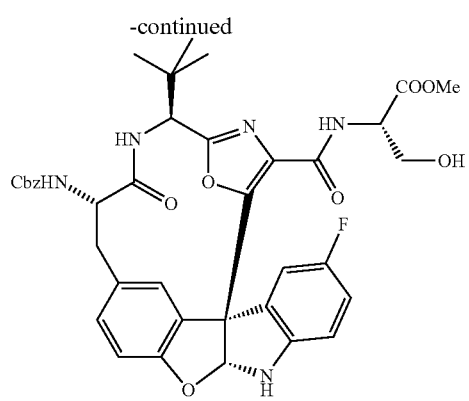

To a dry 50-ml flask with magnetic stir bar was added the carboxylic acid synthesized in step 7 above (0.863 mmol), L-serine methyl ester hydrochloride (161 mg, 1.036 mmol, 1.2 eq.), HOBt (140 mg, 1.036 mmol, 1.2 eq.), anhydrous DMF (15 ml) and N,N-diisopropylethylamine (0.346 ml, 1.99 mmol, 2.3 eq.). The reaction mixture was cooled to 0° C. followed by addition of EDC HCl (199 mg, 1.036 mmol, 1.3 eq.). The resulting reaction mixture was stirred at RT for 16 h. The reaction was monitored by LCMS. Most of solvents were evaporated under reduced pressure. The residue was diluted with EtOAc (100 ml)/water (30 ml). The organic phase was separated and the aqueous phase was extracted by EtOAc (2×20 ml). The combined organic layers were washed by water (40 ml), 10% aqueous $NaHSO_4$ (40 ml), water (40 ml), saturated $NaHCO_3$ (40 ml), and brine (2×40 ml), and then dried over $Na_2SO_4$. After concentration, the crude was used directly in the next step.

Step 9

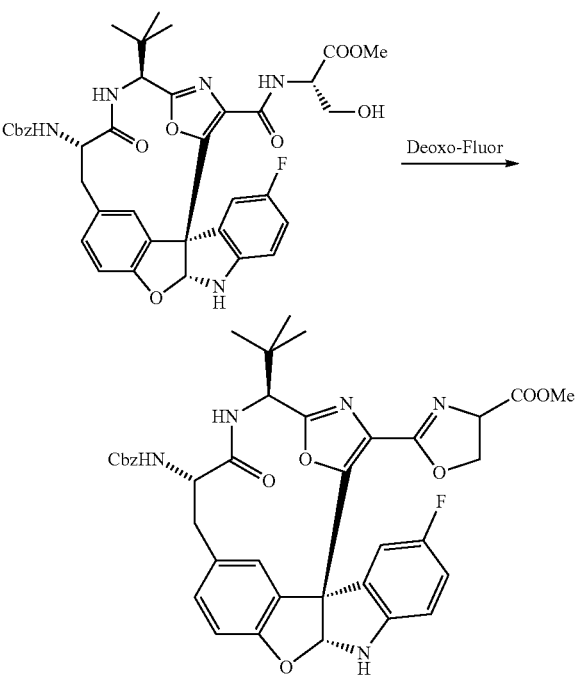

To a dry flask were added the crude product from Step 8 above (0.863 mmol) and anhydrous $CH_2Cl_2$ (15 ml). The reaction solution became cloudy as it was cooled to –20° C. in a dry ice/acetone/water bath. A freshly made stock solution of Bis(2-methoxyethyl)aminosulfur trifluoride (0.239 ml, 1.29 mmol, 1.5 eq.) in $CH_2Cl_2$ (2 ml) was added dropwise. The resulting reaction mixture was stirred at –20° C. for 1 h, and warmed to room temperature. The reaction mixture was quenched by addition of saturated aqueous $NaHCO_3$ (10 ml), diluted with EtOAc (50 ml), washed with water (2×15 ml) as well as brine (20 ml), and dried over $Na_2SO_4$. After concentration the residue was used in next step.

Step 10

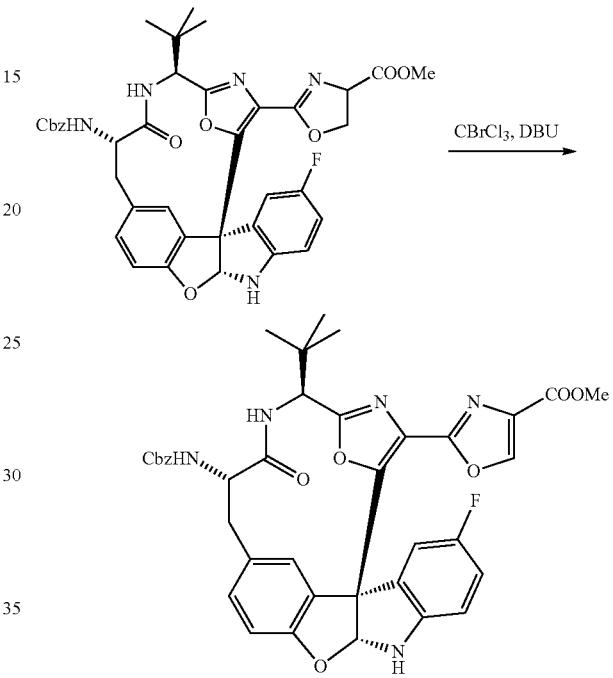

To a dry flask containing the crude product from step 9 above (0.866 mmol) were added anhydrous $CH_2Cl_2$ (15 ml). The mixture was cooled to 0° C. Then $CBrCl_3$ (0.128 ml, 1.29 mmol, 1.5 eq.) and DBU (0.193 ml, 1.29 mmol, 1.5 eq.) were added respectively. The resulting mixture was allowed to warm to room temperature and was stirred for 1 h. The reaction was monitored by LCMS. The reaction mixture was diluted with EtOAc (50 ml), washed by 10% $NaHSO_4$ (15 ml), water (2×15 ml), saturated aqueous $NaHCO_3$ (15 ml), water (15 ml) and brine (15 ml), dried over $Na_2SO_4$. After concentration the residue was used in next step.

Step 11

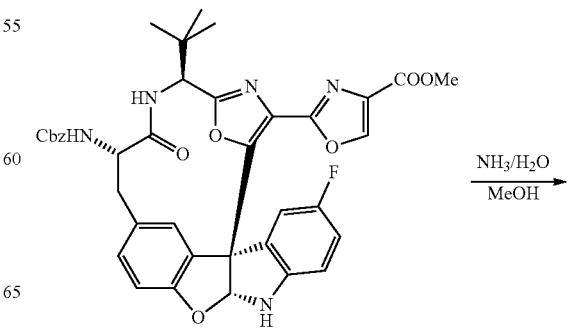

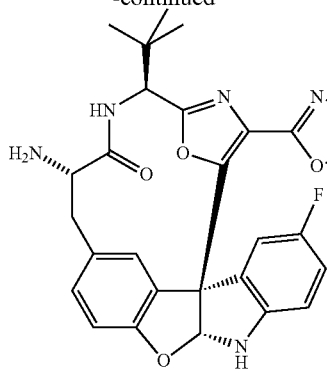

To a flask were added the product from step 10 (0.52 mmol), methanol (25 ml), aqueous ammonia solution (28%, 10 ml). The resulting reaction mixture was stirred at room temperature for 24 hrs. The reaction was monitored by TLC. Most of methanol was evaporated under reduced pressure. The residue was extracted by ethyl acetate (3×30 ml), washed with 2% NaHSO$_4$ (30 ml), water (30 ml), 5% NaHCO$_3$ (30 ml), brine (30 ml). The organic phase was dried over Na$_2$SO$_4$. After concentration, the crude was used in next step.

Step 12

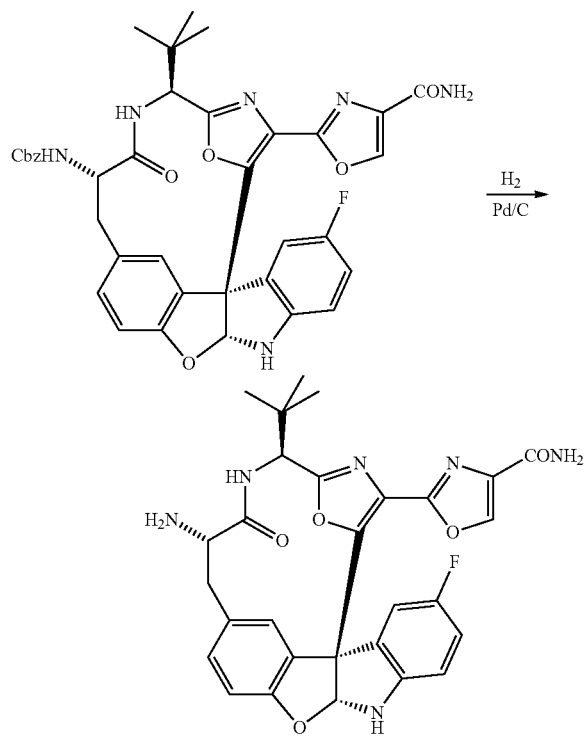

To a 100-ml flask containing material synthesized in Step 11 above (0.52 mmol) were added methanol (10 ml), t-butylamine (0.082 ml, 0.78 mmol, 1.5 eq.) and Pd/C (10%) (55 mg, 0.052 mmol, 0.1 eq.) under N$_2$. H$_2$ balloon was added and the flask was purged with H$_2$ for 4 times. Then H$_2$ balloon was opened to the reaction system. After 4 h stirring almost no starting material remained. The reaction was stopped. The reaction mixture was filtered through a pad of Celite and the black cake was washed with methanol (3×15 ml). The filtrate was concentrated and the residue was used in next step directly without further purification.

Step 13

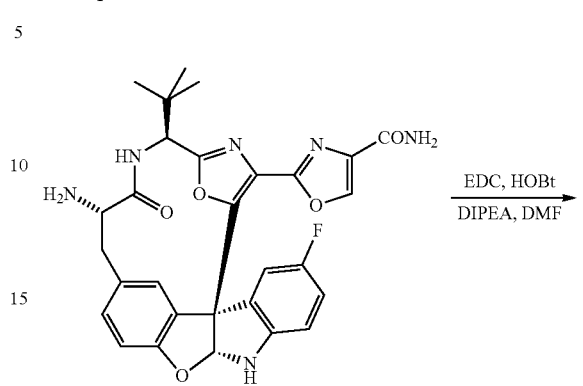

To a dry 25-ml flask containing the amine synthesized in Step 12 above (0.52 mmol) were added (S)-(+)-2-hydroxy-3-methylbutanoic acid (74 mg, 0.624 mmol, 1.2 eq.), HOBt (85 mg, 0.624 mmol, 1.2 eq.), anhydrous DMF (10 ml) and N,N-diisopropylethylamine (0.136 ml, 0.78 mmol, 1.5 eq.). The reaction mixture was cooled to 0° C. followed by addition of EDC HCl (120 mg, 0.624 mmol, 1.2 eq.). The resulting reaction mixture was stirred at room temperature for 16 h. The reaction was monitored by LCMS. The reaction mixture was diluted with EtOAc (100 ml)/water (30 ml). The organic phase was separated and the aqueous phase was extracted by EtOAc (2×30 ml). The combined organic layers were washed by water (50 ml), 10% aqueous NaHSO$_4$ (50 ml), water (30 ml), saturated NaHCO$_3$ (50 ml), and brine (2×50 ml), and then dried over Na$_2$SO$_4$. After concentration, the crude was used directly in the next step.

Step 14

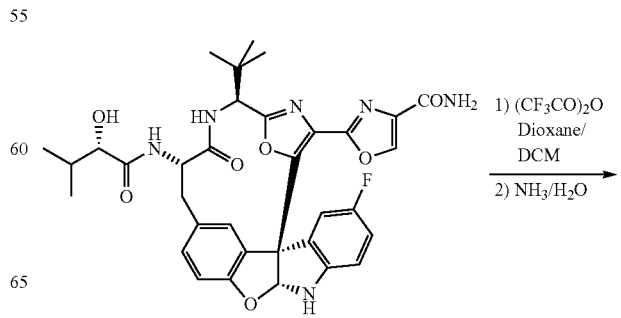

-continued

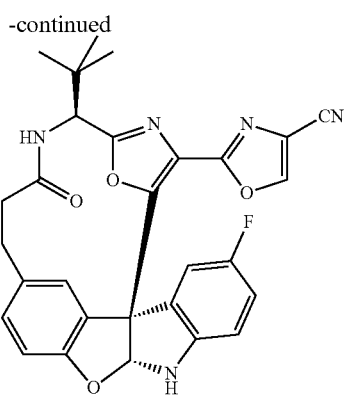

To a dry flask were added crude material synthesized in Step 13 (0.52 mmol), dioxane (7 ml) and $CH_2Cl_2$ (7 ml) and pyridine (0.841 ml, 14.7 mmol). This solution was cooled to −17° C. followed by addition of trifluoroacetic anhydride (1.1 ml, 7.8 mmol) at −10 to −17° C. After addition, the resulting mixture was stirred at −15° C. for 1 h. Then aqueous $NH_3$ solution (28% 7 ml) was added dropwise at −15° C. followed by warming to room temperature and stirred for 1 h. The reaction was monitored with LCMS. Most of solvent was moved under reduced pressure. The residue was extracted by ethyl acetate (3×20 ml), washed with water (2×20 ml), 5% $NaHSO_4$ (20 ml), water (20 ml), sat. $NaHCO_3$ (20 ml), water (20 ml) and brine (20 ml). The organic phase was dried over $Na_2SO_4$. After concentration the residue was purified by flash column chromatography (20% MeCN/DCM to 30% MeCN/DCM) to afford desired product as an off-white solid (51 mg, 0.080 mmol, 16% for eight steps).

Cell Viability Assay Protocol

Cell viability assays were run using standard protocols known to those of skill in art. Cells were plated in 96 well plates at the density of 3,000-10,000 cells per well. Twenty four hours later, cells were treated with increasing concentration of test compounds (1 nM to 1 µM). After another 48 hour, cell survival was measured using Cell-Titer-Glo® reagent (Promega) following the protocol provided by the manufacture. The $IC_{50}$ value was determined as the concentration of test compound that kills 50% of the cell population.

Representative Biological Data

Cell viability data generated according to the protocol described above was generated for representative compounds in A2058 and U937 cells. The compounds shown in Table 1 were prepared by the methods described herein for structurally similar compounds. The reference compound was a synthetic diazonamide analog having the structure:

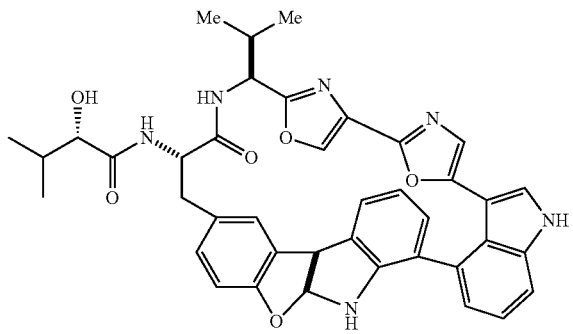

TABLE 1

| | Cell viability data in A2058 and U937 cells | | |
|---|---|---|---|
| Compound # | Structure | IC50 (nM) in cell viability assay in A2058 | IC50 (nM) in cell viability assay in U937 |
| I. Oxazole, 4 oxazoyl analogs with esters other than methyl ester in position 4. | | | |
| 21 | 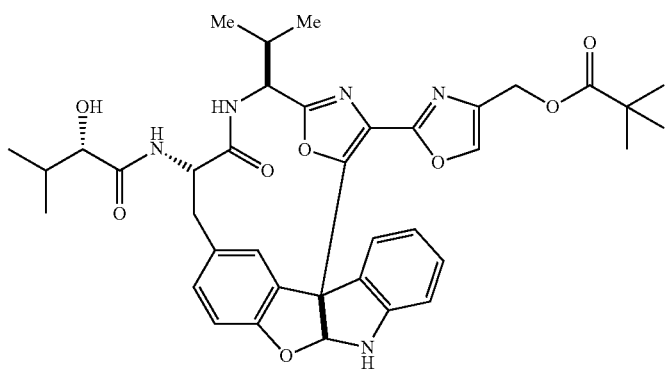 | 40 | 20 |

TABLE 1-continued

Cell viability data in A2058 and U937 cells

| Compound # | Structure | IC50 (nM) in cell viability assay in A2058 | IC50 (nM) in cell viability assay in U937 |
|---|---|---|---|
| 22 | 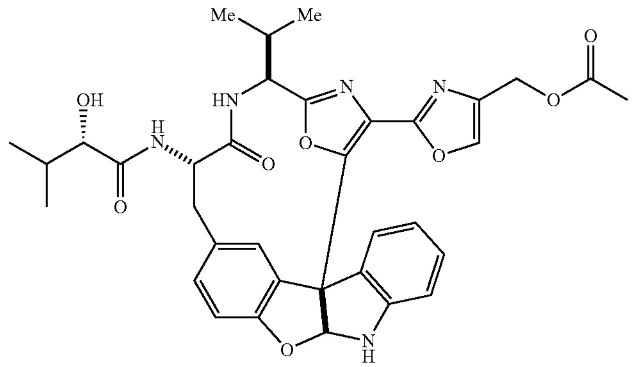 | 52 | 19 |
| 23 | 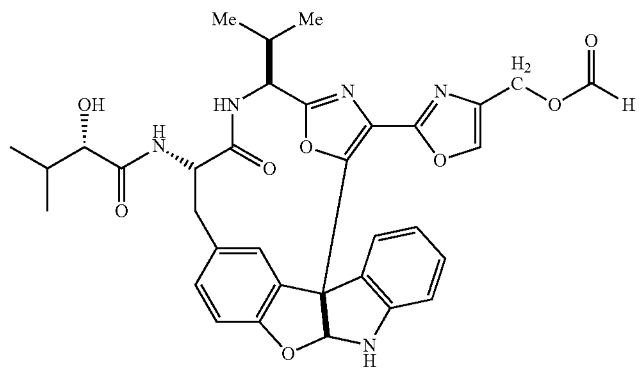 | 57 | 21 |
| 24 | 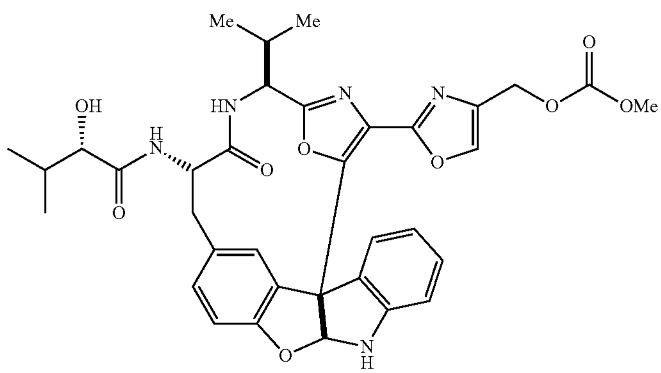 | 25.99 | 19.68 |
| 25 | 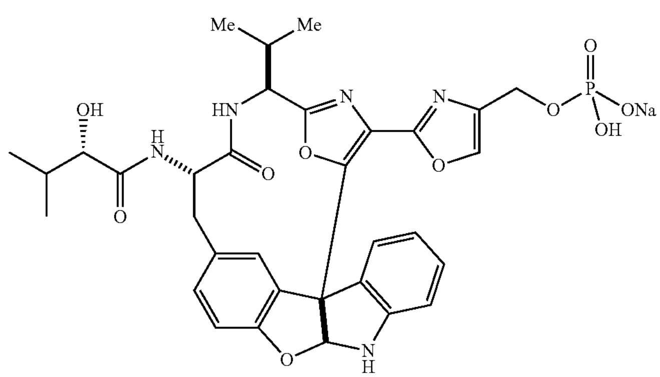 | 70.81 | 36.91 |

TABLE 1-continued

Cell viability data in A2058 and U937 cells

| Compound # | Structure | IC50 (nM) in cell viability assay in A2058 | IC50 (nM) in cell viability assay in U937 |
|---|---|---|---|
| 26 | 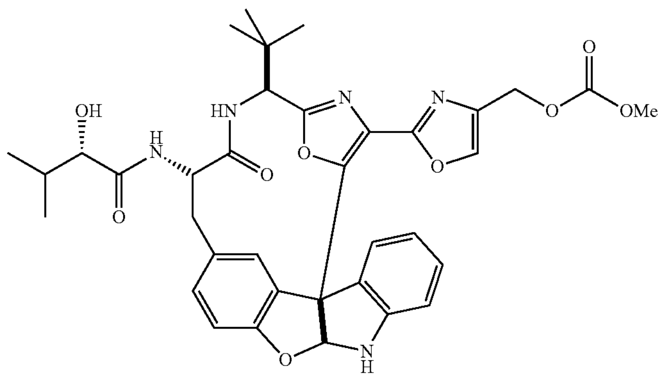 | 3.33 | 2.88 |

2. Oxazole, 4 oxazoyl analogs with alcohol or ketone in position 4

| | | | |
|---|---|---|---|
| 27 | | 112 | 98 |
| 28 | | 143 | 112 |
| 29 | | 119 | 59 |

TABLE 1-continued

Cell viability data in A2058 and U937 cells

| Compound # | Structure | IC50 (nM) in cell viability assay in A2058 | IC50 (nM) in cell viability assay in U937 |
|---|---|---|---|
| 30 | 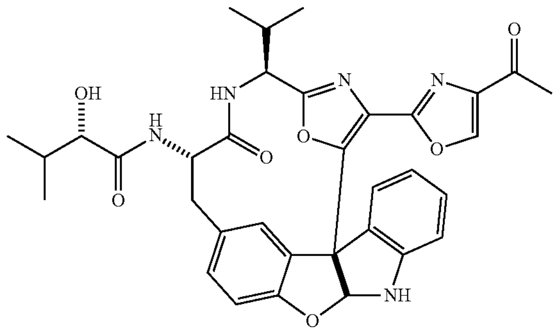 | 60 | 13 |
| 31 | 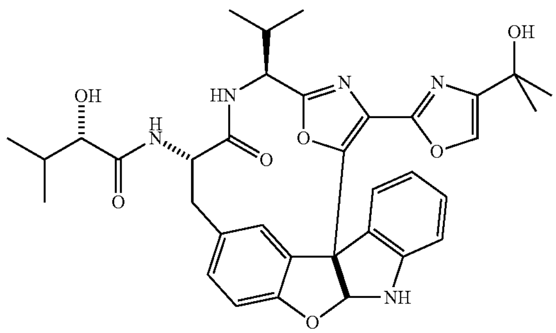 | 602 | 259 |

III. Oxazole, 4 oxazoyl analogs with amide, amine, carbamate or sulfonamide in position 4

| | | | |
|---|---|---|---|
| 32 | | >1000 | >1000 |
| 33 | | >1000 | >1000 |

TABLE 1-continued

Cell viability data in A2058 and U937 cells

| Compound # | Structure | IC50 (nM) in cell viability assay in A2058 | IC50 (nM) in cell viability assay in U937 |
|---|---|---|---|
| 34 | *(structure)* | 149.1 | 133.5 |
| 35 | *(structure)* | 150.8 | 198 |
| 36 | *(structure)* | 194 | 209.3 |
| 37 | *(structure)* | 235.21 | 177.9 |

TABLE 1-continued

Cell viability data in A2058 and U937 cells

| Compound # | Structure | IC50 (nM) in cell viability assay in A2058 | IC50 (nM) in cell viability assay in U937 |
|---|---|---|---|
| IV. Oxazole, 4 oxazoyl analogs with cyano-group in position 4 ||||
| 38 | 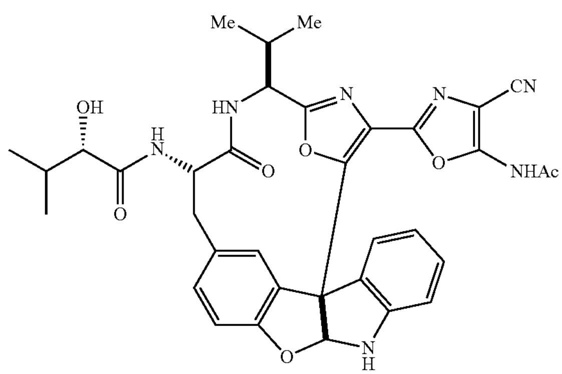 | >1000 | >1000 |
| 39 | 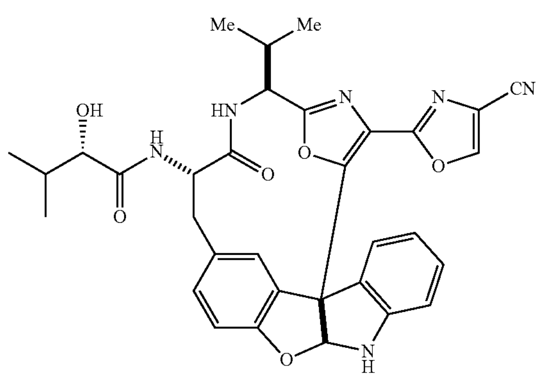 | 23 | 71 |
| 40 | 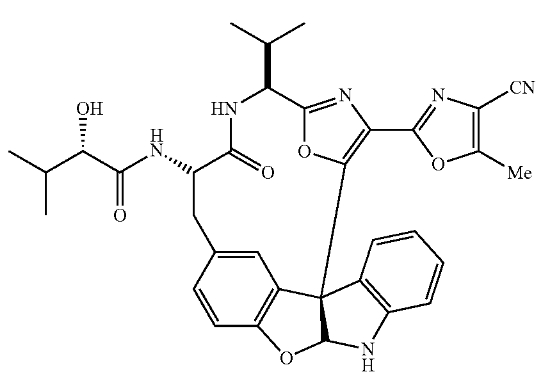 | 181.6 | 209.89 |

TABLE 1-continued

Cell viability data in A2058 and U937 cells

| Compound # | Structure | IC50 (nM) in cell viability assay in A2058 | IC50 (nM) in cell viability assay in U937 |
|---|---|---|---|
| V. Oxazole, 4 oxazoyl analogs with heterocycles in position 4 ||||
| 41 | 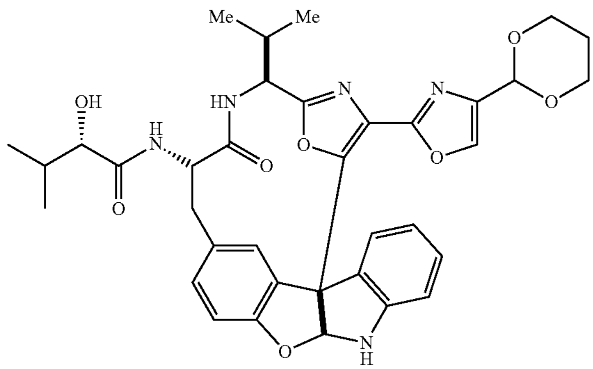 | 65 | 65 |
| 42 | 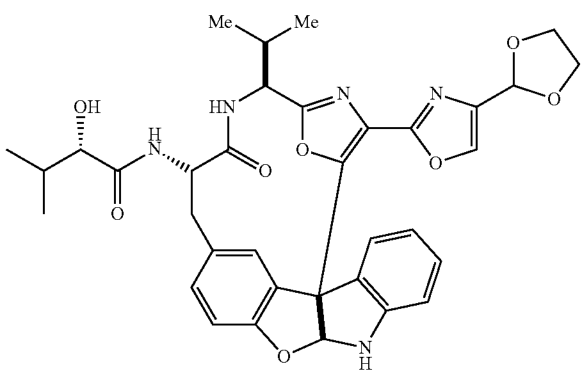 | 49 | 43 |
| 43 | 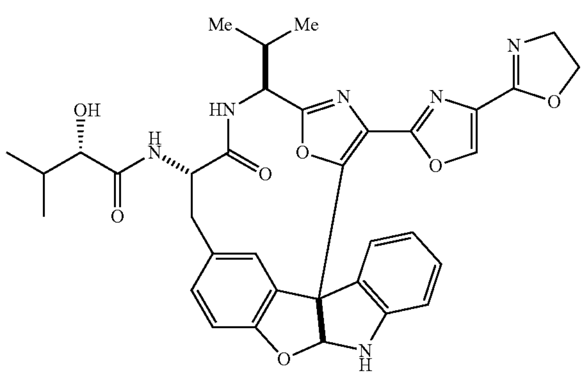 | 22 | 19 |

TABLE 1-continued

Cell viability data in A2058 and U937 cells

| Compound # | Structure | IC50 (nM) in cell viability assay in A2058 | IC50 (nM) in cell viability assay in U937 |
|---|---|---|---|
| 44 | 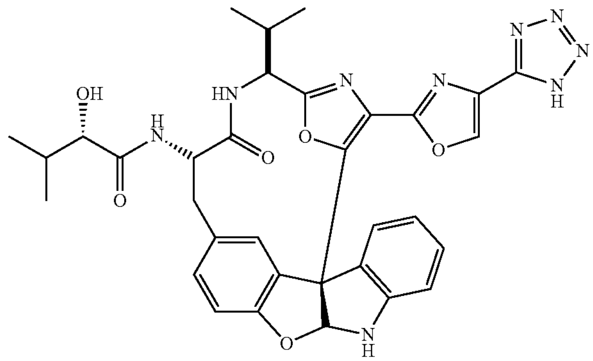 | >1000 | >1000 |
| 45 | 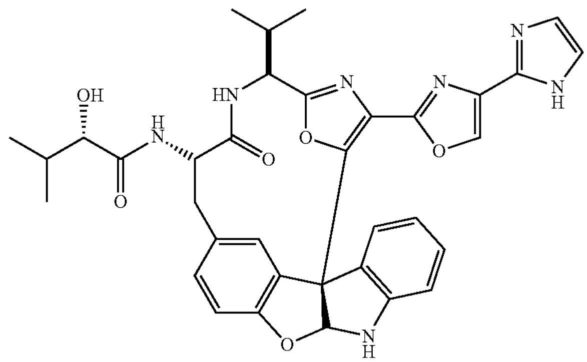 | 589 | 318 |
| 46 | 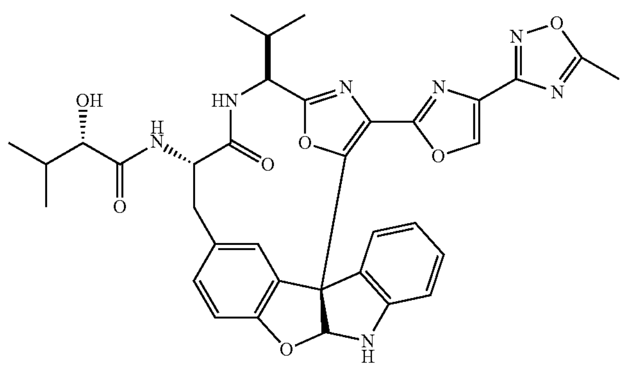 | 49.04 | 76.88 |
| 47 | 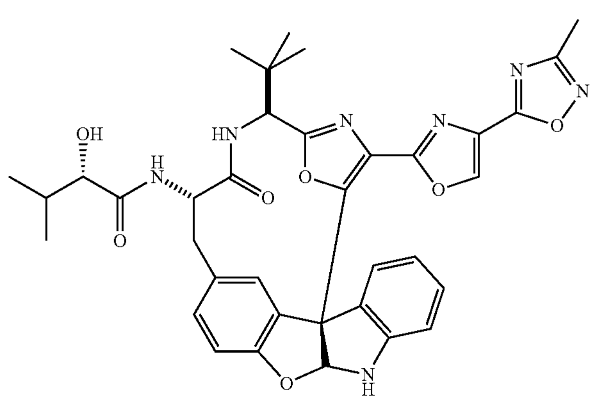 | 7.06 | 14.16 |

TABLE 1-continued

Cell viability data in A2058 and U937 cells

| Compound # | Structure | IC50 (nM) in cell viability assay in A2058 | IC50 (nM) in cell viability assay in U937 |
|---|---|---|---|
| 48 | 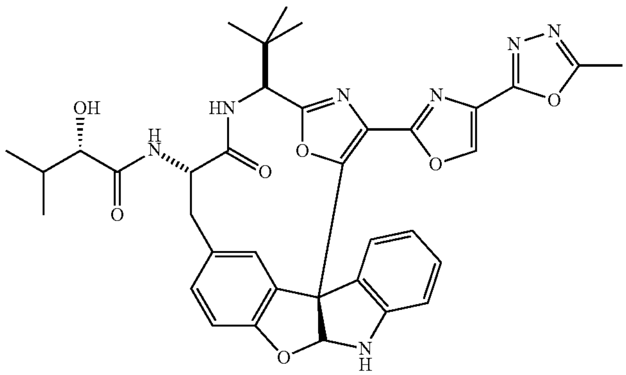 | 6.11 | 6.34 |

VI. Oxazole, 4 oxazoyl analogs with substituents replacing isopropyl group

| | | | |
|---|---|---|---|
| 49 | | >1000 | 223 |
| 50 | | 53 | 12 |

TABLE 1-continued

Cell viability data in A2058 and U937 cells

| Compound # | Structure | IC50 (nM) in cell viability assay in A2058 | IC50 (nM) in cell viability assay in U937 |
|---|---|---|---|
| 51 | 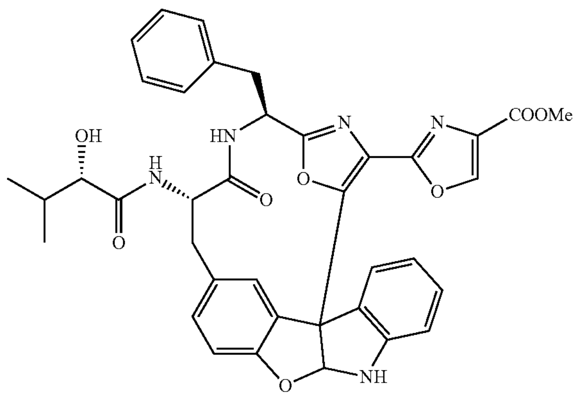 [SMILES: COC(=O)c1coc(-c2nc3oc2C24c5ccccc5NC2Oc2ccc(cc24)C[C@H](NC(=O)[C@@H](O)C(C)C)C(=O)N[C@H]3Cc2ccccc2)n1] | >1000 | >1000 |
| 52 | 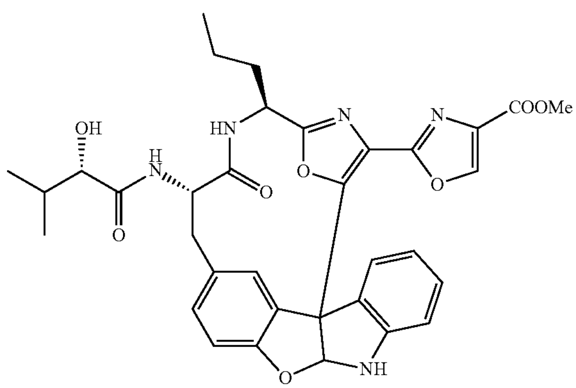 [SMILES: CCC[C@@H]1NC(=O)[C@@H](NC(=O)[C@@H](O)C(C)C)Cc2ccc3c(c2)C2(c4ccccc4NC2O3)c2oc1nc2-c1nc(C(=O)OC)co1] | 257 | 71 |
| 53 | 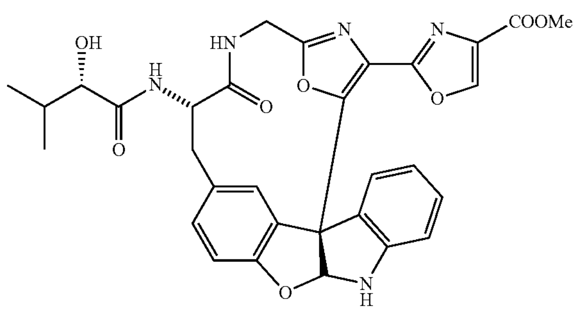 | >1000 | >1000 |
| 54 | 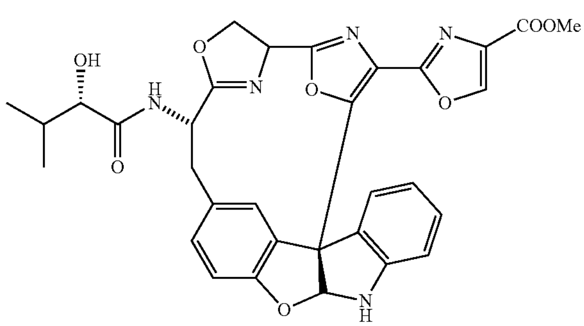 | >1000 | >1000 |

TABLE 1-continued

Cell viability data in A2058 and U937 cells

| Compound # | Structure | IC50 (nM) in cell viability assay in A2058 | IC50 (nM) in cell viability assay in U937 |
|---|---|---|---|
| 55 | 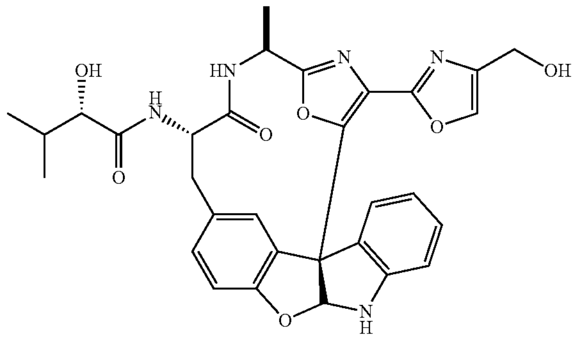 | >1000 | >1000 |
| 56 | 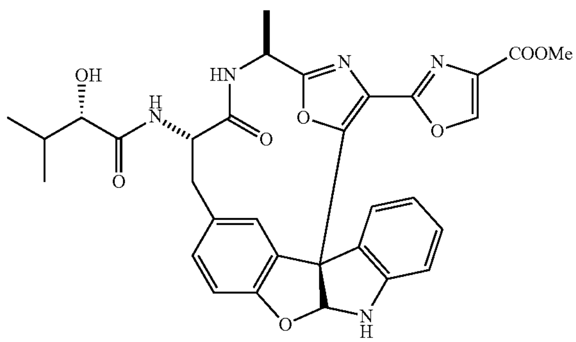 | 968 | 588 |
| 57 | 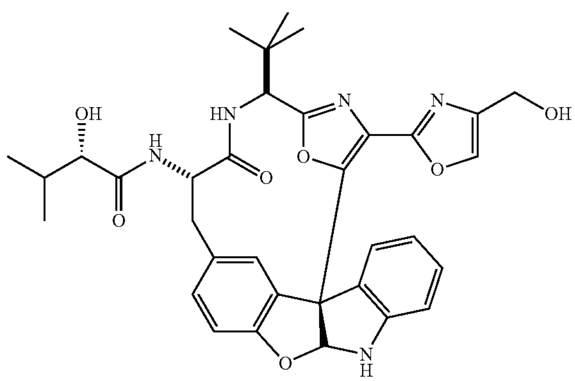 | 8.3 | 5.3 |
| 58 | 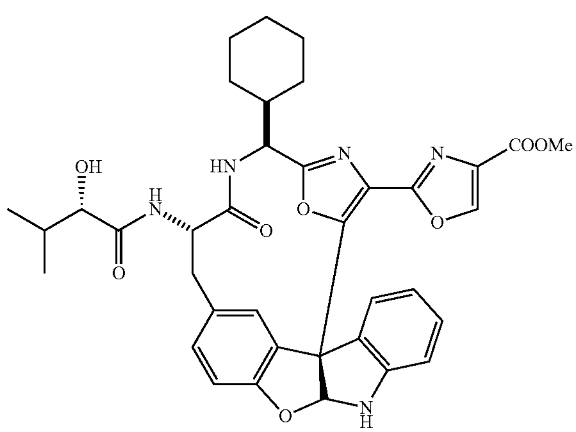 | >1000 | 445 |

TABLE 1-continued

Cell viability data in A2058 and U937 cells

| Compound # | Structure | IC50 (nM) in cell viability assay in A2058 | IC50 (nM) in cell viability assay in U937 |
|---|---|---|---|
| 59 | 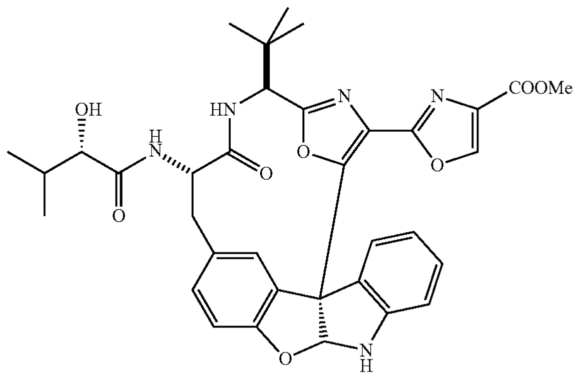 | 221 | 69 |
| 60 | 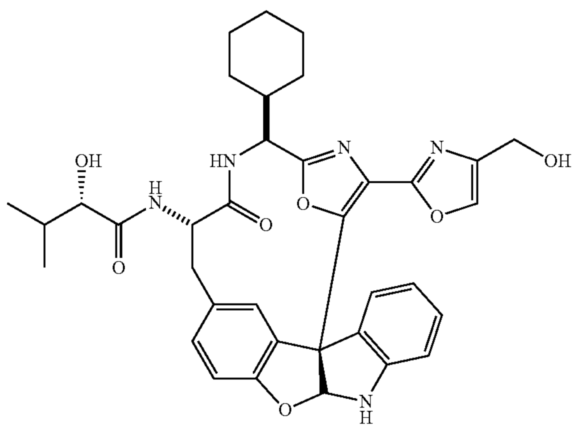 | >1000 | 795 |
| 61 | 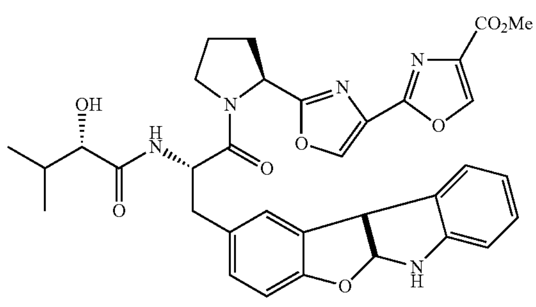 | >1000 | 761 |
| 62 | 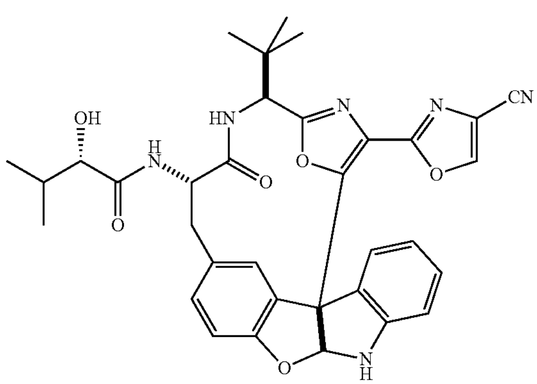 | 2.54 | 15.64 |

TABLE 1-continued

Cell viability data in A2058 and U937 cells

| Compound # | Structure | IC50 (nM) in cell viability assay in A2058 | IC50 (nM) in cell viability assay in U937 |
|---|---|---|---|
| 63 | 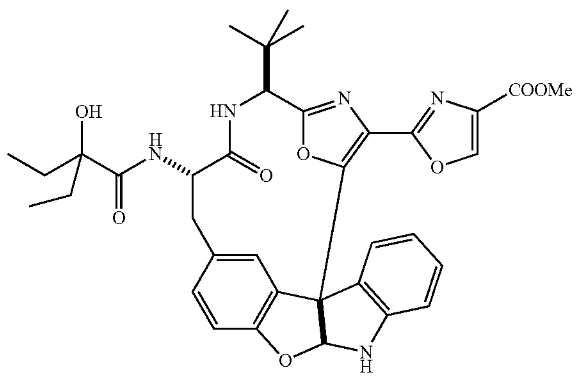 | 15.5 | 1.97 |
| 64 | 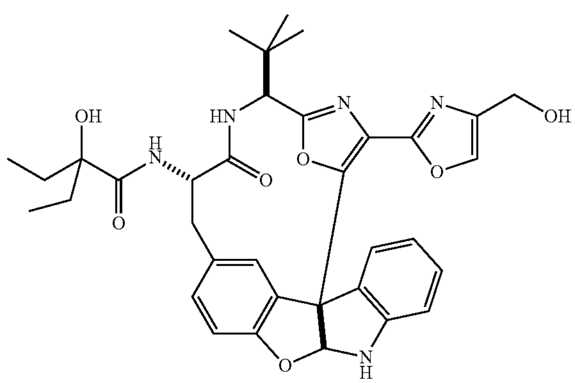 | 43.22 | 45.92 |
| 65 | 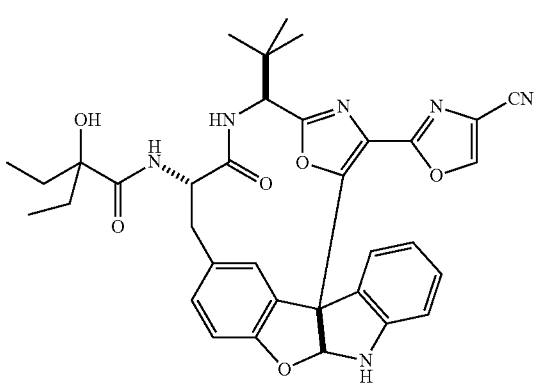 | 16.82 | 67.56 |

TABLE 1-continued
Cell viability data in A2058 and U937 cells
| Compound # | Structure | IC50 (nM) in cell viability assay in A2058 | IC50 (nM) in cell viability assay in U937 |
|---|---|---|---|
| 66 | 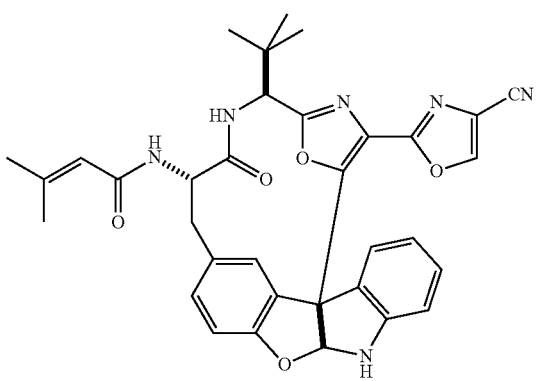 | 186.16 | 214.9 |
| 67 | 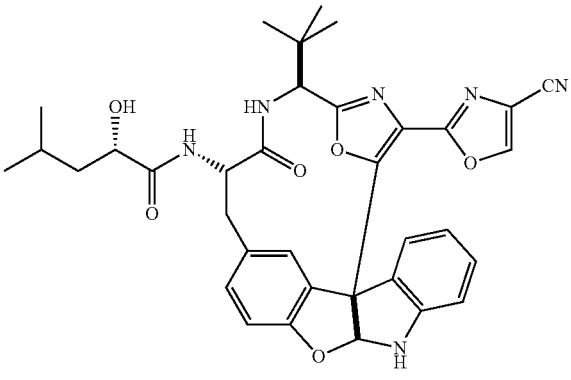 | 35.78 | 89.7 |
| 68 | 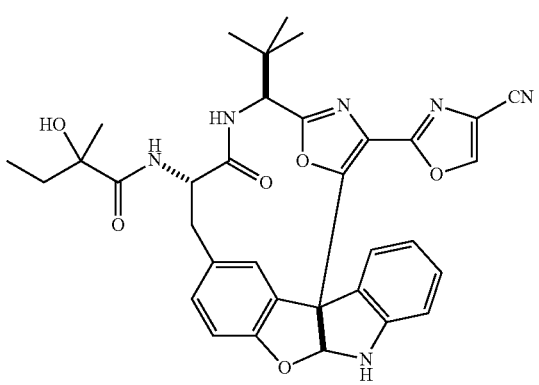 | 21.07 | 59.6 |

TABLE 1-continued

Cell viability data in A2058 and U937 cells

| Compound # | Structure | IC50 (nM) in cell viability assay in A2058 | IC50 (nM) in cell viability assay in U937 |
|---|---|---|---|
| 69 | 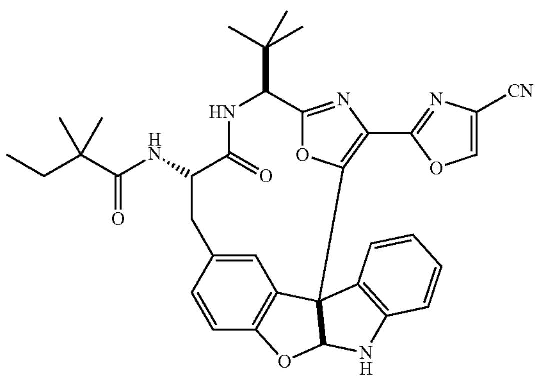 | 95.52 | 225.2 |

*7. Oxazole, 4 oxazoyl analogs with variations in tyrosine moiety*

| | | | |
|---|---|---|---|
| 70 | | 77 | 15 |
| 71 | | 67 | 9.2 |

TABLE 1-continued
Cell viability data in A2058 and U937 cells
| Compound # | Structure | IC50 (nM) in cell viability assay in A2058 | IC50 (nM) in cell viability assay in U937 |
|---|---|---|---|
| 72 | 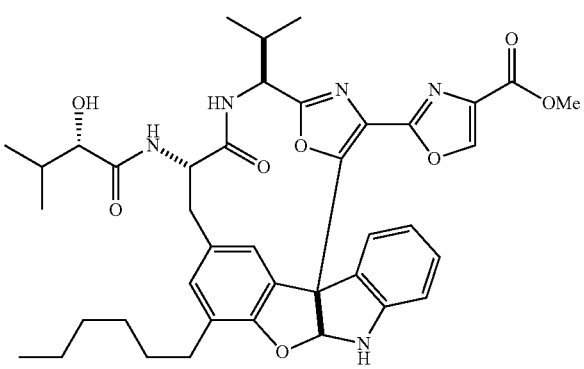 | >300 | 213.05 |
| 73 | 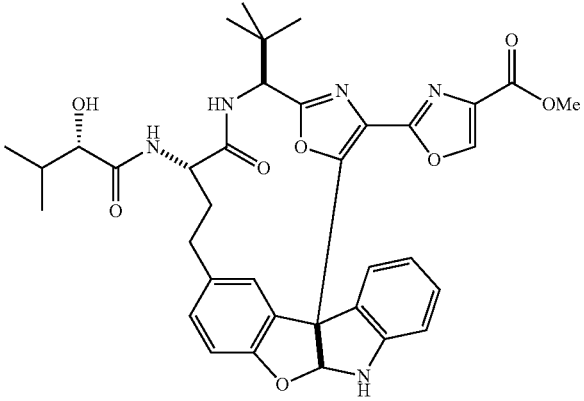 | <0.1 | <0.1 |
| 74 | 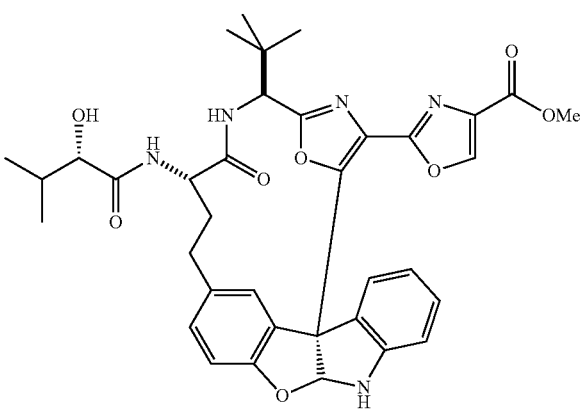 | >100 | >100 |

TABLE 1-continued

Cell viability data in A2058 and U937 cells

| Compound # | Structure | IC50 (nM) in cell viability assay in A2058 | IC50 (nM) in cell viability assay in U937 |
|---|---|---|---|
| 75 | 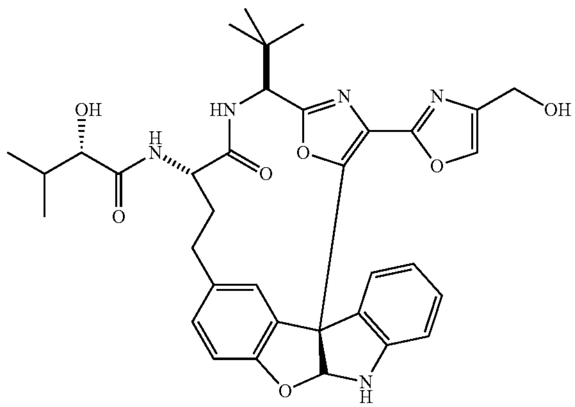 | 1.89 | 6.55 |

8. Oxazole, 4 oxazoyl analogs with variations in indoline moiety

| 76 | | >1000 | 614 |
| 77 | | >1000 | 777 |

TABLE 1-continued

Cell viability data in A2058 and U937 cells

| Compound # | Structure | IC50 (nM) in cell viability assay in A2058 | IC50 (nM) in cell viability assay in U937 |
|---|---|---|---|
| 78 | 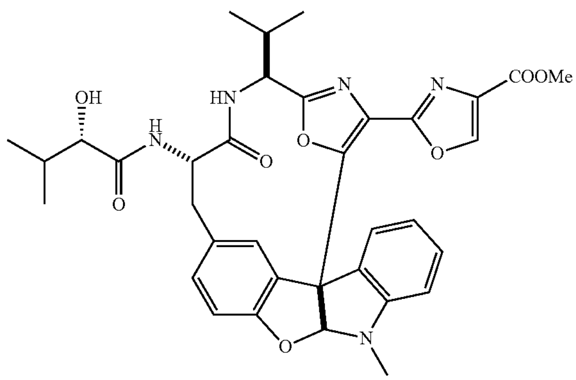 | 113.8 | 17.39 |
| 79 | 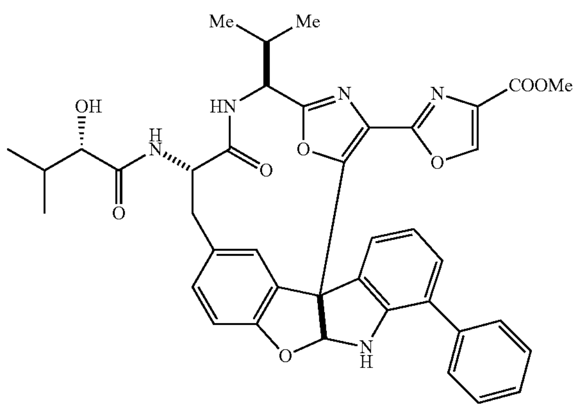 | 270 | 209.6 |
| 80 | 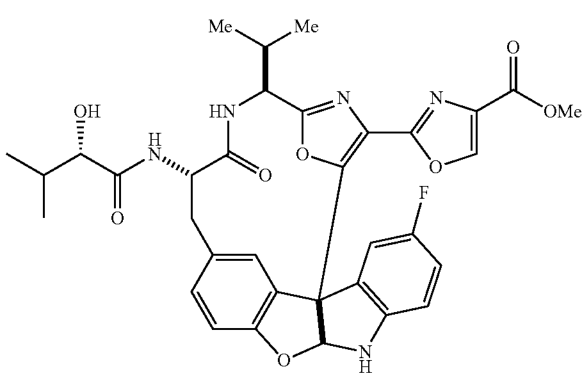 | 13.58 | 4.07 |

TABLE 1-continued
Cell viability data in A2058 and U937 cells
| Compound # | Structure | IC50 (nM) in cell viability assay in A2058 | IC50 (nM) in cell viability assay in U937 |
|---|---|---|---|
| 81 | 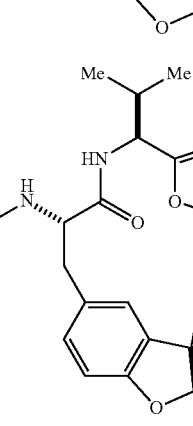 | 55.08 | 32.77 |
| 82 | 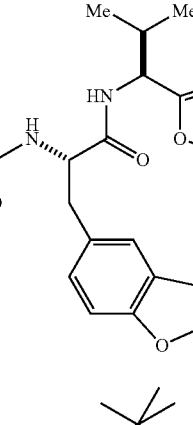 | 40.91 | 3.4 |
| 83 | 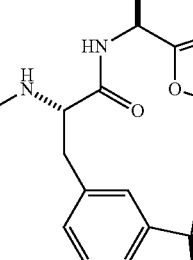 | 183.87 | 60.6 |
| 84 | 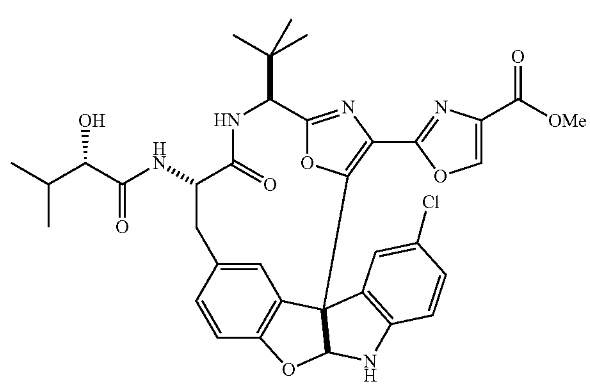 | 19.51 | 10.13 |

TABLE 1-continued

Cell viability data in A2058 and U937 cells

| Compound # | Structure | IC50 (nM) in cell viability assay in A2058 | IC50 (nM) in cell viability assay in U937 |
|---|---|---|---|
| 85 | 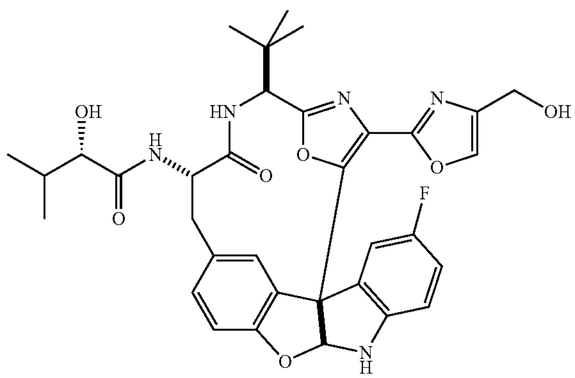 | 0.47 | 0.74 |
| 86 | 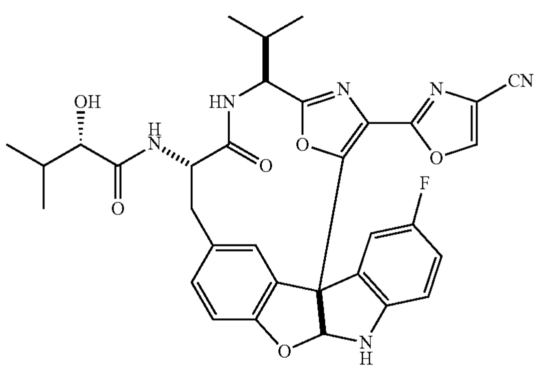 | 0.56 | 21.78 |
| 87 | 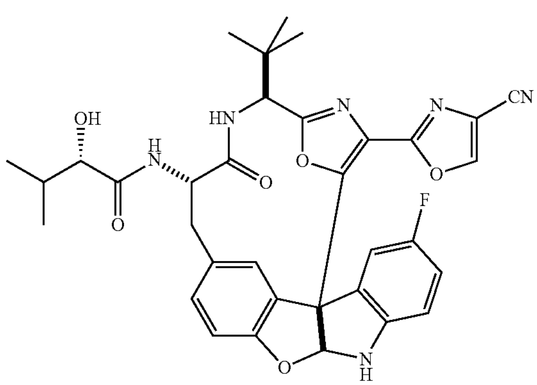 | <0.3 | 1.9 |

TABLE 1-continued

Cell viability data in A2058 and U937 cells

| Compound # | Structure | IC50 (nM) in cell viability assay in A2058 | IC50 (nM) in cell viability assay in U937 |
|---|---|---|---|
| IX. Oxazole, 4 oxazoyl analogs with N-Methyl group in side chain and/or macrocyclic moiety | | | |
| 88 | 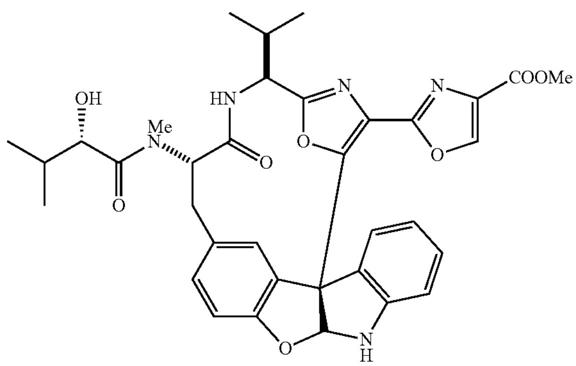 | 0.8 | 0.6 |
| 89 | 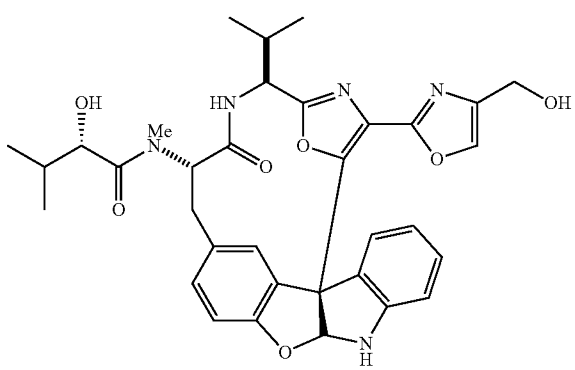 | 3 | 1 |
| 90 | 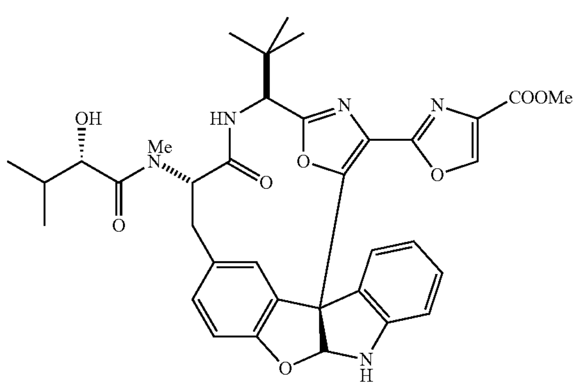 | 10.4 | 17.12 |

TABLE 1-continued

Cell viability data in A2058 and U937 cells

| Compound # | Structure | IC50 (nM) in cell viability assay in A2058 | IC50 (nM) in cell viability assay in U937 |
|---|---|---|---|
| 91 | 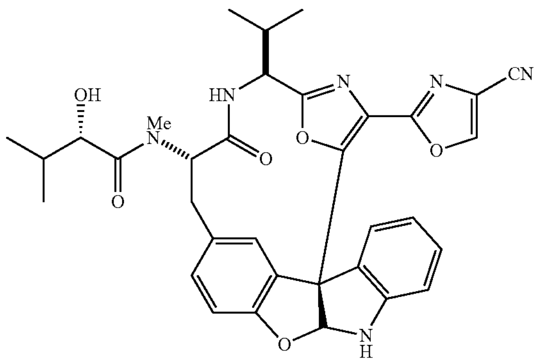 | 0.59 | 1.97 |
| 92 | 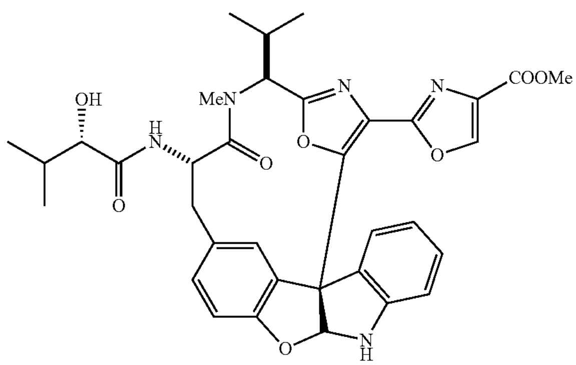 | 113.35 | 69.88 |
| 93 | 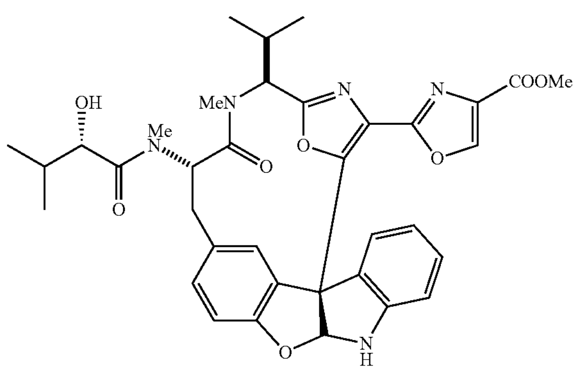 | 35.75 | 18.57 |
| 94 | 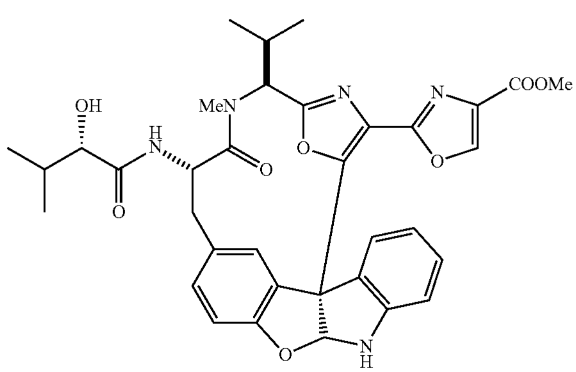 | >300 | >300 |

TABLE 1-continued

Cell viability data in A2058 and U937 cells

| Compound # | Structure | IC50 (nM) in cell viability assay in A2058 | IC50 (nM) in cell viability assay in U937 |
|---|---|---|---|
| X. Oxazole, 4-aryl (non-oxazole) analogs ||||
| 95 | 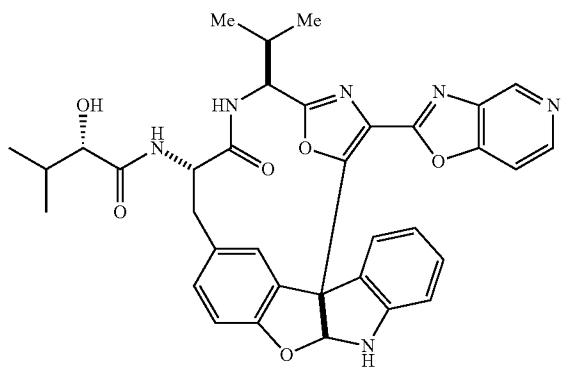 | 142 | 65 |
| 96 | 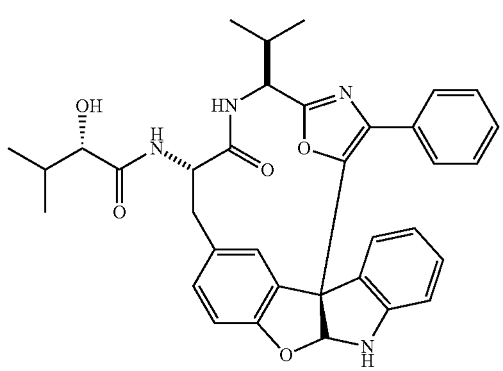 | >1000 | >1000 |
| 97 | 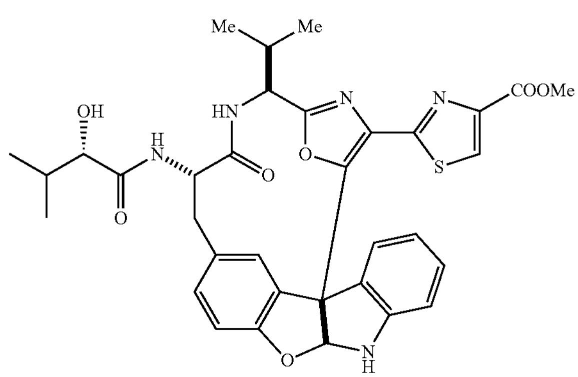 | 224.96 | 59.51 |

TABLE 1-continued
Cell viability data in A2058 and U937 cells
| Compound # | Structure | IC50 (nM) in cell viability assay in A2058 | IC50 (nM) in cell viability assay in U937 |
|---|---|---|---|
| 98 | 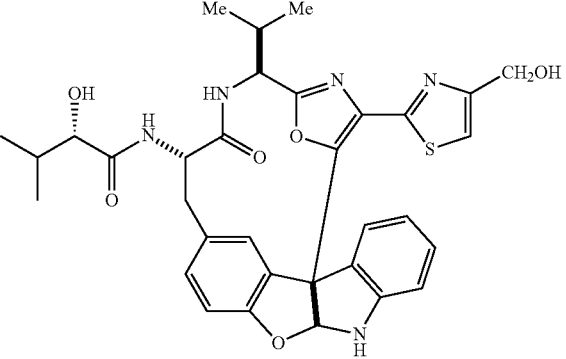 | 284.3 | 231.3 |
11. Oxazole, 4 oxazoyl analogs
| | | | |
|---|---|---|---|
| 99 | 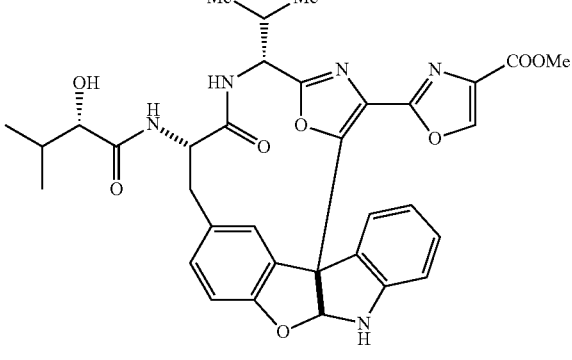 | >1000 | >1000 |
| 100 | 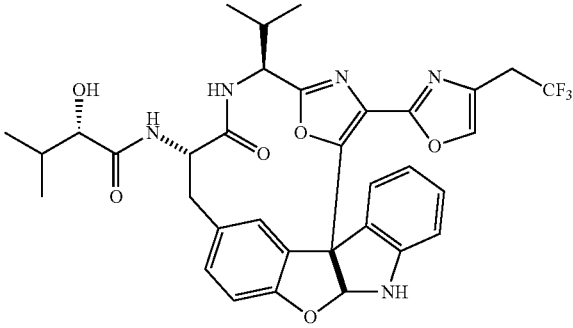 | 465 | 220 |
| 101 | 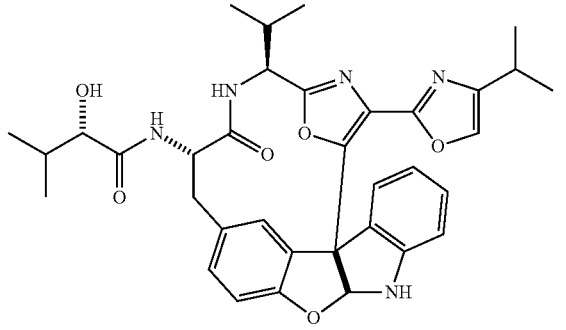 | 684 | 500 |

TABLE 1-continued

Cell viability data in A2058 and U937 cells

| Compound # | Structure | IC50 (nM) in cell viability assay in A2058 | IC50 (nM) in cell viability assay in U937 |
|---|---|---|---|
| 102 | [structure with Me, Me, OH, HN, N, O, OH, indoline, Tentative] | 492 | 225 |
| 103 | [structure with OH, HN, N, COOMe, O, NH] | 221 | 69 |
| 104 | [structure with OH, HN, N, OMe, O] | >300 | >300 |
| 105 | [structure with OH, HN, N, OMe, O] | >300 | >300 |

Xenograft Tumor Models

The compounds were tested in HCC461 human lung carcinoma xenograft and Miapaca pancreatic cancer xenograft tumor models in 5- to 6-week-old Harlan Athymic Nude-Foxnlnu mice.

Protocol:

Preparation of Tumor Cells

Tumor cells were cultured in complete RPMI medium and excluded any contamination. When cells are 70-80% confluent, medium was removed and cells were washed with serum free media, trypsinized, harvested and washed with serum free media for three times by centrifuge. After final washing, cells were counted and mixed with matrigel at 1:1 ration in volume. Cells were suspended in a volume that 200 µl contains required number of cells per injection.

Preparation of the Injection

Clean and sterilize the inoculation area of the mice with iodine solutions and ethanol. Take cells with 1-cc syringe. Inject tumor cells ($1 \times 10^7$) subcutaneously (s.c.) into the lower flank of the mice. When tumors reached 200-300 mm$^3$ in size, mice were randomized into treatment groups of five mice per group. Mice were weighed and tumors measured using vernier calipers two times per week. Tumor volume in mm$^3$ is calculated by the formula: Volume (mm$^3$)=(length×width$^2$)/2.

Treatment

The compounds were dissolved in cremophor/ethanol (1:1) at 20 mg/mL as the stock solution and then diluted in saline to 2.5 mg/mL. The compounds and the vehicle (6.25% cremophor/6.25% ethanol in saline) were administered intravenously in a total volume of 0.2 mL three times a week for total six treatments.

In the HCC461 lung cancer xenograft model, animals were injected on days 7, 11, 14 and 18 post tumor-cell injection.

In the Miapaca pancreatic cancer xenograft model, animals were injected on days 6, 13, and 20 post tumor-cell injection.

Results

Figure 2:
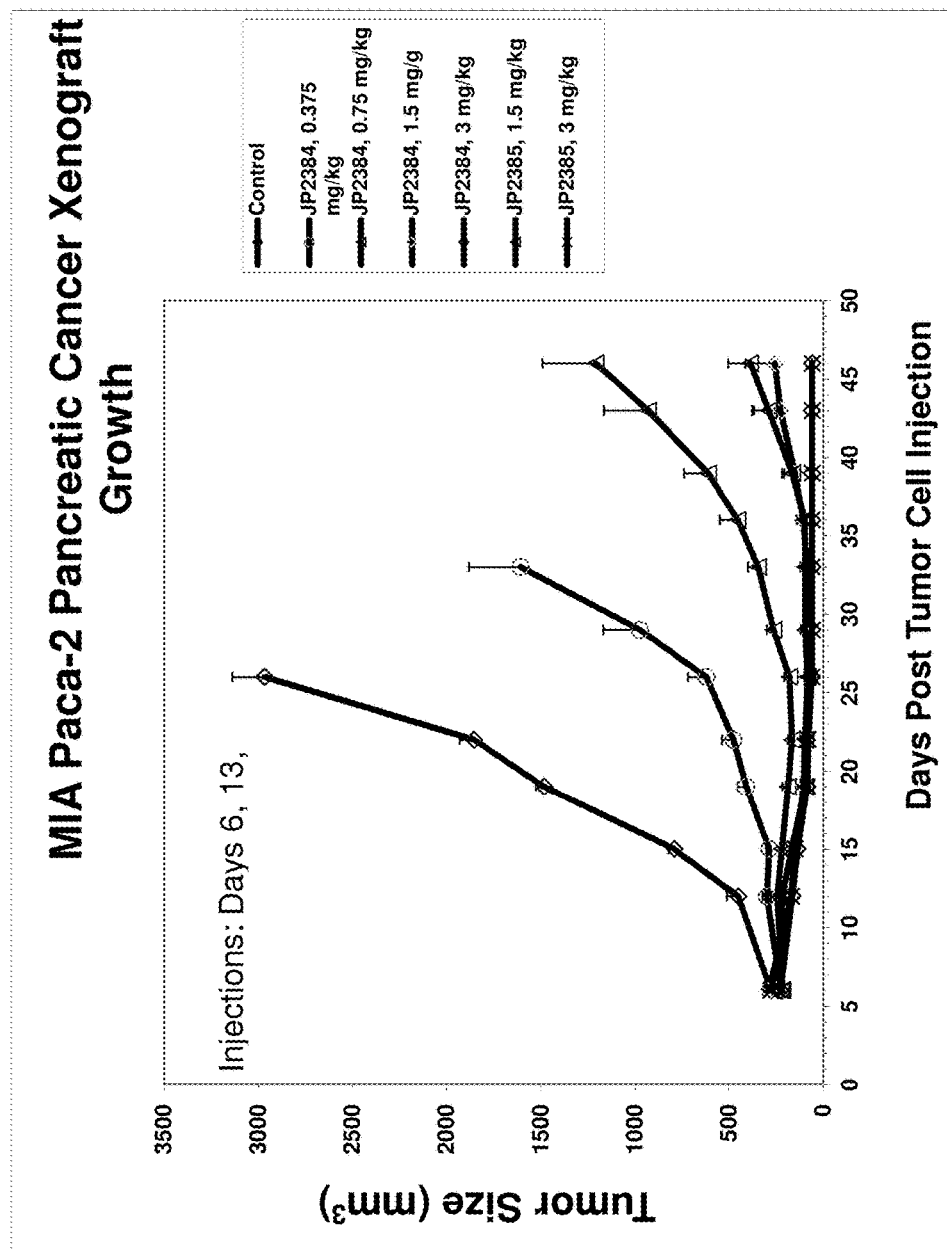
FIG. 2 shows data for subject compounds in a Miapaca pancreatic cancer xenograft model in mice.

The activities of exemplary compounds and dosages are shown in FIGS. 1 and 2.

The entirety of each patent, patent application, publication and document referenced herein hereby is incorporated by reference. Citation of the above patents, patent applications, publications and documents is not an admission that any of the foregoing is pertinent prior art, nor does it constitute any admission as to the contents or date of these publications or documents.

Modifications may be made to the foregoing without departing from the basic aspects of the invention. Although the invention has been described in substantial detail with reference to one or more specific embodiments, those of ordinary skill in the art will recognize that changes may be made to the embodiments specifically disclosed in this application, and yet these modifications and improvements are within the scope and spirit of the invention.

The invention claimed is:

1. A compound of the following table, or a pharmaceutically acceptable salt thereof:

I. Oxazole, 4 oxazoyl analogs with esters other than methyl ester in position 4

21
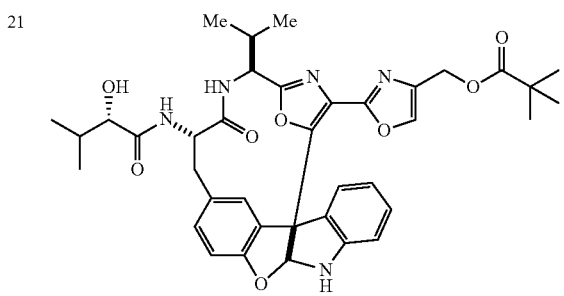

22
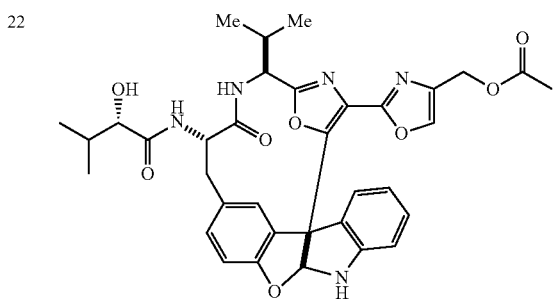

23
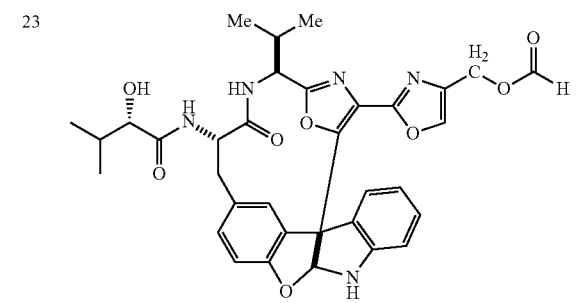

24
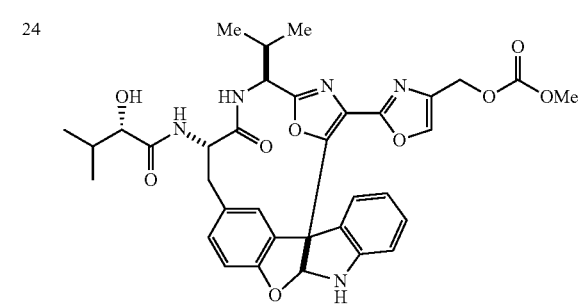

25
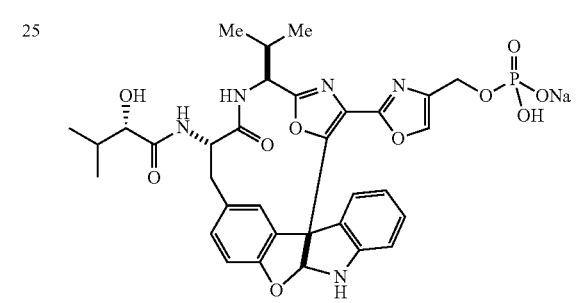

26
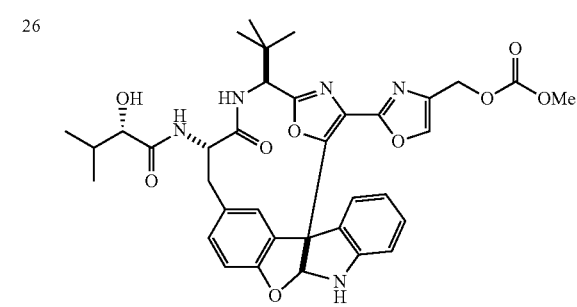

II. Oxazole, 4 oxazoyl analogs with alcohol or ketone in position 4

27
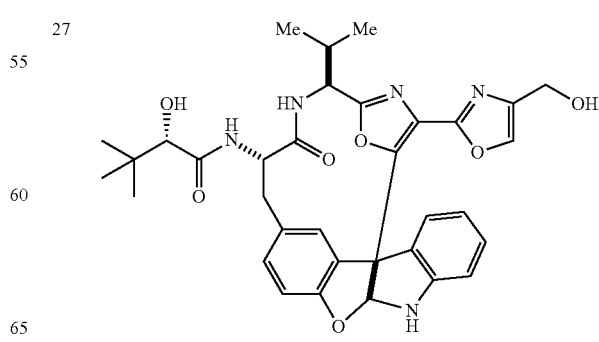

28 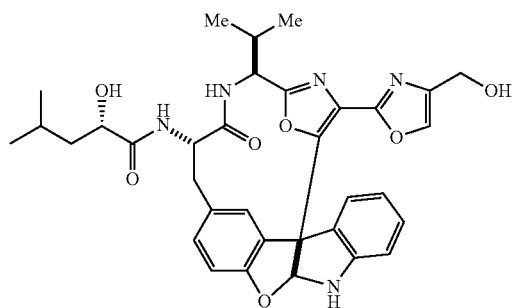
29 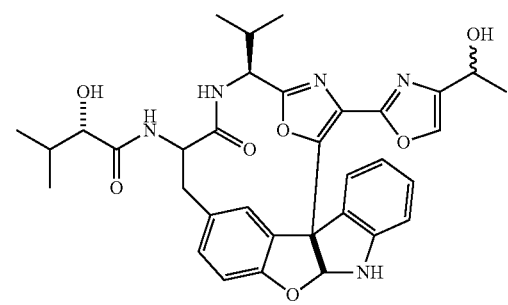
30 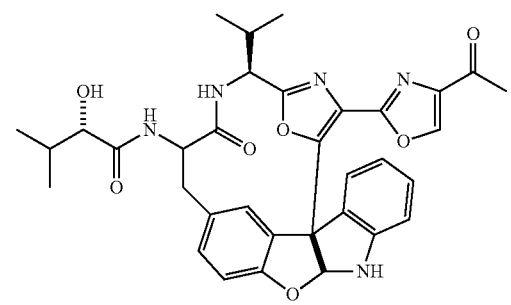
31 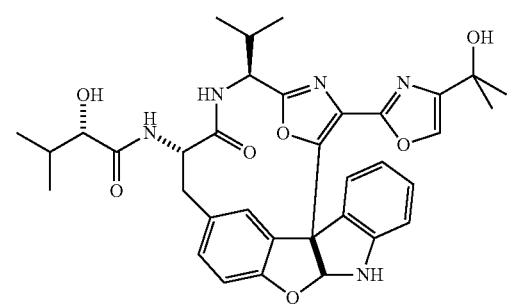
III. Oxazole, 4 oxazoyl analogs with amide, amine, carbamate or sulfonamide in position 4
32 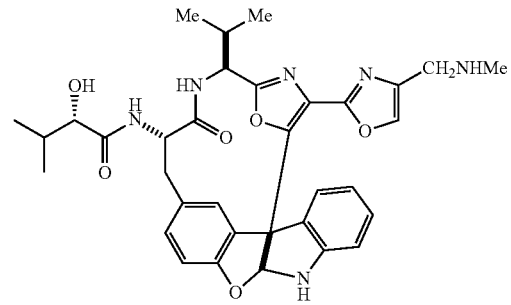
33 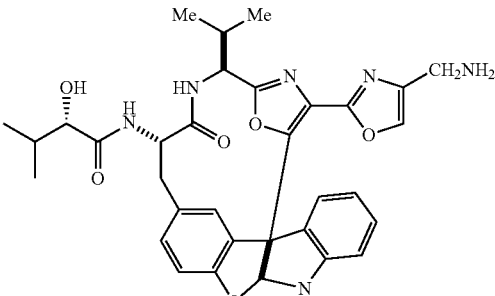
34 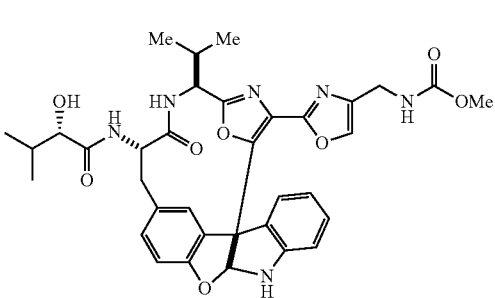
35 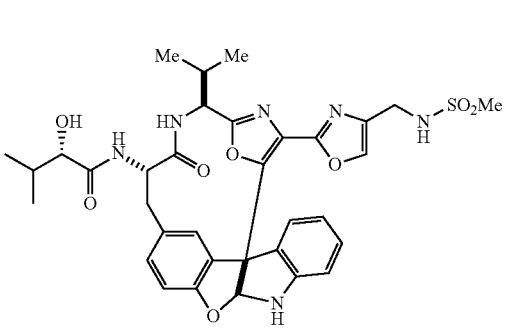
36 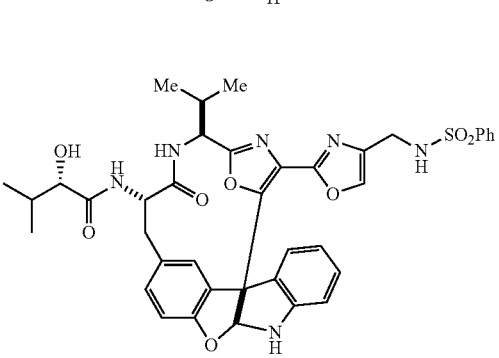
37 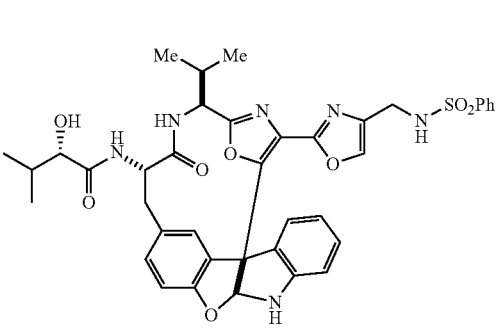

IV. Oxazole, 4 oxazoyl analogs with cyano-group in position 4
38
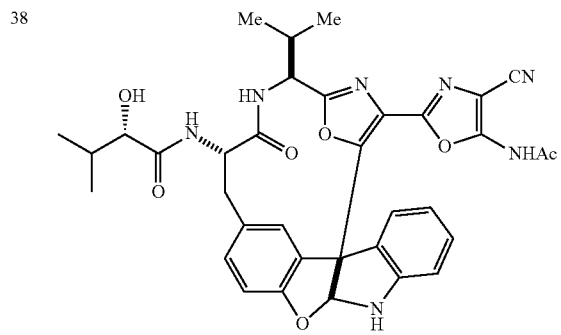
39
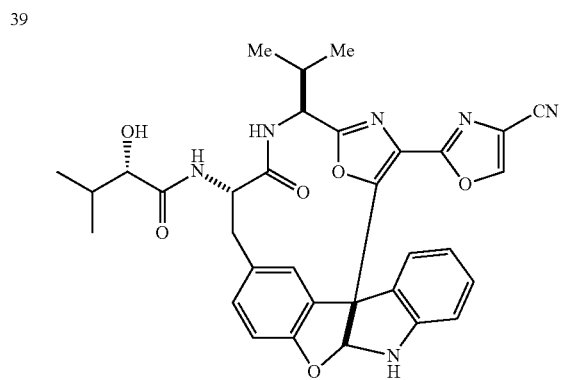
40
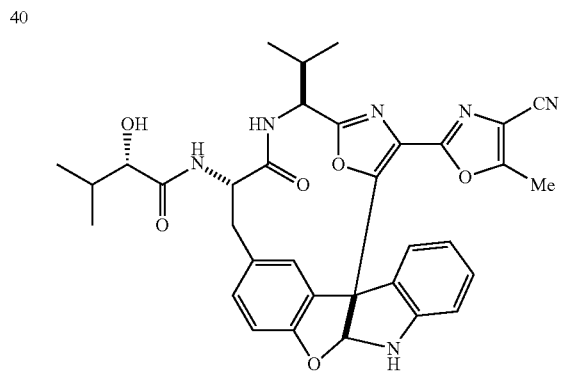
V. Oxazole, 4 oxazoyl analogs with heterocycles in position 4
41
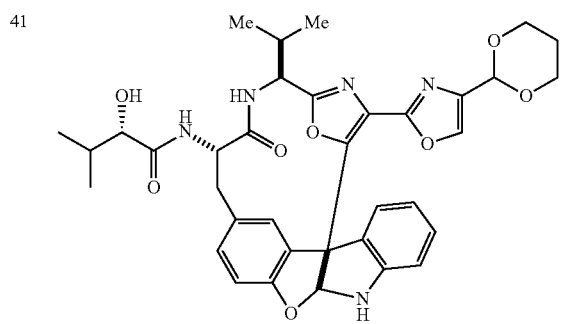
42
43
44
45
46
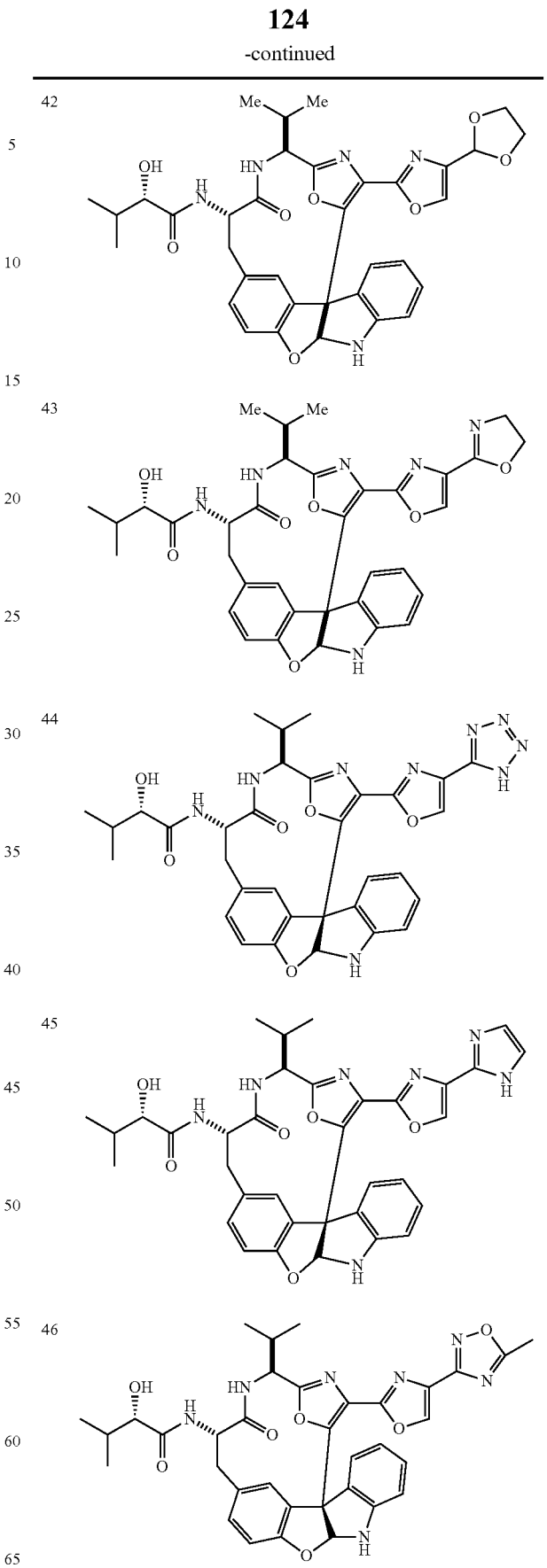

| 125 -continued | 126 -continued |
|---|---|
| 47 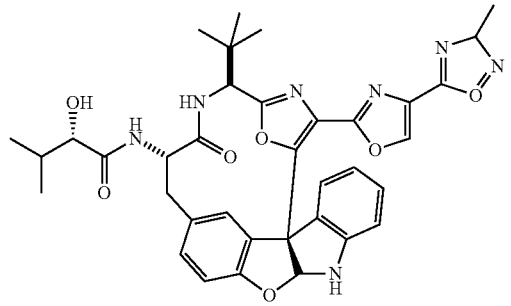 | 52 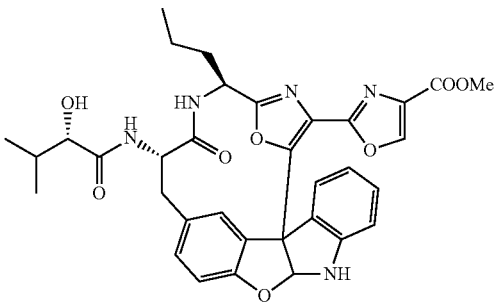 |
| 48 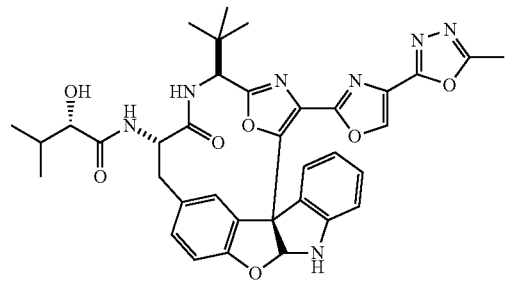 | 53 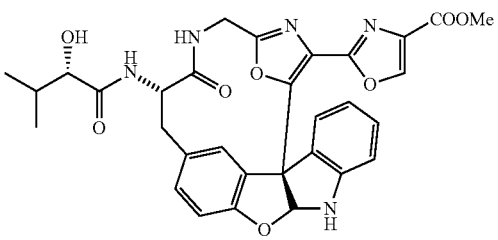 |
| VI. Oxazole, 4 oxazoyl analogs with substituents replacing isopropyl group | |
| 49 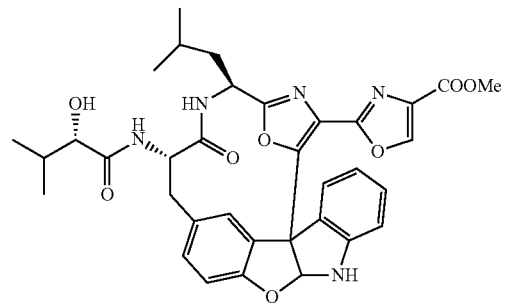 [SMILES: COC(=O)c1coc(C2=C3OC(=N2)[C@H](CC(C)C)NC(=O)[C@@H](NC(=O)[C@@H](O)C(C)C)Cc2ccc4c(c2)C32c3ccccc3NC2O4)n1] | 54 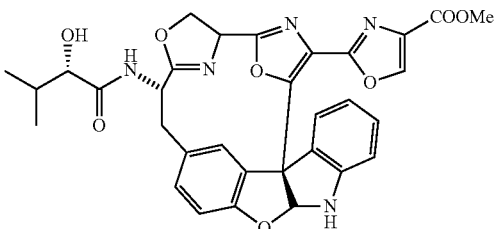 |
| | 55 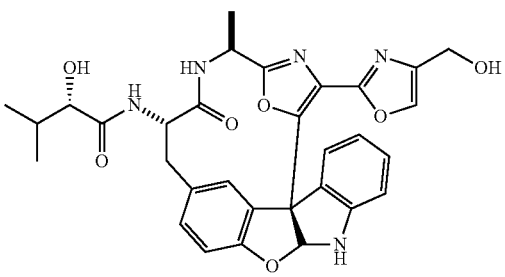 |
| 50 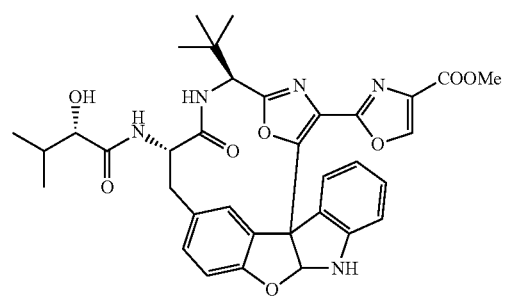 [SMILES: COC(=O)c1coc(C2=C3OC(=N2)[C@H](C(C)(C)C)NC(=O)[C@@H](NC(=O)[C@@H](O)C(C)C)Cc2ccc4c(c2)C32c3ccccc3NC2O4)n1] | 56 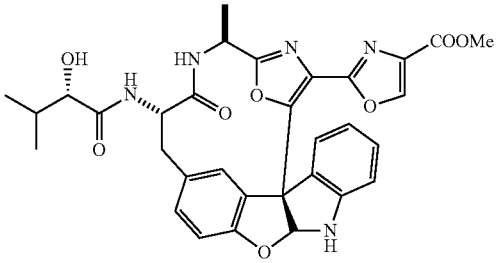 |
| 51 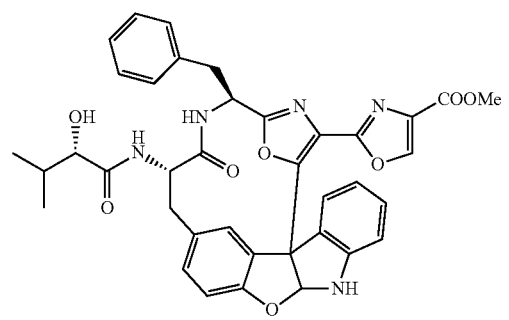 [SMILES: COC(=O)c1coc(C2=C3OC(=N2)[C@H](Cc2ccccc2)NC(=O)[C@@H](NC(=O)[C@@H](O)C(C)C)Cc2ccc4c(c2)C32c3ccccc3NC2O4)n1] | 57 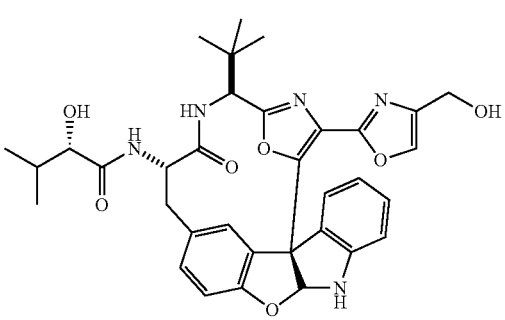 |

| 127 -continued | 128 -continued |
|---|---|
| 58 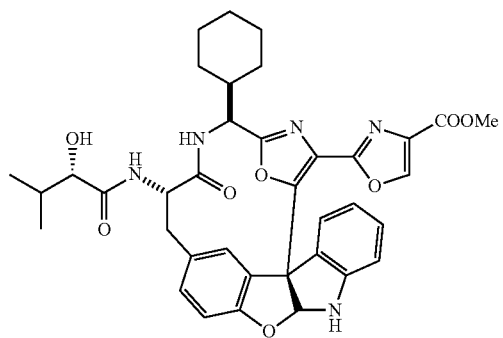 | 62 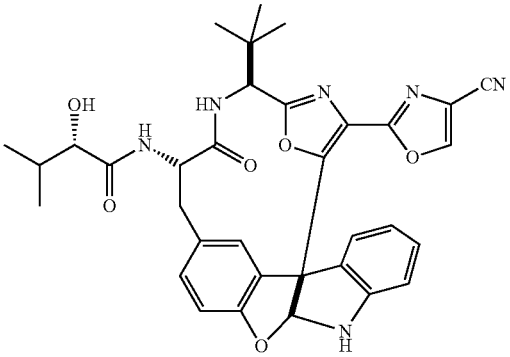 |
| 59 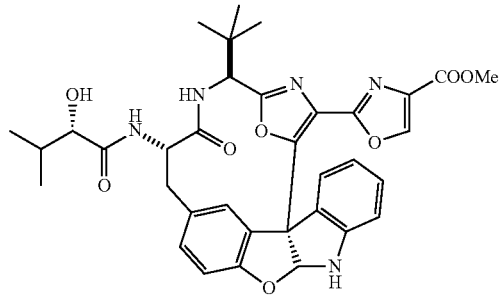 | 63 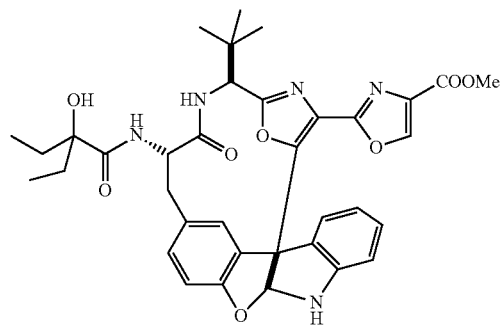 |
| 60 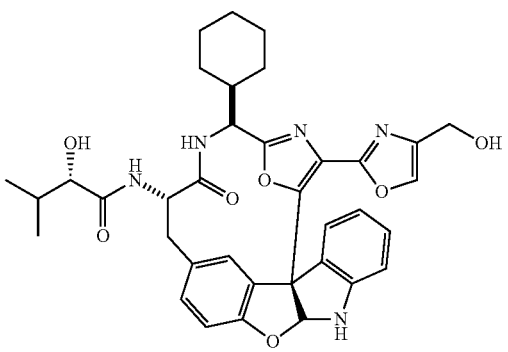 | 64 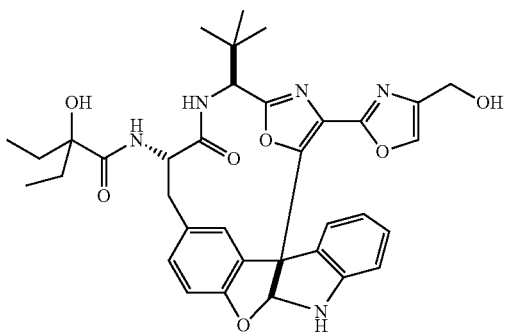 |
| 61 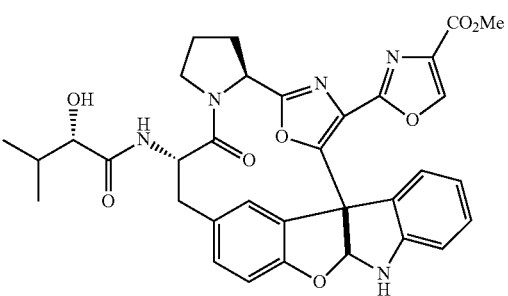 | 65 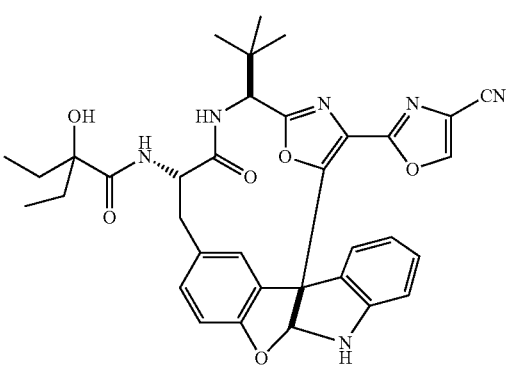 |

| 66 | 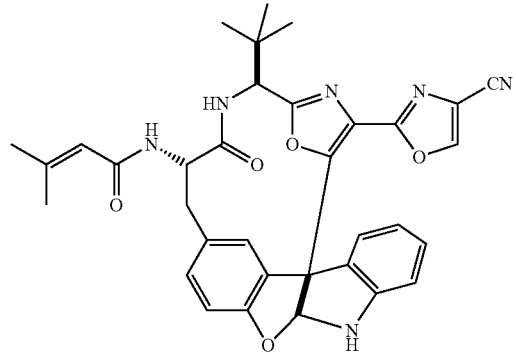 |
|---|---|
| 67 | 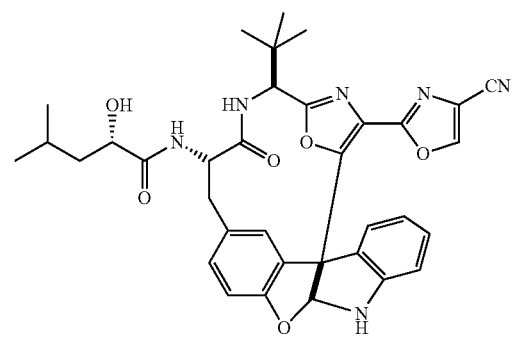 |
| 68 | 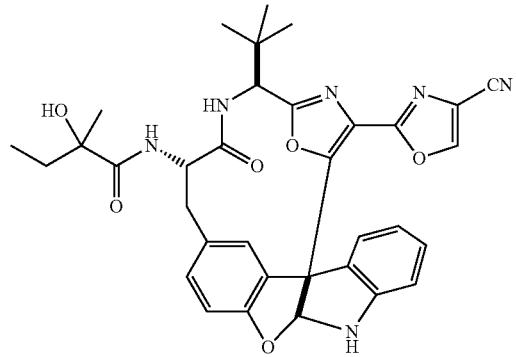 |
| 69 | 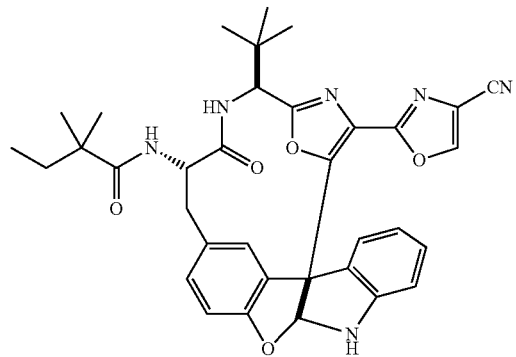 |
VII. Oxazole, 4 oxazoyl analogs with variations in tyrosine moiety
| 70 | 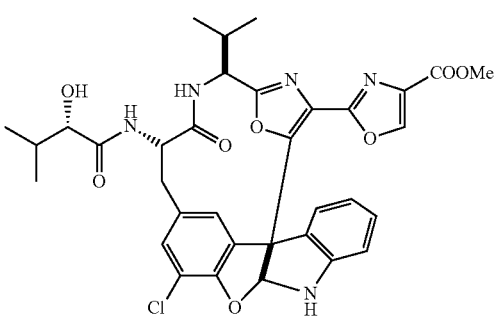 |
|---|---|
| 71 | 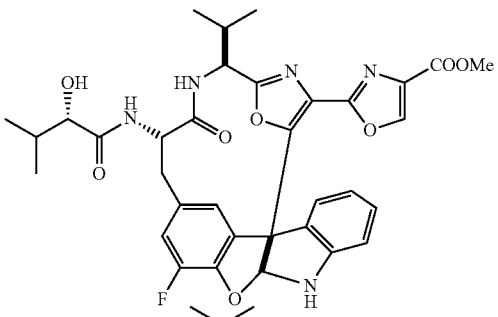 |
| 72 | 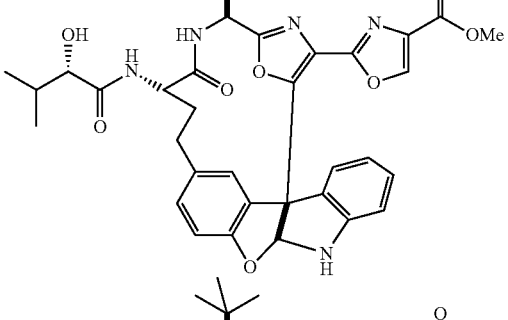 |
| 73 | 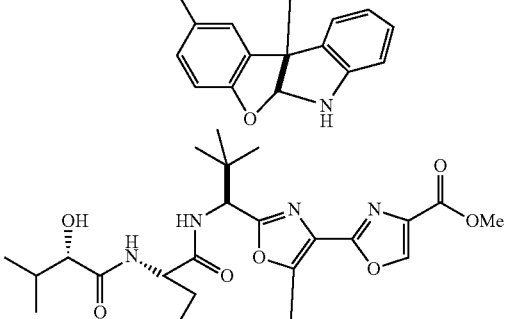 |
| 74 | 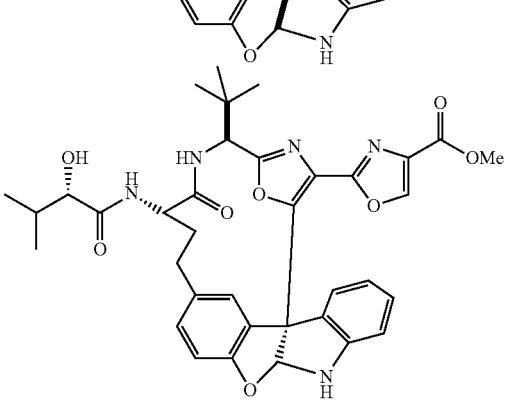 |

75 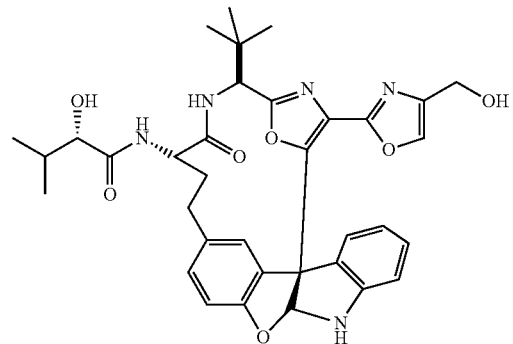
VIII. Oxazole, 4 oxazoyl analogs with variations in indoline moiety
76 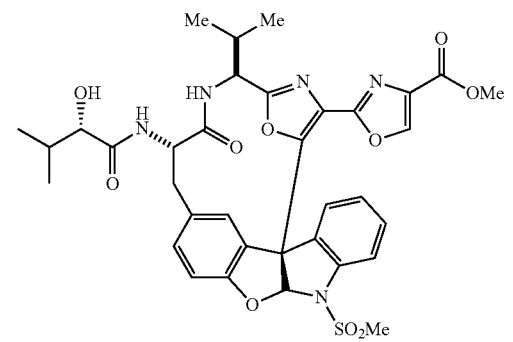
77 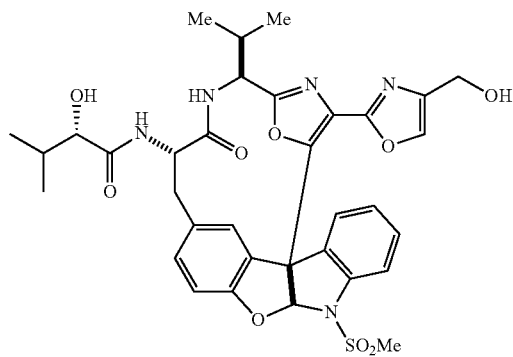
78 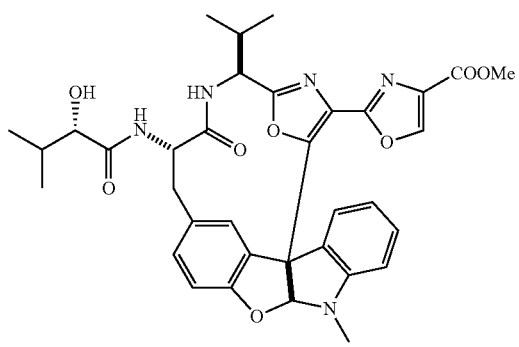
79 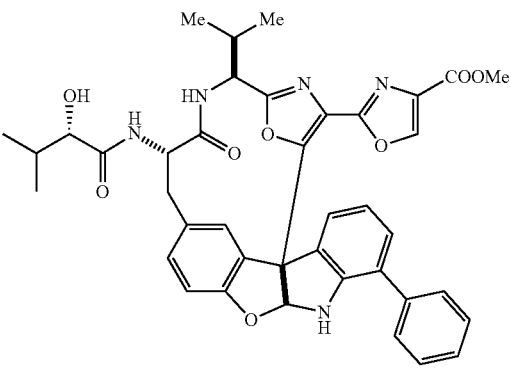
80 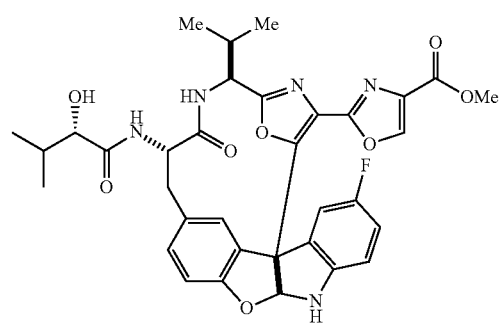
81 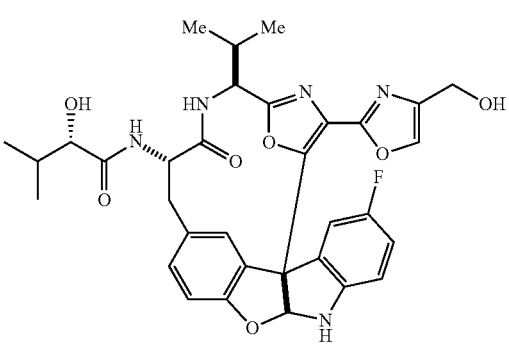
82 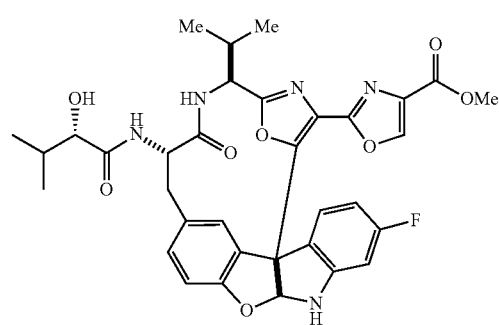

83 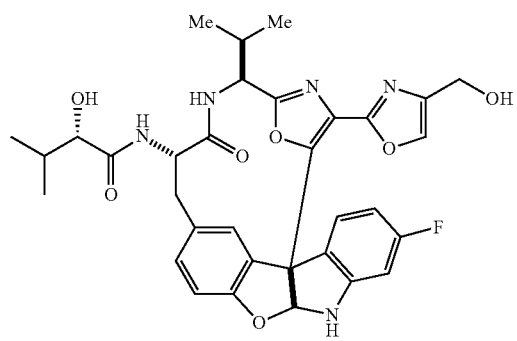
84 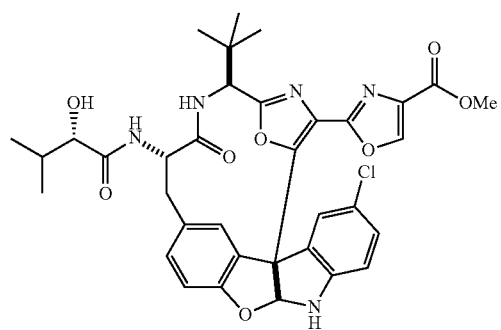
85 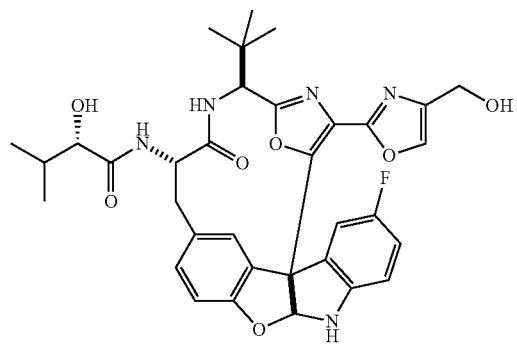
86 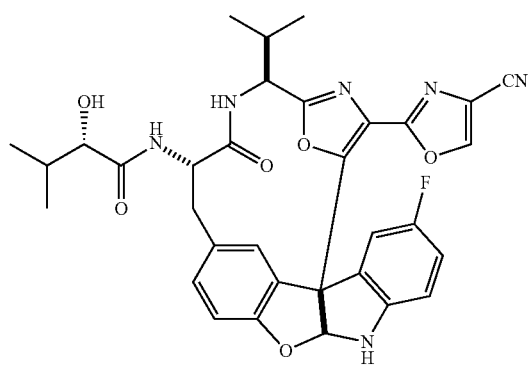
87 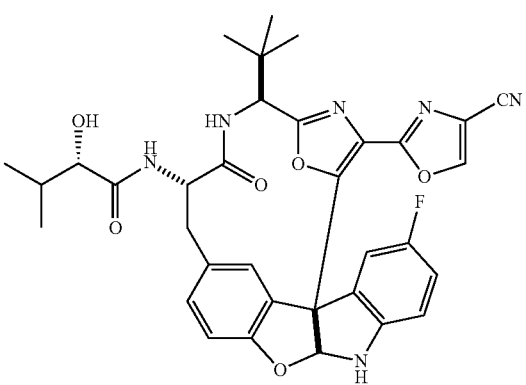
IX. Oxazole, 4 oxazoyl analogs with N-Methyl group in side chain and/or macrocyclic moiety
88 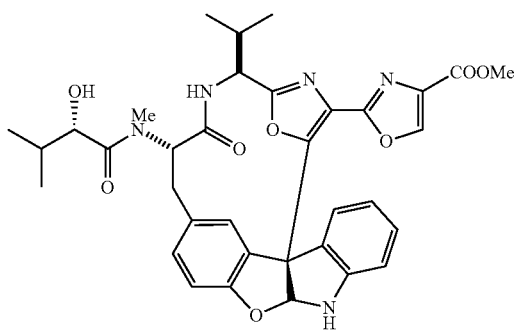
89 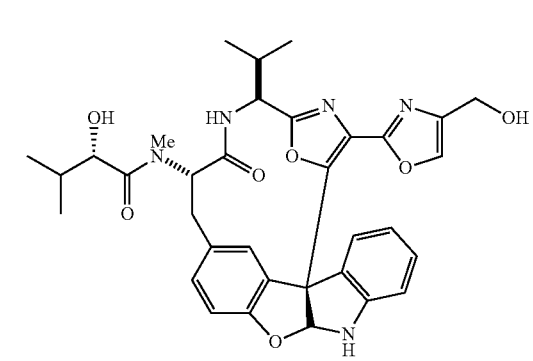
90 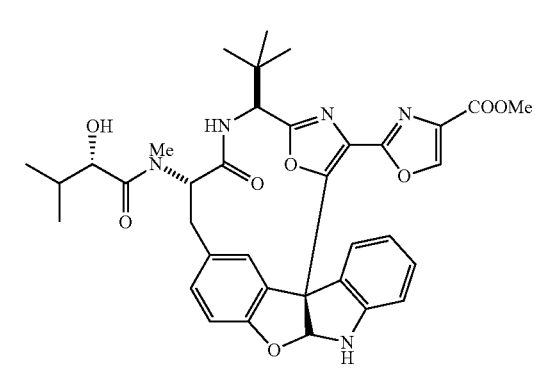

91 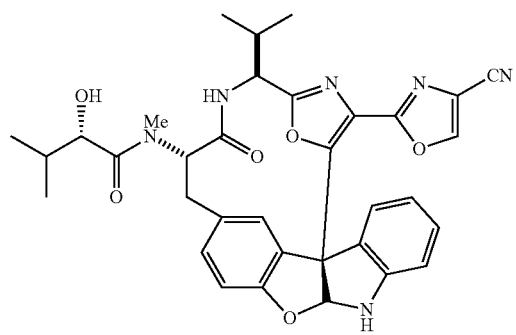
92 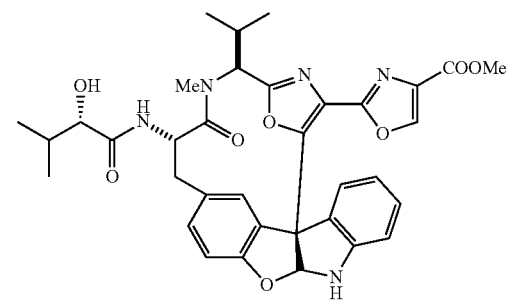
93 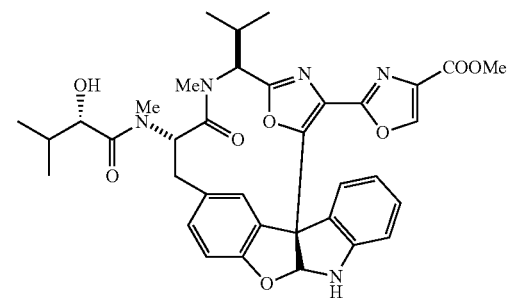
94 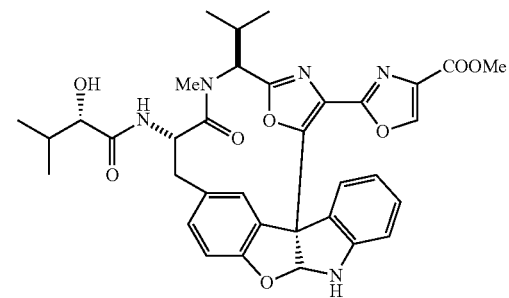
X. Oxazole, 4-aryl (non-oxazole) analogs
95 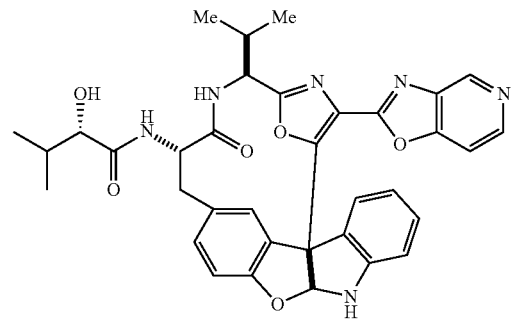
96 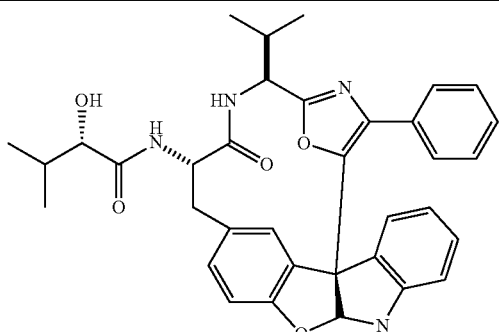
97 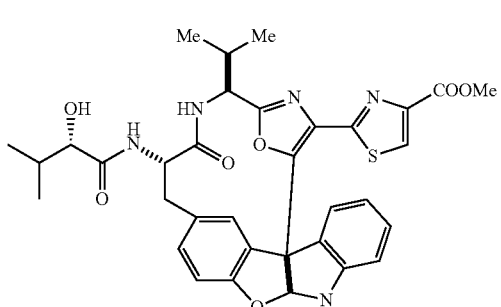
98 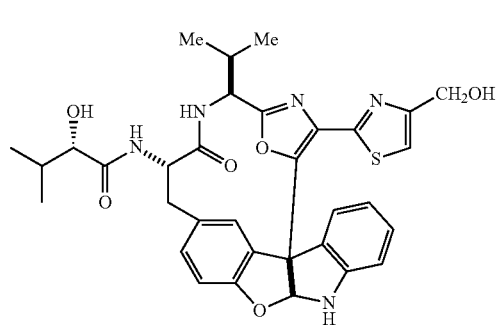
XI. Oxazole, 4 oxazoyl analogs
99 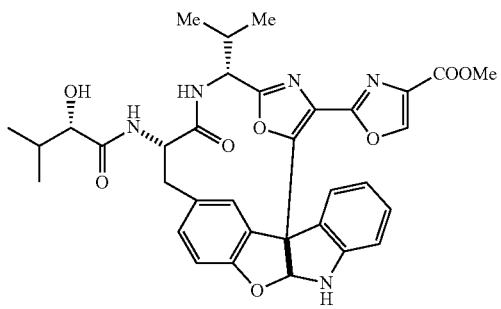
100 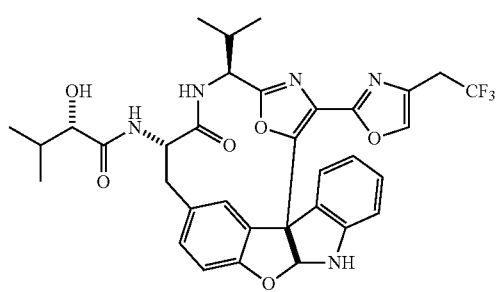

101 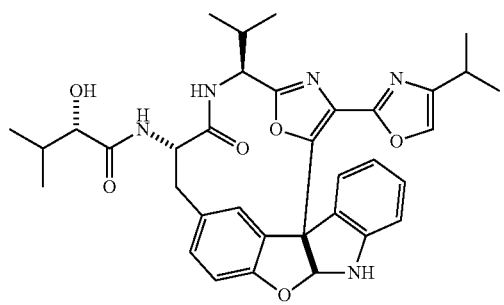
102 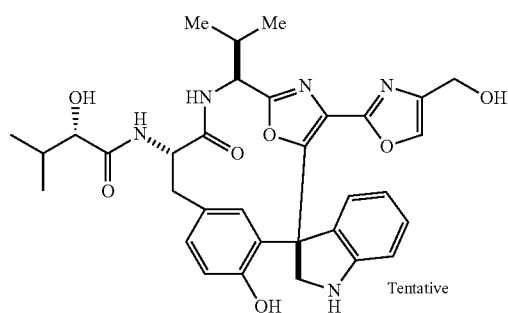
Tentative
103 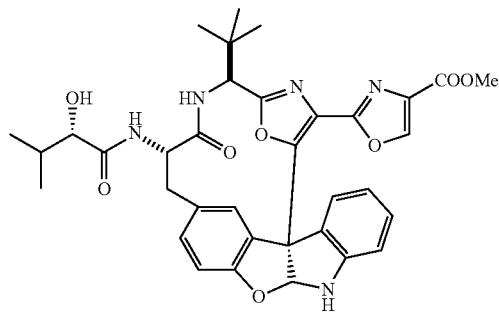
104 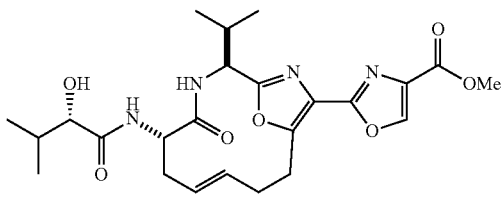
105 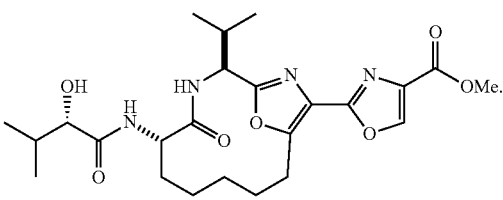
2. A compound of claim 1 and of the following table, or a pharmaceutically acceptable salt thereof:
I. Oxazole, 4 oxazoyl analogs with esters other than methyl ester in position 4.
21 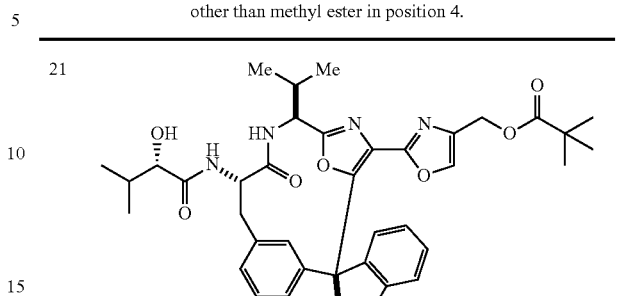
22 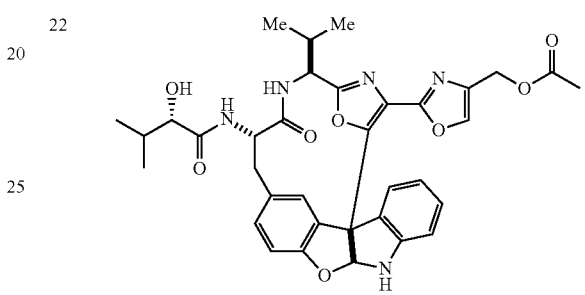
23 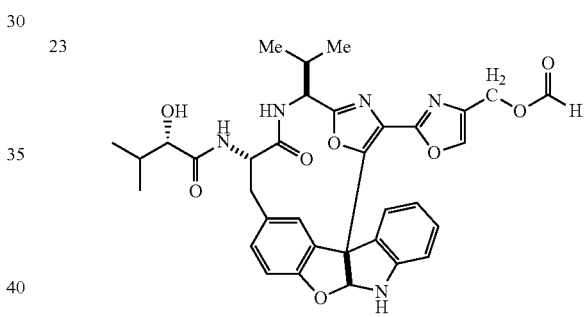
24 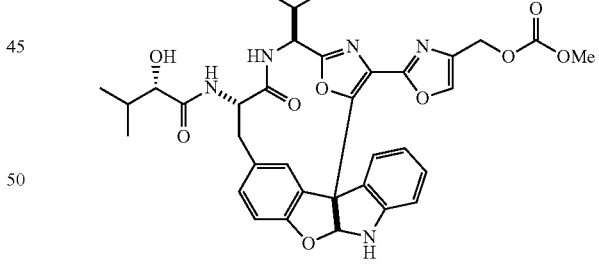
25 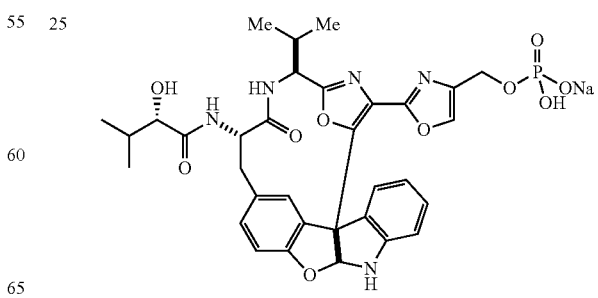

I. Oxazole, 4 oxazoyl analogs with esters other than methyl ester in position 4.

26
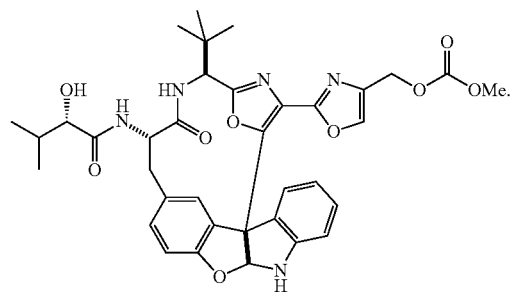

3. A compound of claim 1 and of the following table, or a pharmaceutically acceptable salt thereof:

II. Oxazole, 4 oxazoyl analogs with alcohol or ketone in position 4

27
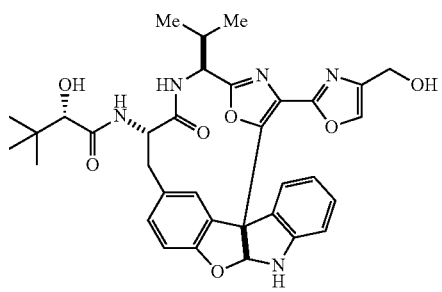

28
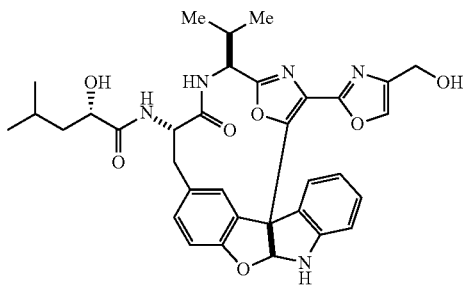

29
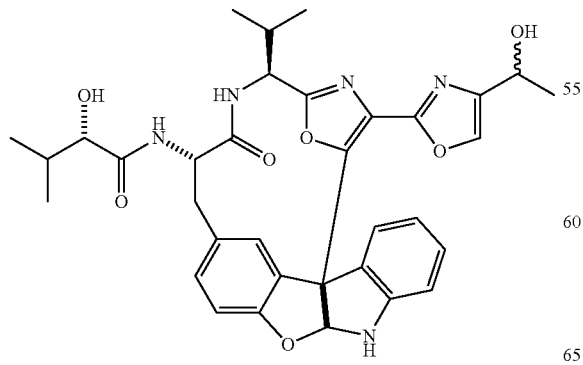

II. Oxazole, 4 oxazoyl analogs with alcohol or ketone in position 4

30
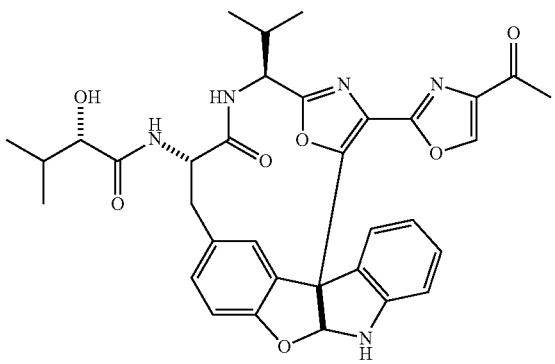

31
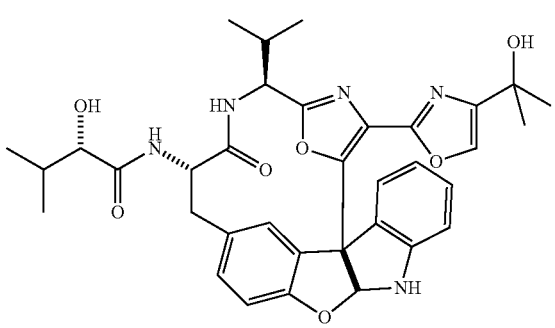

4. A compound of claim 1 and of the following table, or a pharmaceutically acceptable salt thereof:

32
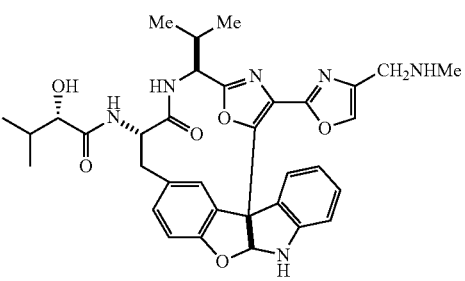

33
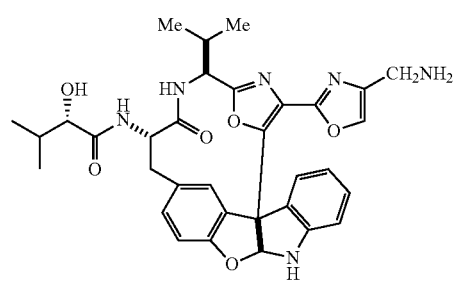

| 34 | 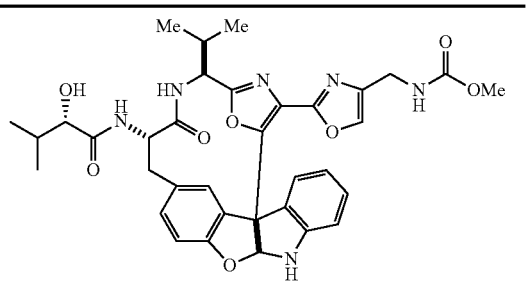 |
| --- | --- |
| 35 | 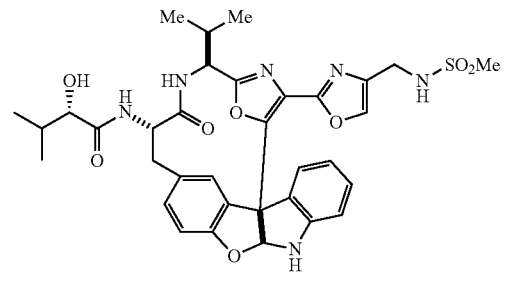 |
| 36 | 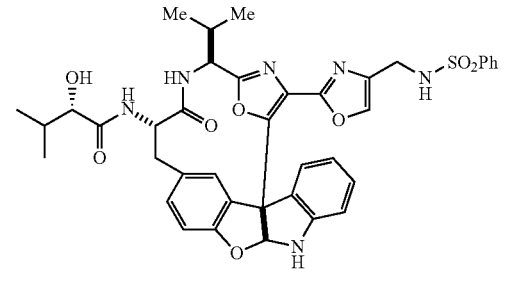 |
| 37 | 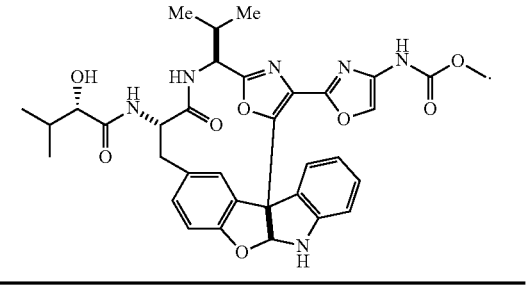 |
5. A compound of claim 1 and of the following table, or a pharmaceutically acceptable salt thereof:
| IV. Oxazole, 4 oxazoyl analogs with cyano-group in position 4 | |
| --- | --- |
| 38 | 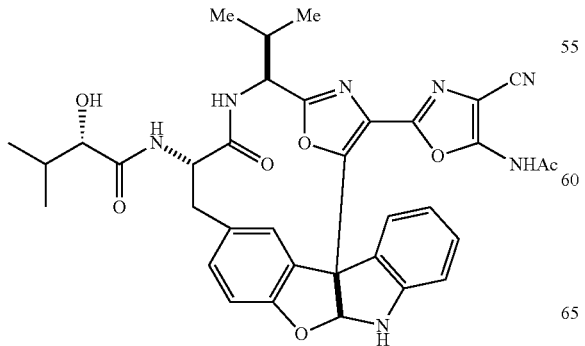 |
| 39 | 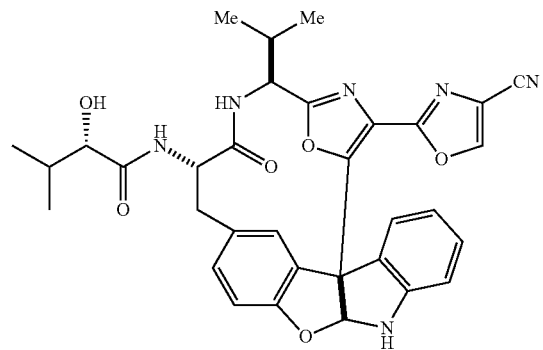 |
| 40 | 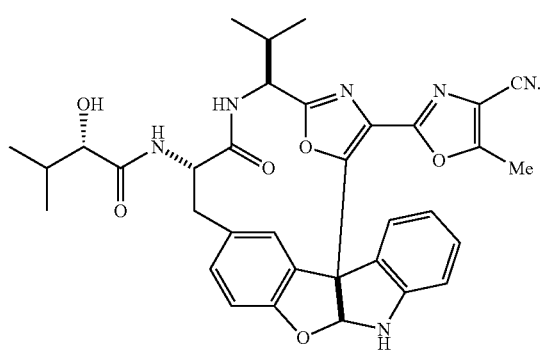 |
6. A compound of claim 1 and of the following table, or a pharmaceutically acceptable salt thereof:
| V. Oxazole, 4 oxazoyl analogs with heterocycles in position 4 | |
| --- | --- |
| 41 | 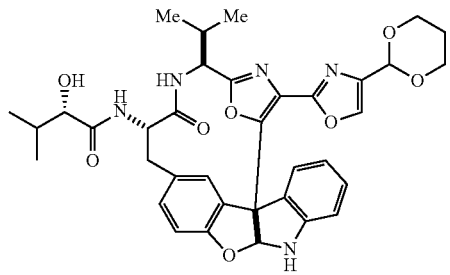 |
| 42 | 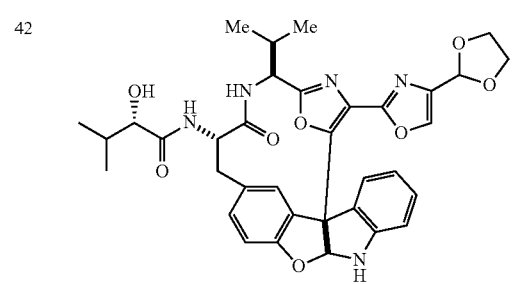 |

V. Oxazole, 4 oxazoyl analogs with heterocycles in position 4
43
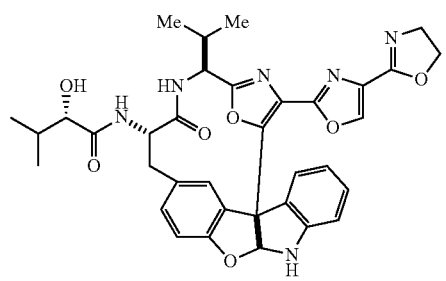
44
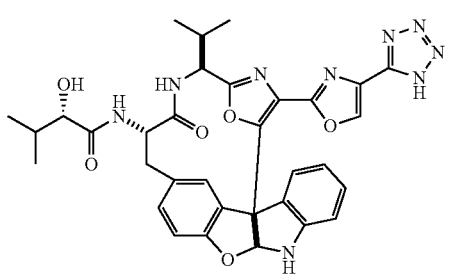
45
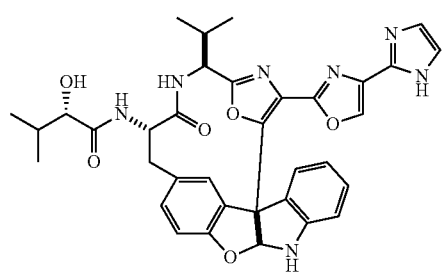
46
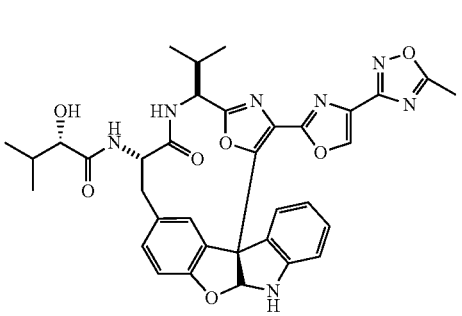
47
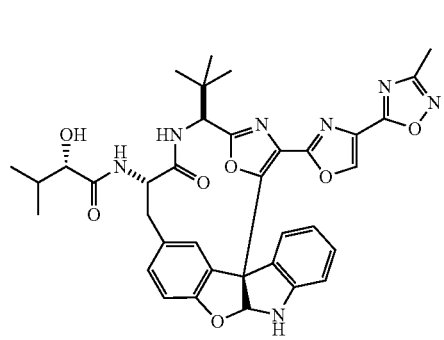
V. Oxazole, 4 oxazoyl analogs with heterocycles in position 4
48
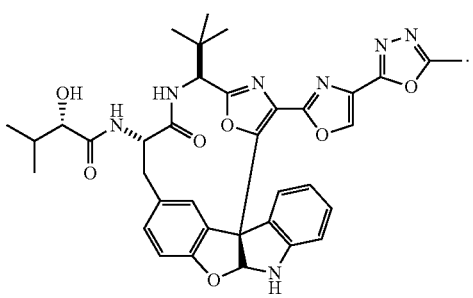
7. A compound of claim 1 and of the following table, or a pharmaceutically acceptable salt thereof:
VI. Oxazole, 4 oxazoyl analogs with substituents replacing isopropyl group
49
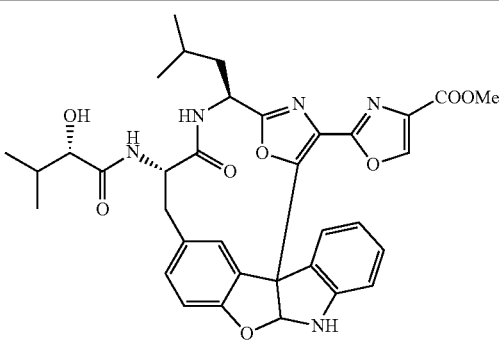 [SMILES: COC(=O)c1coc(C2=C3OC(=N2)[C@H](CC(C)C)NC(=O)[C@@H](NC(=O)[C@@H](O)C(C)C)Cc2ccc4c(c2)C32c3ccccc3NC2O4)n1]
50
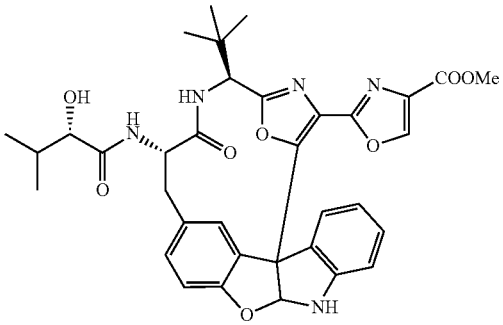 [SMILES: COC(=O)c1coc(C2=C3OC(=N2)[C@H](C(C)(C)C)NC(=O)[C@@H](NC(=O)[C@@H](O)C(C)C)Cc2ccc4c(c2)C32c3ccccc3NC2O4)n1]
51
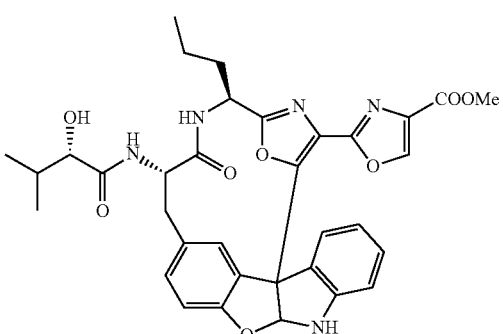

VI. Oxazole, 4 oxazoyl analogs with substituents replacing isopropyl group
52
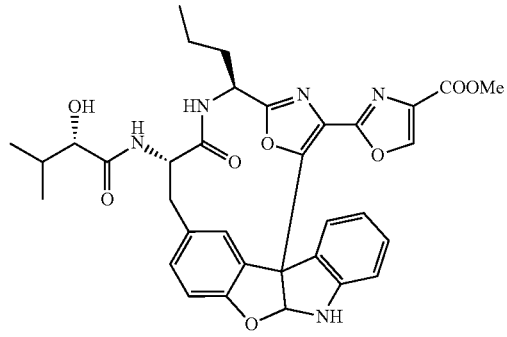 [SMILES: CCC[C@@H]1NC(=O)[C@@H](NC(=O)[C@@H](O)C(C)C)Cc2ccc3c(c2)C2(C4=C(c5nc(C(=O)OC)co5)N=C1O4)c1ccccc1NC2O3]
53
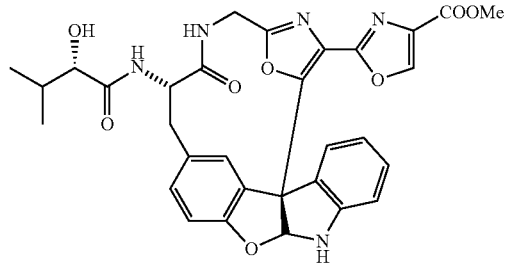
54
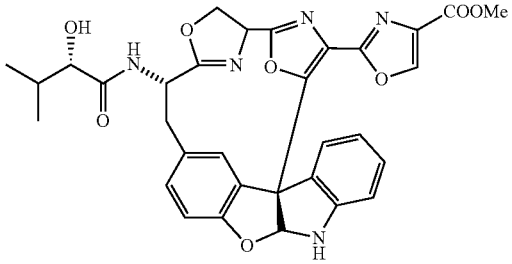
55
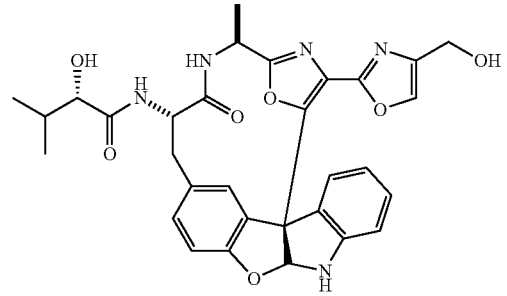
56
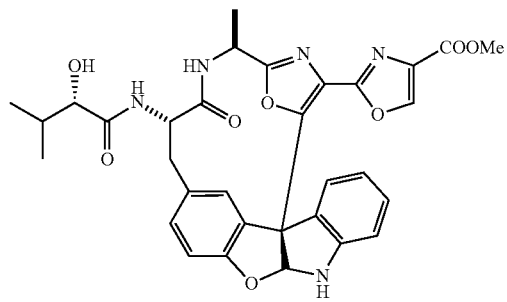
VI. Oxazole, 4 oxazoyl analogs with substituents replacing isopropyl group
57
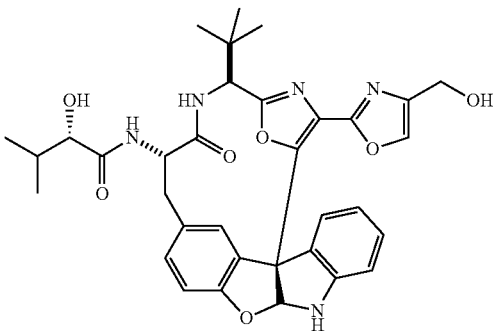
58
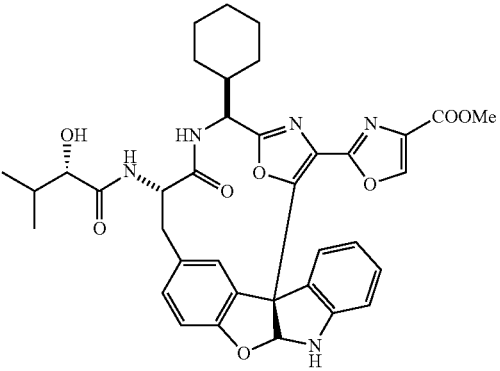
59
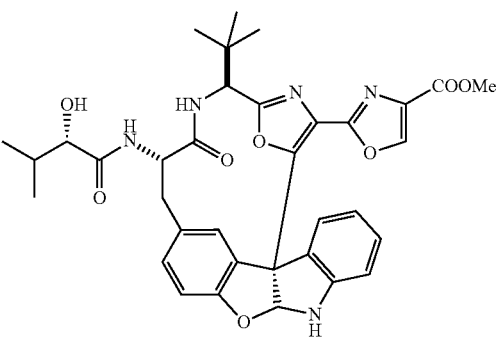
60
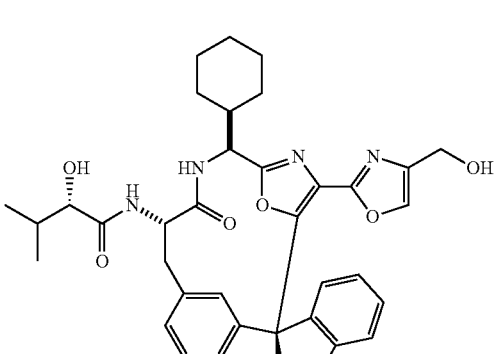
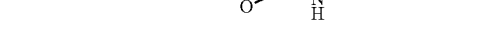

| VI. Oxazole, 4 oxazoyl analogs with substituents replacing isopropyl group | VI. Oxazole, 4 oxazoyl analogs with substituents replacing isopropyl group |
|---|---|
| 61 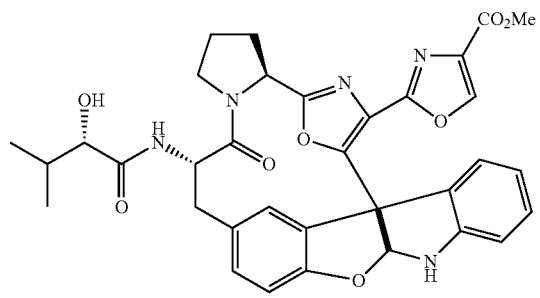 | 65 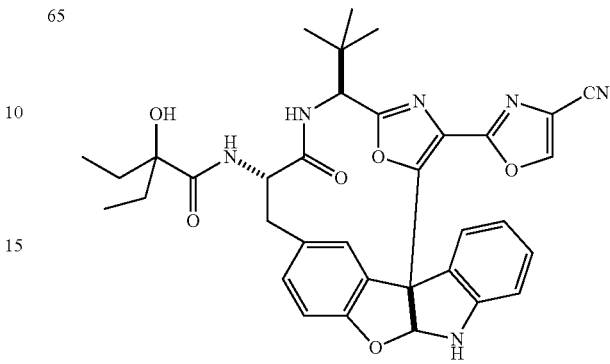 |
| 62 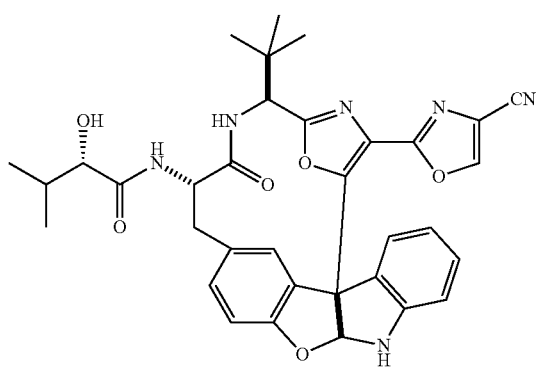 | 66 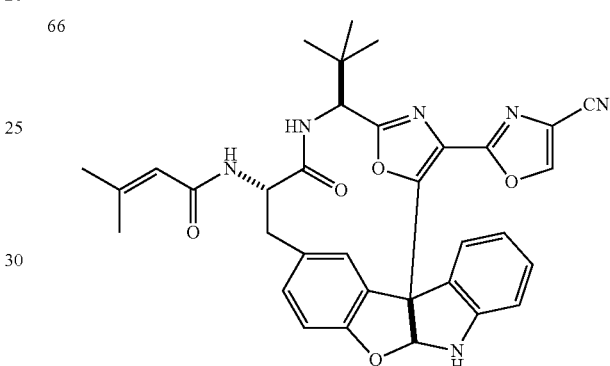 |
| 63 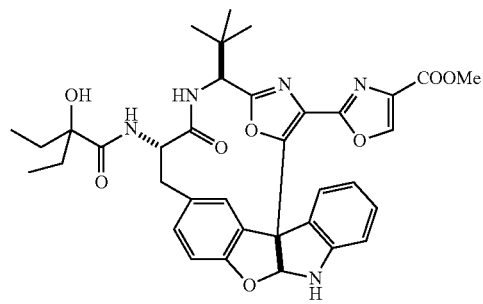 | 67 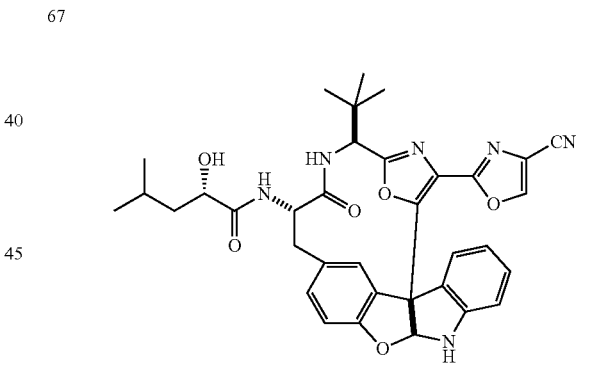 |
| 64 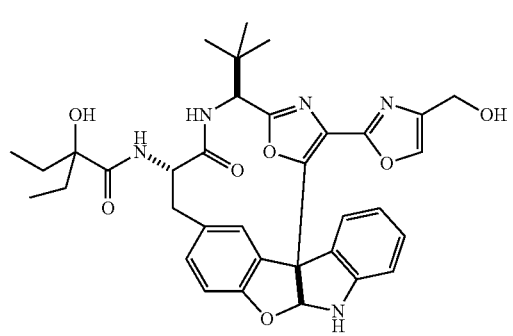 | 68 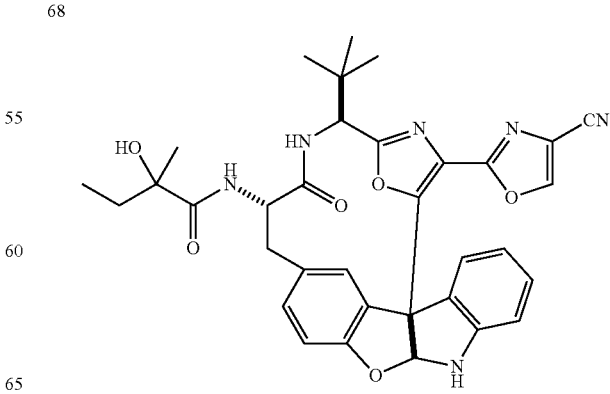 |

VI. Oxazole, 4 oxazoyl analogs with substituents replacing isopropyl group

69

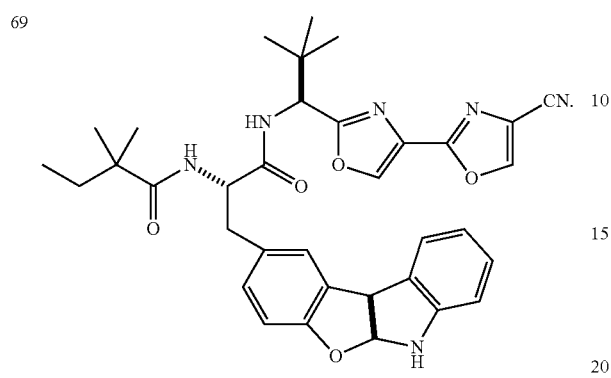

8. A compound of claim 1 and of the following table, or a pharmaceutically acceptable salt thereof:

VII. Oxazole, 4 oxazoyl analogs with variations in tyrosine moiety

70

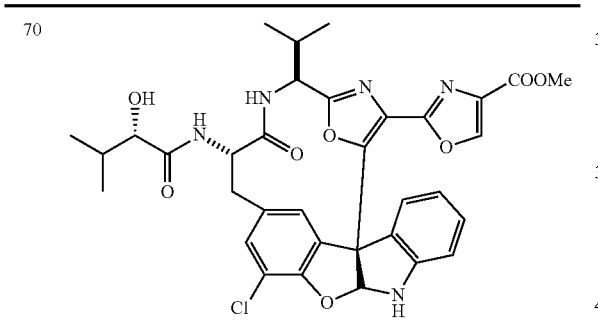

71

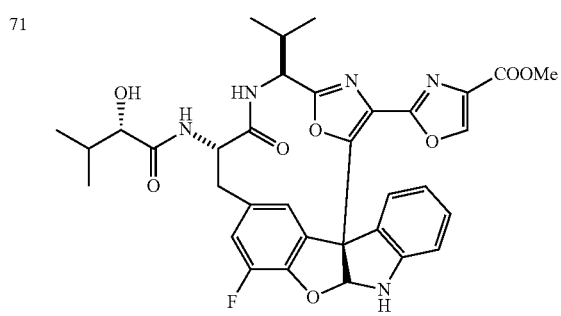

72

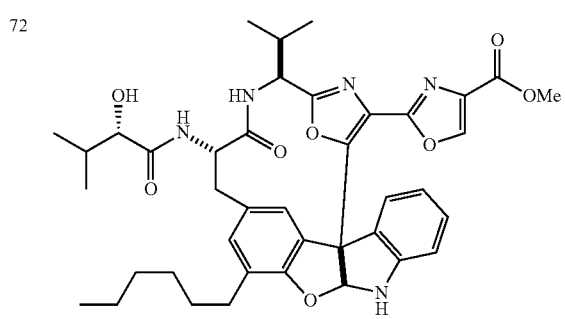

VII. Oxazole, 4 oxazoyl analogs with variations in tyrosine moiety

73

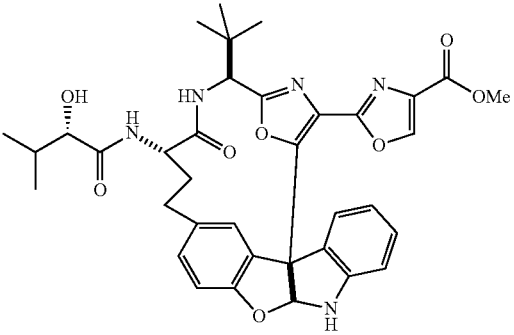

74

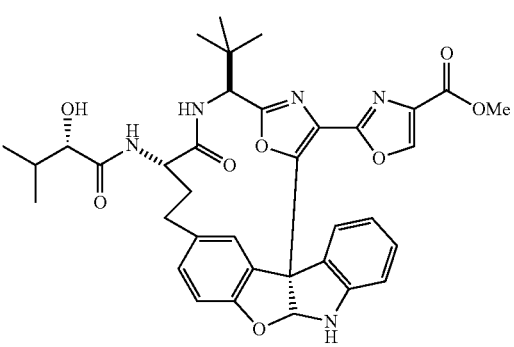

75

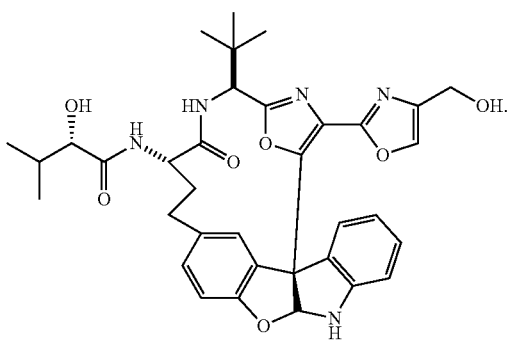

9. A compound of claim 1 and of the following table, or a pharmaceutically acceptable salt thereof:

VIII. Oxazole, 4 oxazoyl analogs with variations in indoline moiety

76

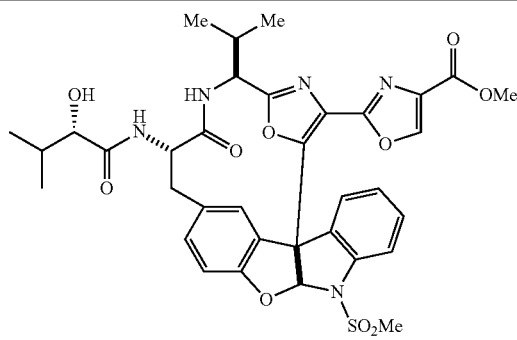

| VIII. Oxazole, 4 oxazoyl analogs with variations in indoline moiety | VIII. Oxazole, 4 oxazoyl analogs with variations in indoline moiety |
|---|---|
| 77 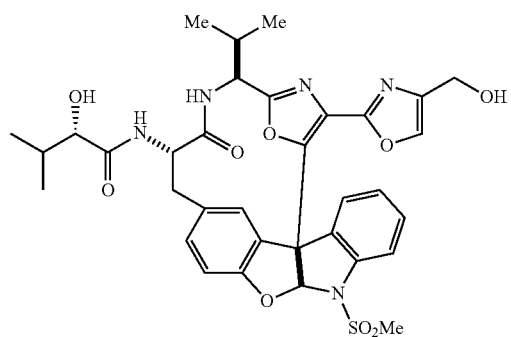 | 81 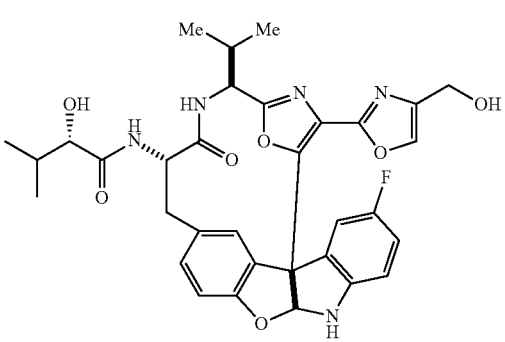 |
| 78 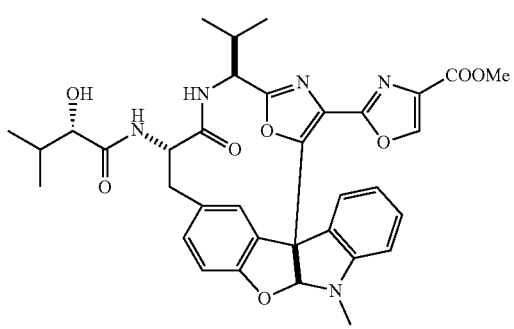 | 82 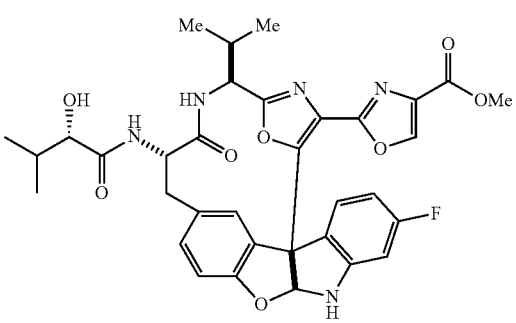 |
| 79 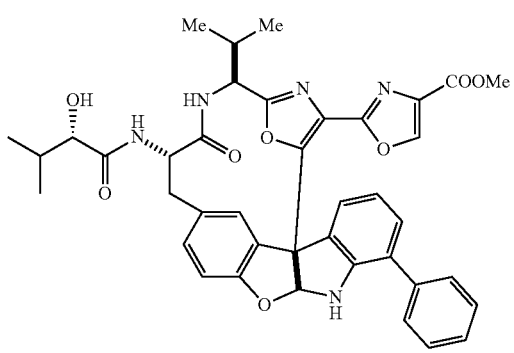 | 83 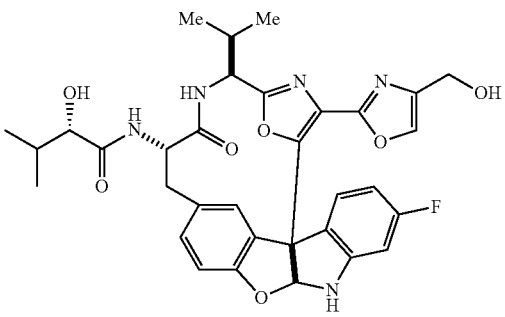 |
| 80 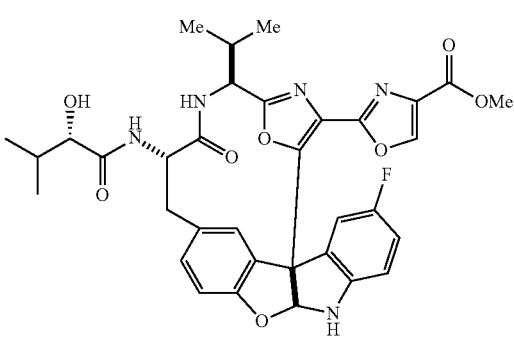 | 84 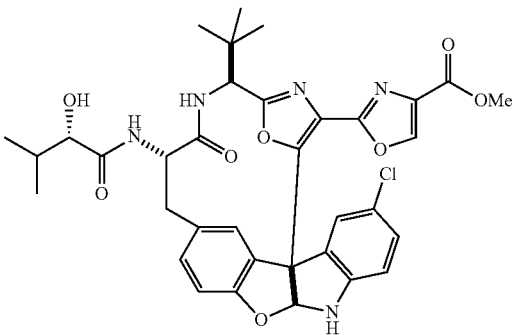 |

| | |
|---|---|
| VIII. Oxazole, 4 oxazoyl analogs with variations in indoline moiety | IX. Oxazole, 4 oxazoyl analogs with N-Methyl group in side chain and/or macrocyclic moiety |
| 85 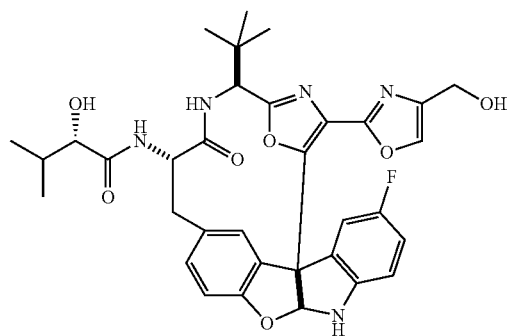 | 89 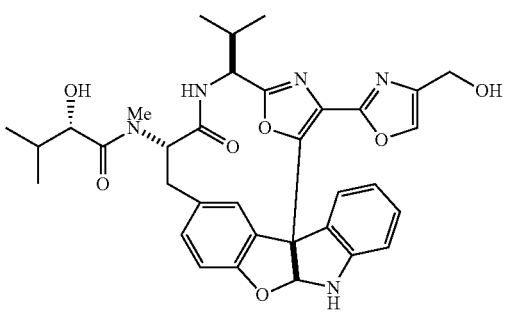 |
| 86 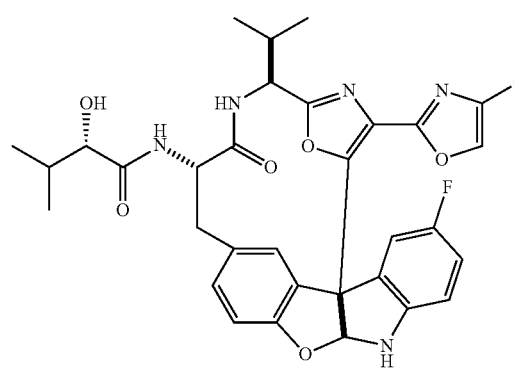 | 90 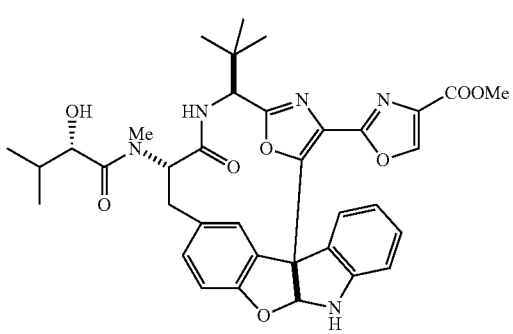 |
| 87 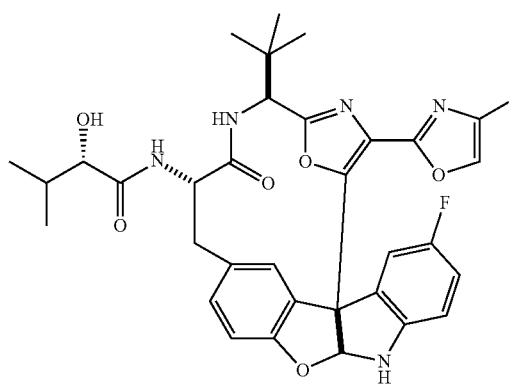 | 91 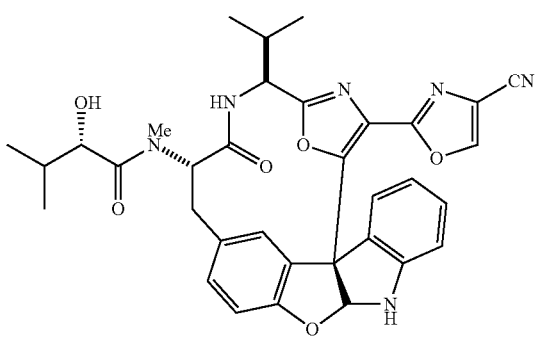 |
| | 92 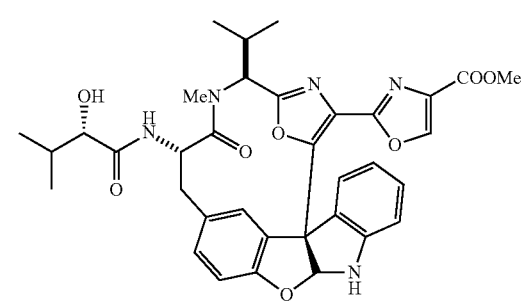 |
10. A compound of claim 1 and of the following table, or a pharmaceutically acceptable salt thereof:
| |
|---|
| IX. Oxazole, 4 oxazoyl analogs with N-Methyl group in side chain and/or macrocyclic moiety |
| 88 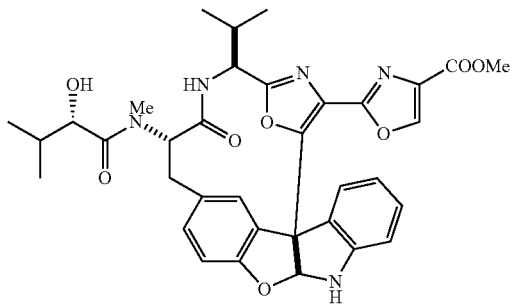 |
| 93 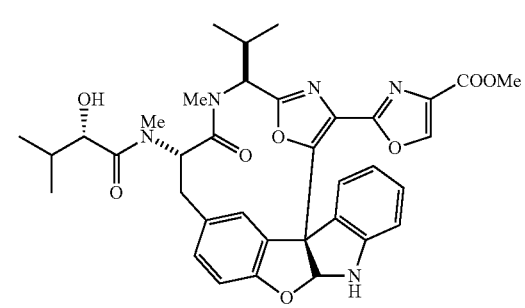 |

IX. Oxazole, 4 oxazoyl analogs with N-Methyl group in side chain and/or macrocyclic moiety

94

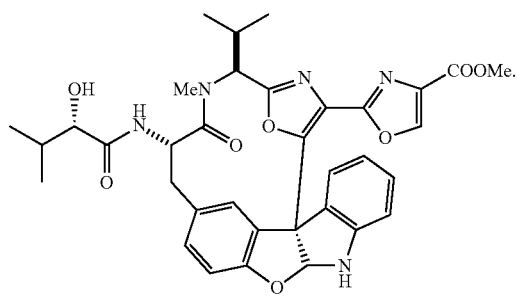

11. A compound of claim 1 and of the following table, or a pharmaceutically acceptable salt thereof:

X. Oxazole, 4-aryl (non-oxazole) analogs

95

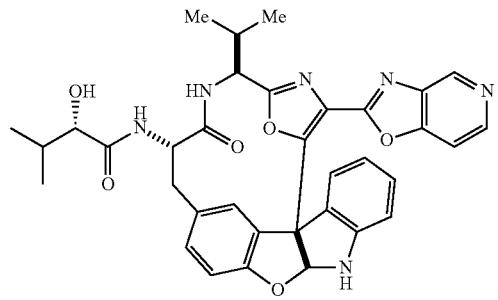

96

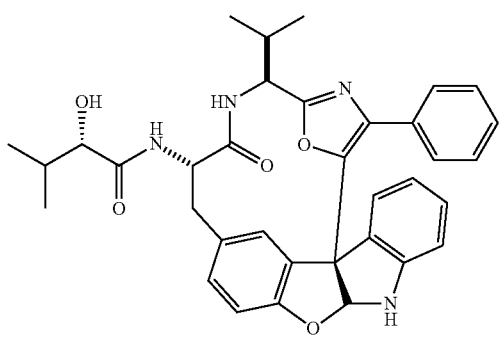

97

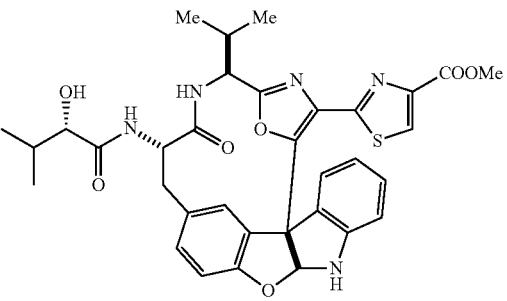

X. Oxazole, 4-aryl (non-oxazole) analogs

98

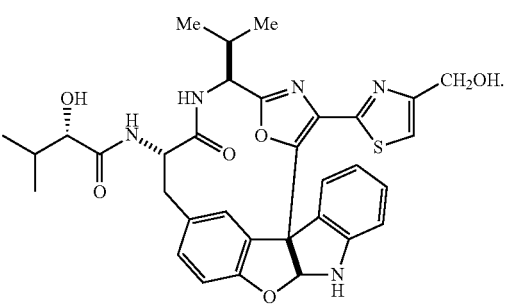

12. A compound of claim 1 and of the following table, or a pharmaceutically acceptable salt thereof:

XI. Oxazole, 4 oxazoyl analogs

99

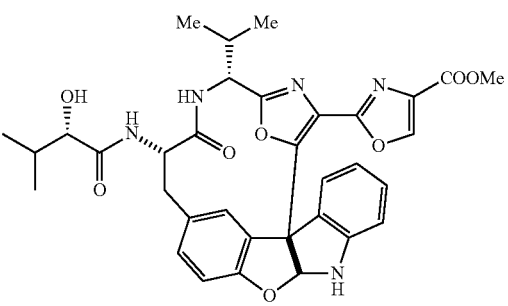

100

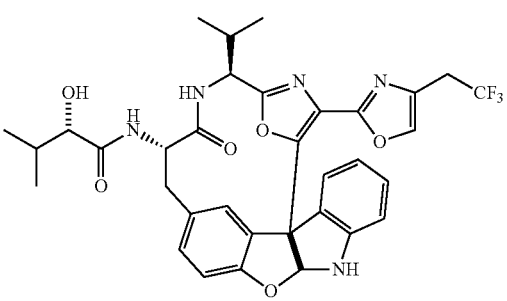

101

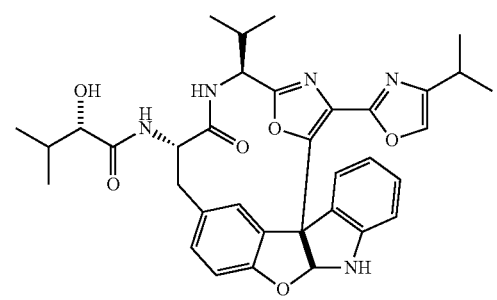

XI. Oxazole, 4 oxazoyl analogs
102
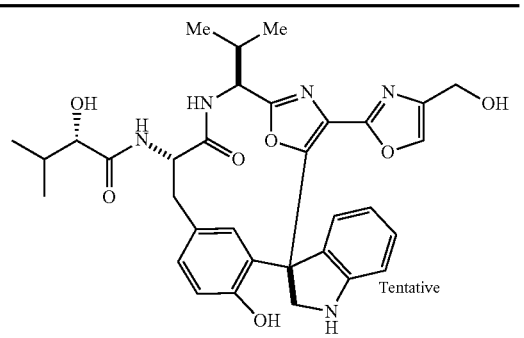
103
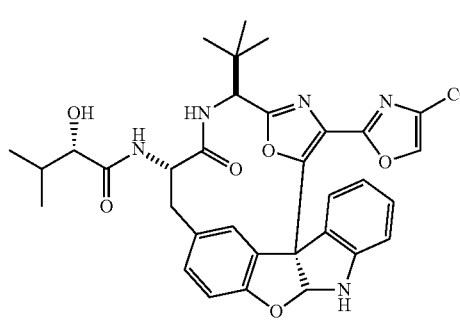
104
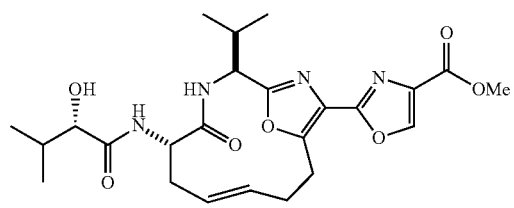
105
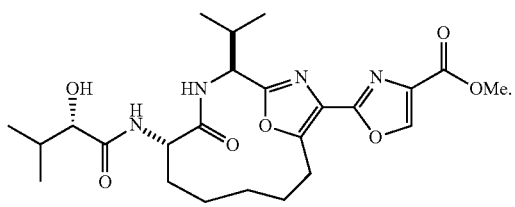
13. A compound of claim 1 and of the following table, or a pharmaceutically acceptable salt thereof:
81
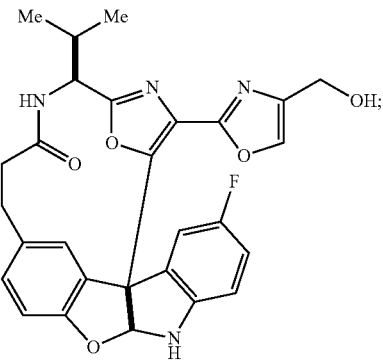
87
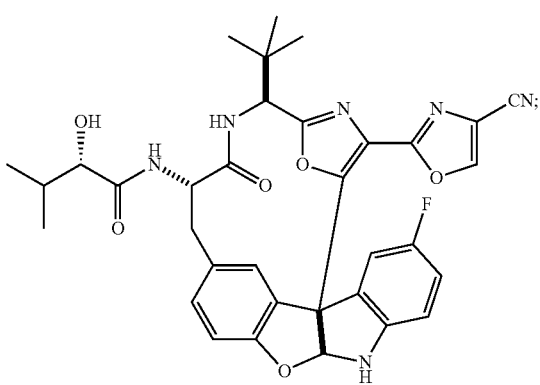
85
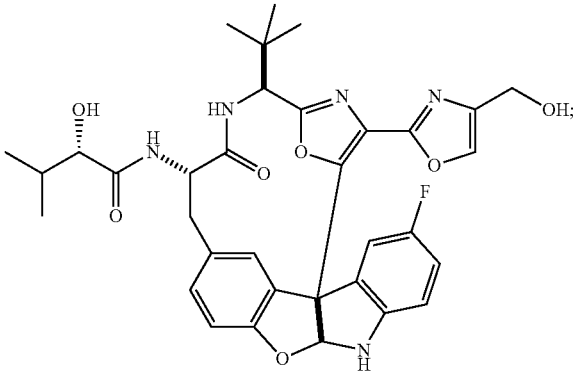
86
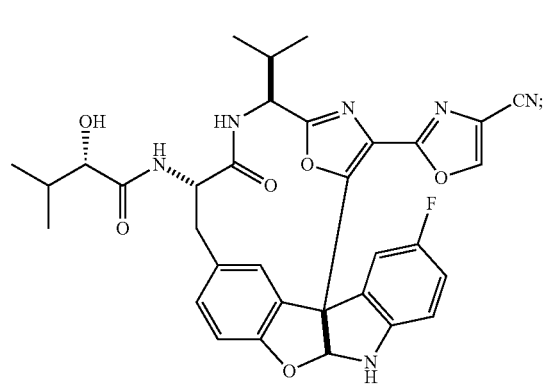
62
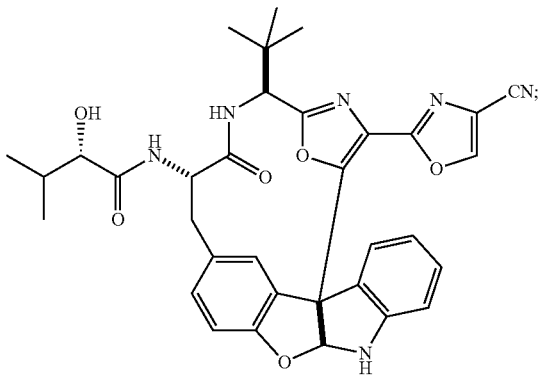

-continued

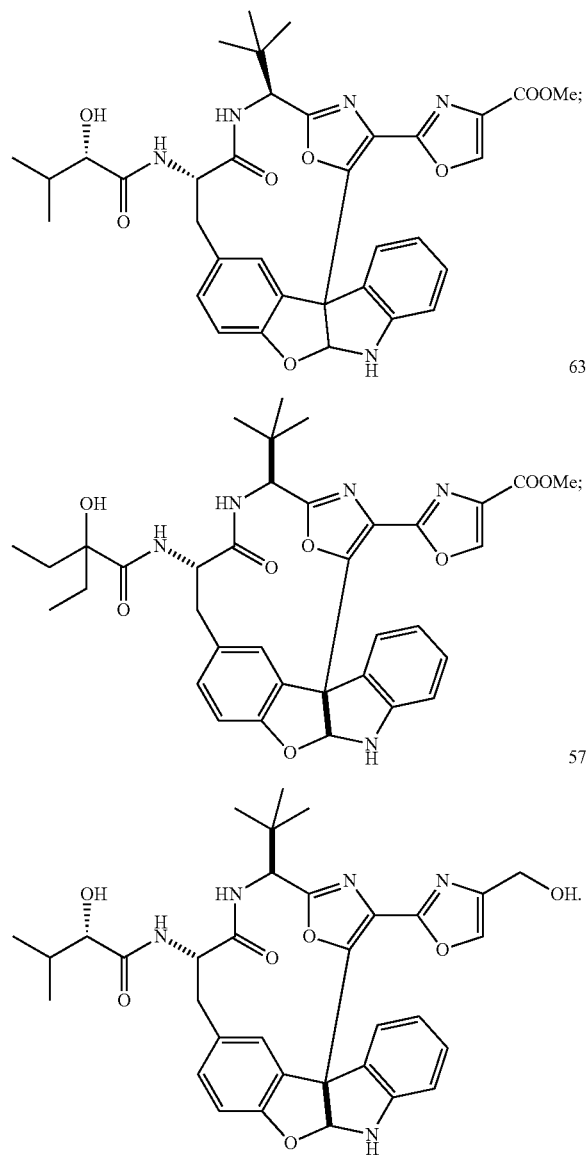

63

57

14. A compound of claim 1 having the following formula, or a pharmaceutically acceptable salt thereof:

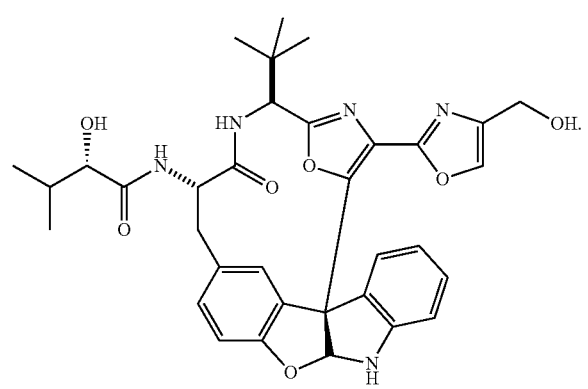

57

15. A compound of claim 1 having the following formula, or a pharmaceutically acceptable salt thereof:

81

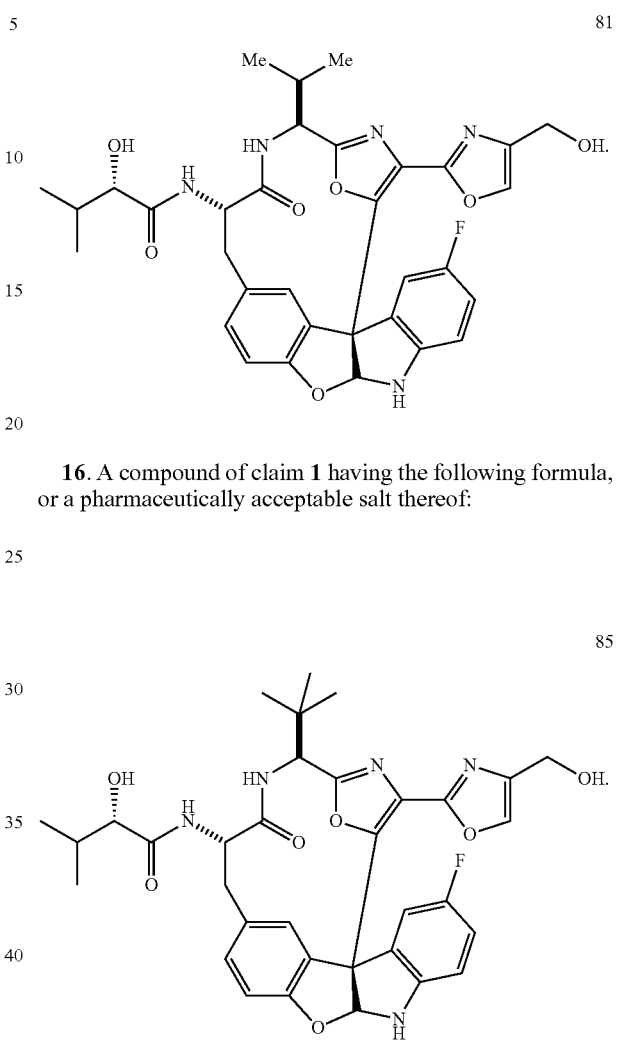

16. A compound of claim 1 having the following formula, or a pharmaceutically acceptable salt thereof:

85

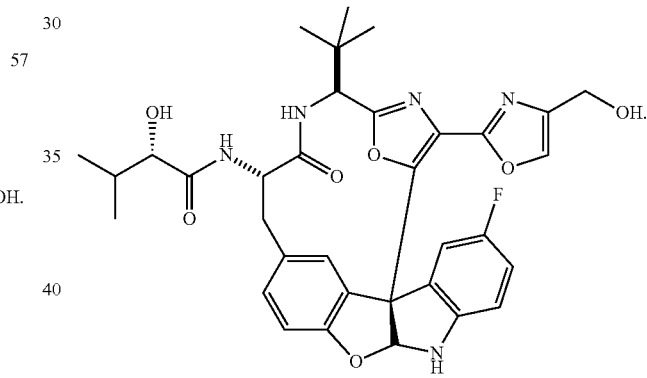

17. A compound of claim 1 having the following formula, or a pharmaceutically acceptable salt thereof:

86

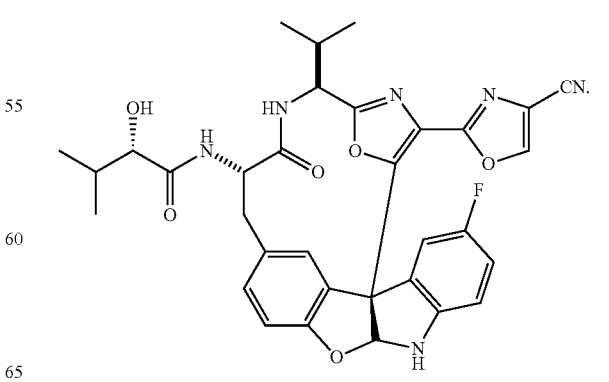

18. A compound of claim 1 having the following formula, or a pharmaceutically acceptable salt thereof:

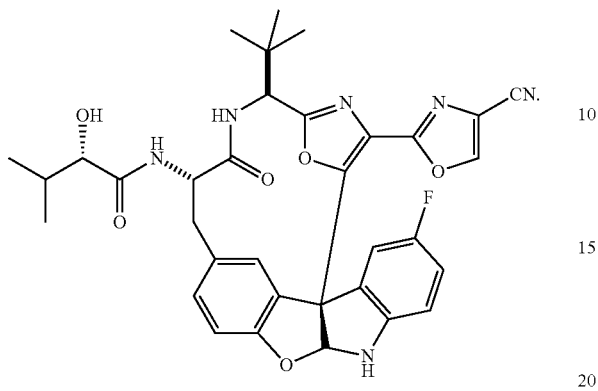

19. A pharmaceutical composition comprising (a) the compound of claim 1 in unit dosage form with at least one pharmaceutically acceptable excipient, or (b) the compound of claim 1 and a different chemotherapeutic drug.

20. A method of treating colon cancer comprising administering to a subject in need thereof a therapeutically effective amount of a compound of claim 1.

* * * * *

UNITED STATES PATENT AND TRADEMARK OFFICE
CERTIFICATE OF CORRECTION

PATENT NO.         : 8,592,469 B2                                    Page 1 of 1
APPLICATION NO.    : 13/447259
DATED              : November 26, 2013
INVENTOR(S)        : Qi Wei et al.

It is certified that error appears in the above-identified patent and that said Letters Patent is hereby corrected as shown below:

In the Claims

In claim 7 at col. 144, lines 55-65, the structure of compound 51 should be:

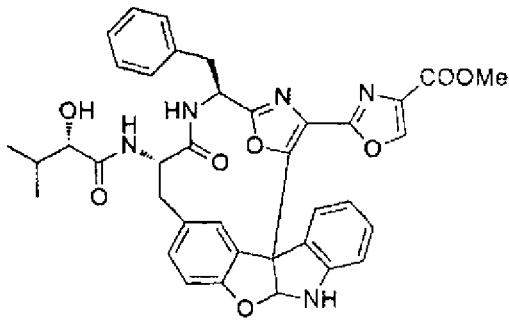

In claim 7 at col. 149, lines 10-20, the structure of compound 69 should be:

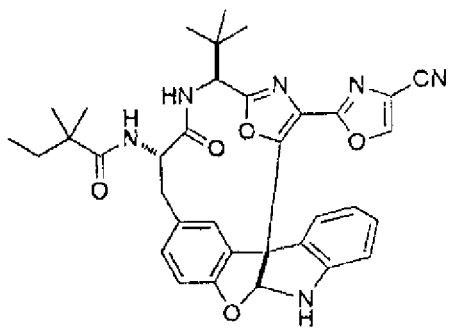

Signed and Sealed this
Twenty-first Day of October, 2014

Michelle K. Lee
*Deputy Director of the United States Patent and Trademark Office*